United States Patent
Saliman

(10) Patent No.: US 8,702,731 B2
(45) Date of Patent: Apr. 22, 2014

(54) SUTURING AND REPAIRING TISSUE USING IN VIVO SUTURE LOADING

(75) Inventor: Justin D. Saliman, Los Angeles, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 78 days.

(21) Appl. No.: 13/114,983

(22) Filed: May 24, 2011

(65) Prior Publication Data
US 2011/0270280 A1    Nov. 3, 2011

Related U.S. Application Data

(63) Continuation-in-part of application No. 11/773,388, filed on Jul. 3, 2007, now abandoned.

(60) Provisional application No. 61/347,720, filed on May 24, 2010, provisional application No. 61/347,713, filed on May 24, 2010.

(51) Int. Cl.
*A61B 17/04*    (2006.01)

(52) U.S. Cl.
USPC .......................................................... 606/145

(58) Field of Classification Search
USPC .......................... 606/145, 139, 144, 232, 300
See application file for complete search history.

(56) References Cited

U.S. PATENT DOCUMENTS

| | | | |
|---|---|---|---|
| 1,037,864 A | 9/1912 | Carlson et al. | |
| 2,738,790 A | 3/1956 | Todt, Sr. et al. | |
| 2,748,773 A | 6/1956 | Vacheresse, Jr. | |
| 3,470,875 A | 10/1969 | Johnson | |
| 3,580,256 A | 5/1971 | Wilkinson et al. | |
| 3,842,840 A | 10/1974 | Schweizer | |
| 3,901,244 A | 8/1975 | Schweizer | |
| 4,021,896 A | 5/1977 | Stierlein | |
| 4,109,658 A | 8/1978 | Hughes | |

(Continued)

FOREIGN PATENT DOCUMENTS

| EP | 0647431 A2 | 4/1995 |
|---|---|---|
| JP | 3032847 U | 3/1991 |

(Continued)

OTHER PUBLICATIONS

Saliman et al.; U.S. Appl. No. 13/247,892 entitled "Meniscus Repair," filed Sep. 28, 2011.

(Continued)

*Primary Examiner* — Corrine M McDermott
*Assistant Examiner* — Christopher L Templeton
(74) *Attorney, Agent, or Firm* — Shay Glenn LLP

(57) ABSTRACT

Described herein are methods of repairing tissue using a suture passer configured to relasably couple to a suturing element to pass the suturing element (and therefore a suture) through the tissue so that that the suture may be loaded and/or unloaded while the suture passer is positioned within the tissue. Thus, the methods described herein may allow the suture passer to be loaded without requiring that the suture passer be removed from within the patient or in some variations from off of the target tissue. The same suture or multiple sutures may thus be loaded and/or unloaded onto the suture passer, allowing the formation of complex suture patterns without requiring the extra steps of withdrawing the suture passer from the patient (or target tissue). Knotless suture anchors are also described.

15 Claims, 49 Drawing Sheets

(56) References Cited

U.S. PATENT DOCUMENTS

| | | | |
|---|---|---|---|
| 4,164,225 A | 8/1979 | Johnson et al. | |
| 4,236,470 A | 12/1980 | Stenson | |
| 4,345,601 A | 8/1982 | Fukuda | |
| 4,440,171 A | 4/1984 | Nomoto et al. | |
| 4,553,543 A | 11/1985 | Amarasinghe | |
| 4,605,002 A | 8/1986 | Rebuffat | |
| 4,706,666 A | 11/1987 | Sheets | |
| 4,836,205 A | 6/1989 | Barrett | |
| 4,923,461 A | 5/1990 | Caspari et al. | |
| 4,957,498 A | 9/1990 | Caspari et al. | |
| 4,981,149 A | 1/1991 | Yoon et al. | |
| 5,002,561 A | 3/1991 | Fisher | |
| 5,011,491 A | 4/1991 | Boenko et al. | |
| 5,037,433 A | 8/1991 | Wilk et al. | |
| 5,059,201 A | 10/1991 | Asnis | |
| 5,112,344 A | 5/1992 | Petros | |
| 5,129,912 A | 7/1992 | Noda et al. | |
| 5,156,608 A | 10/1992 | Troidl et al. | |
| 5,193,473 A | 3/1993 | Asao et al. | |
| 5,219,358 A | 6/1993 | Bendel et al. | |
| 5,222,962 A | 6/1993 | Burkhart | |
| 5,250,053 A | 10/1993 | Snyder | |
| 5,250,055 A | 10/1993 | Moore et al. | |
| 5,281,237 A * | 1/1994 | Gimpelson | 606/144 |
| 5,312,422 A | 5/1994 | Trott | |
| 5,330,488 A | 7/1994 | Goldrath | |
| 5,336,229 A | 8/1994 | Noda | |
| 5,342,389 A | 8/1994 | Haber et al. | |
| 5,364,410 A * | 11/1994 | Failla et al. | 606/148 |
| 5,368,601 A | 11/1994 | Sauer et al. | |
| 5,389,103 A | 2/1995 | Melzer et al. | |
| 5,391,174 A | 2/1995 | Weston | |
| 5,397,325 A | 3/1995 | Della Badia et al. | |
| 5,403,328 A | 4/1995 | Shallman | |
| 5,405,532 A | 4/1995 | Loew et al. | |
| 5,431,666 A | 7/1995 | Sauer et al. | |
| 5,437,681 A | 8/1995 | Meade et al. | |
| 5,454,823 A | 10/1995 | Richardson et al. | |
| 5,454,834 A * | 10/1995 | Boebel et al. | 606/228 |
| 5,474,057 A | 12/1995 | Makower et al. | |
| 5,478,344 A | 12/1995 | Stone et al. | |
| 5,478,345 A | 12/1995 | Stone et al. | |
| 5,480,406 A | 1/1996 | Nolan et al. | |
| 5,496,335 A | 3/1996 | Thomason et al. | |
| 5,499,991 A | 3/1996 | Garman et al. | |
| 5,507,757 A | 4/1996 | Sauer et al. | |
| 5,520,702 A | 5/1996 | Sauer et al. | |
| 5,540,704 A | 7/1996 | Gordon et al. | |
| 5,540,705 A | 7/1996 | Meade et al. | |
| 5,562,686 A | 10/1996 | Sauer et al. | |
| 5,569,301 A | 10/1996 | Granger et al. | |
| 5,571,090 A | 11/1996 | Sherts | |
| 5,571,119 A | 11/1996 | Atala | |
| 5,575,800 A | 11/1996 | Gordon | |
| 5,578,044 A | 11/1996 | Gordon et al. | |
| 5,616,131 A | 4/1997 | Sauer et al. | |
| 5,618,290 A | 4/1997 | Toy et al. | |
| 5,626,588 A | 5/1997 | Sauer et al. | |
| 5,632,751 A | 5/1997 | Piraka | |
| 5,643,289 A | 7/1997 | Sauer et al. | |
| 5,645,552 A | 7/1997 | Sherts | |
| 5,653,716 A * | 8/1997 | Malo et al. | 606/139 |
| 5,669,917 A | 9/1997 | Sauer et al. | |
| 5,674,229 A | 10/1997 | Tovey et al. | |
| 5,674,230 A | 10/1997 | Tovey et al. | |
| 5,681,331 A | 10/1997 | de la Torre et al. | |
| 5,690,652 A | 11/1997 | Wurster et al. | |
| 5,709,708 A | 1/1998 | Thal | |
| 5,713,910 A | 2/1998 | Gordon et al. | |
| 5,728,107 A | 3/1998 | Zlock et al. | |
| 5,728,113 A | 3/1998 | Sherts | |
| 5,730,747 A | 3/1998 | Ek et al. | |
| 5,741,278 A | 4/1998 | Stevens | |
| 5,749,879 A | 5/1998 | Middleman et al. | |
| 5,755,728 A | 5/1998 | Maki | |
| 5,759,188 A | 6/1998 | Yoon | |
| 5,766,183 A | 6/1998 | Sauer | |
| 5,792,153 A | 8/1998 | Swain et al. | |
| 5,800,445 A | 9/1998 | Ratcliff et al. | |
| 5,814,054 A | 9/1998 | Kortenbach et al. | |
| 5,824,009 A | 10/1998 | Fukuda et al. | |
| 5,827,300 A | 10/1998 | Fleega | |
| 5,843,126 A | 12/1998 | Jameel | |
| 5,865,836 A * | 2/1999 | Miller | 606/228 |
| 5,876,411 A | 3/1999 | Kontos | |
| 5,876,412 A | 3/1999 | Piraka | |
| 5,895,393 A | 4/1999 | Pagedas | |
| 5,895,395 A | 4/1999 | Yeung | |
| 5,897,563 A | 4/1999 | Yoon et al. | |
| 5,899,911 A | 5/1999 | Carter | |
| 5,899,920 A | 5/1999 | DeSatnick et al. | |
| 5,906,630 A | 5/1999 | Anderhub et al. | |
| 5,908,428 A | 6/1999 | Scirica et al. | |
| 5,935,138 A | 8/1999 | McJames, II et al. | |
| 5,938,668 A | 8/1999 | Scirica et al. | |
| 5,944,739 A | 8/1999 | Zlock et al. | |
| 5,947,982 A | 9/1999 | Duran | |
| 5,980,538 A | 11/1999 | Fuchs et al. | |
| 5,993,466 A | 11/1999 | Yoon | |
| 6,048,351 A | 4/2000 | Gordon et al. | |
| 6,051,006 A | 4/2000 | Shluzas et al. | |
| 6,053,933 A | 4/2000 | Balazs et al. | |
| 6,056,771 A | 5/2000 | Proto | |
| 6,071,289 A | 6/2000 | Stefanchik et al. | |
| 6,077,276 A | 6/2000 | Kontos | |
| 6,099,550 A | 8/2000 | Yoon | |
| 6,113,610 A | 9/2000 | Poncet | |
| 6,126,666 A | 10/2000 | Trapp et al. | |
| 6,129,741 A | 10/2000 | Wurster et al. | |
| 6,139,556 A | 10/2000 | Kontos | |
| 6,159,224 A | 12/2000 | Yoon | |
| 6,190,396 B1 | 2/2001 | Whitin et al. | |
| 6,221,085 B1 | 4/2001 | Djurovic | |
| 6,238,414 B1 | 5/2001 | Griffiths | |
| 6,264,694 B1 | 7/2001 | Weiler | |
| 6,277,132 B1 | 8/2001 | Brhel | |
| 6,322,570 B1 | 11/2001 | Matsutani et al. | |
| 6,325,808 B1 | 12/2001 | Bernard et al. | |
| 6,355,050 B1 | 3/2002 | Andreas et al. | |
| 6,368,334 B1 | 4/2002 | Sauer | |
| 6,443,963 B1 | 9/2002 | Baldwin et al. | |
| 6,511,487 B1 | 1/2003 | Oren et al. | |
| 6,533,795 B1 | 3/2003 | Tran et al. | |
| 6,533,796 B1 | 3/2003 | Sauer et al. | |
| 6,551,330 B1 | 4/2003 | Bain et al. | |
| 6,585,744 B1 | 7/2003 | Griffith | |
| 6,626,917 B1 | 9/2003 | Craig | |
| 6,626,929 B1 | 9/2003 | Bannerman | |
| 6,638,283 B2 | 10/2003 | Thal | |
| 6,638,286 B1 | 10/2003 | Burbank et al. | |
| 6,641,592 B1 | 11/2003 | Sauer et al. | |
| 6,719,765 B2 | 4/2004 | Bonutti | |
| 6,723,107 B1 | 4/2004 | Skiba et al. | |
| 6,770,084 B1 | 8/2004 | Bain et al. | |
| 6,896,686 B2 | 5/2005 | Weber | |
| 6,921,408 B2 | 7/2005 | Sauer | |
| 6,923,806 B2 | 8/2005 | Hooven et al. | |
| 6,923,819 B2 | 8/2005 | Meade et al. | |
| 6,936,054 B2 | 8/2005 | Chu | |
| 6,984,237 B2 | 1/2006 | Hatch et al. | |
| 6,991,635 B2 | 1/2006 | Takamoto et al. | |
| 6,997,931 B2 | 2/2006 | Sauer et al. | |
| 6,997,932 B2 | 2/2006 | Dreyfuss et al. | |
| 7,004,951 B2 | 2/2006 | Gibbens, III | |
| 7,029,480 B2 | 4/2006 | Klein et al. | |
| 7,029,481 B1 | 4/2006 | Burdulis, Jr. et al. | |
| 7,041,111 B2 | 5/2006 | Chu | |
| 7,063,710 B2 | 6/2006 | Takamoto et al. | |
| 7,087,060 B2 | 8/2006 | Clark | |
| 7,112,208 B2 | 9/2006 | Morris et al. | |
| 7,118,583 B2 | 10/2006 | O'Quinn et al. | |
| 7,131,978 B2 | 11/2006 | Sancoff et al. | |
| 7,166,116 B2 | 1/2007 | Lizardi et al. | |
| 7,175,636 B2 | 2/2007 | Yamamoto et al. | |

(56) References Cited

U.S. PATENT DOCUMENTS

| | | | |
|---|---|---|---|
| 7,211,093 B2 | 5/2007 | Sauer et al. | |
| 7,232,448 B2 | 6/2007 | Battles et al. | |
| 7,235,086 B2 | 6/2007 | Sauer et al. | |
| 7,311,715 B2 | 12/2007 | Sauer et al. | |
| 7,344,545 B2 | 3/2008 | Takemoto et al. | |
| 7,390,328 B2 | 6/2008 | Modesitt | |
| 7,481,817 B2 | 1/2009 | Sauer | |
| 7,491,212 B2 | 2/2009 | Sikora et al. | |
| 7,588,583 B2 | 9/2009 | Hamilton et al. | |
| 7,594,922 B1 | 9/2009 | Goble et al. | |
| 7,632,284 B2 | 12/2009 | Martinek et al. | |
| 7,674,276 B2 | 3/2010 | Stone et al. | |
| 7,731,727 B2 | 6/2010 | Sauer | |
| 7,736,372 B2 | 6/2010 | Reydel et al. | |
| 7,749,236 B2 | 7/2010 | Oberlaender et al. | |
| 7,842,050 B2 | 11/2010 | Diduch et al. | |
| 7,879,046 B2 | 2/2011 | Weinert et al. | |
| 7,883,519 B2 | 2/2011 | Oren et al. | |
| 7,918,868 B2 * | 4/2011 | Marshall et al. | 606/144 |
| 7,951,147 B2 | 5/2011 | Privitera et al. | |
| 7,951,159 B2 | 5/2011 | Stokes et al. | |
| 7,972,344 B2 | 7/2011 | Murray et al. | |
| 8,394,112 B2 | 3/2013 | Nason | |
| 2003/0023250 A1 | 1/2003 | Watschke et al. | |
| 2003/0065336 A1 | 4/2003 | Xiao | |
| 2003/0065337 A1 | 4/2003 | Topper et al. | |
| 2003/0078599 A1 | 4/2003 | O'Quinn et al. | |
| 2003/0204194 A1 | 10/2003 | Bittar | |
| 2003/0216755 A1 | 11/2003 | Shikhman et al. | |
| 2003/0233106 A1 | 12/2003 | Dreyfuss | |
| 2004/0249392 A1 | 12/2004 | Mikkaichi et al. | |
| 2004/0249394 A1 | 12/2004 | Morris et al. | |
| 2004/0267304 A1 | 12/2004 | Zannis et al. | |
| 2005/0033319 A1 | 2/2005 | Gambale et al. | |
| 2005/0033365 A1 | 2/2005 | Courage | |
| 2005/0080434 A1 | 4/2005 | Chung et al. | |
| 2005/0090837 A1 | 4/2005 | Sixto, Jr. et al. | |
| 2005/0090840 A1 | 4/2005 | Gerbino et al. | |
| 2005/0154403 A1 | 7/2005 | Sauer et al. | |
| 2005/0228406 A1 | 10/2005 | Bose | |
| 2005/0288690 A1 | 12/2005 | Bourque et al. | |
| 2006/0020272 A1 | 1/2006 | Gildenberg | |
| 2006/0047289 A1 | 3/2006 | Fogel | |
| 2006/0084974 A1 | 4/2006 | Privitera et al. | |
| 2006/0106423 A1 | 5/2006 | Weisel et al. | |
| 2007/0032799 A1 | 2/2007 | Pantages et al. | |
| 2007/0156150 A1 | 7/2007 | Fanton et al. | |
| 2007/0219571 A1 | 9/2007 | Balbierz et al. | |
| 2007/0250118 A1 | 10/2007 | Masini | |
| 2007/0260260 A1 | 11/2007 | Hahn et al. | |
| 2007/0260278 A1 | 11/2007 | Wheeler et al. | |
| 2008/0086147 A1 | 4/2008 | Knapp | |
| 2008/0091219 A1 | 4/2008 | Marshall et al. | |
| 2008/0097489 A1 | 4/2008 | Goldfarb et al. | |
| 2008/0140091 A1 | 6/2008 | DeDeyne et al. | |
| 2008/0228204 A1 | 9/2008 | Hamilton et al. | |
| 2008/0234725 A1 | 9/2008 | Griffiths et al. | |
| 2008/0243147 A1 | 10/2008 | Hamilton et al. | |
| 2008/0269783 A1 | 10/2008 | Griffith | |
| 2008/0294256 A1 | 11/2008 | Hagan et al. | |
| 2009/0012538 A1 | 1/2009 | Saliman | |
| 2009/0018554 A1 | 1/2009 | Thorne et al. | |
| 2009/0062816 A1 | 3/2009 | Weber | |
| 2009/0062819 A1 | 3/2009 | Burkhart et al. | |
| 2009/0105751 A1 | 4/2009 | Zentgraf | |
| 2009/0131956 A1 | 5/2009 | Dewey et al. | |
| 2009/0209998 A1 | 8/2009 | Widmann | |
| 2009/0216268 A1 | 8/2009 | Panter | |
| 2009/0228041 A1 | 9/2009 | Domingo | |
| 2009/0259233 A1 * | 10/2009 | Bogart et al. | 606/144 |
| 2009/0306684 A1 | 12/2009 | Stone et al. | |
| 2009/0306776 A1 | 12/2009 | Murray | |
| 2010/0057109 A1 | 3/2010 | Clerc et al. | |
| 2010/0106169 A1 | 4/2010 | Niese et al. | |
| 2010/0114137 A1 | 5/2010 | Vidal et al. | |
| 2010/0121352 A1 | 5/2010 | Murray et al. | |
| 2010/0130990 A1 | 5/2010 | Saliman | |
| 2010/0145364 A1 | 6/2010 | Keren et al. | |
| 2010/0185232 A1 | 7/2010 | Hughett et al. | |
| 2010/0198235 A1 | 8/2010 | Pierce et al. | |
| 2010/0228271 A1 | 9/2010 | Marshall et al. | |
| 2010/0241142 A1 | 9/2010 | Akyuz et al. | |
| 2010/0249809 A1 | 9/2010 | Singhatat et al. | |
| 2010/0280530 A1 | 11/2010 | Hashiba | |
| 2010/0305581 A1 | 12/2010 | Hart | |
| 2010/0305583 A1 | 12/2010 | Baird et al. | |
| 2010/0331863 A2 | 12/2010 | Saliman | |
| 2011/0028998 A1 | 2/2011 | Adams et al. | |
| 2011/0060350 A1 | 3/2011 | Powers et al. | |
| 2011/0087246 A1 | 4/2011 | Saliman et al. | |
| 2011/0112555 A1 | 5/2011 | Overes et al. | |
| 2011/0112556 A1 | 5/2011 | Saliman et al. | |
| 2011/0118760 A1 | 5/2011 | Gregoire et al. | |
| 2011/0130773 A1 | 6/2011 | Saliman et al. | |
| 2011/0152892 A1 | 6/2011 | Saliman et al. | |
| 2011/0190815 A1 | 8/2011 | Saliman | |
| 2011/0251626 A1 | 10/2011 | Wyman et al. | |
| 2012/0303046 A1 | 11/2012 | Stone et al. | |
| 2013/0238040 A1 | 9/2013 | Saliman et al. | |

FOREIGN PATENT DOCUMENTS

| | | |
|---|---|---|
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO 02/07607 A1 | 1/2002 |
| WO | WO 03/077771 A1 | 9/2003 |
| WO | WO 2005/037112 A1 | 4/2005 |
| WO | WO 2006/001040 A1 | 1/2006 |
| WO | WO 2010/141695 A1 | 12/2010 |

OTHER PUBLICATIONS

Saliman et al.; U.S. Appl. No. 13/323,391 entitled "Suture passer devices and methods," filed Dec. 12, 2011.

Cayenne Medical; CrossFix® II System (product webpage); 4 pgs.; downloaded Nov. 21, 2011 (www.cayennemedical.com/products/crossfix/).

Smith&Nephew; Fast-Fix Meniscal Repair System (product webpage); 4 pgs.; downloaded Nov. 21, 2011 (http://endo.smith-nephew.com/fr/node.asp?NodeId=3562).

Saliman, Justin D.; U.S. Appl. No. 13/347,184 entitled "Implant and method for repair of the anterior cruciate ligament," filed Jan. 10, 2012.

Saliman et al.; U.S. Appl. No. 13/462,760 entitled "Methods of Meniscus Repair," filed May 2, 2012.

Saliman et al.; U.S. Appl. No. 13/462,728 entitled "Devices, Systems and Methods for Meniscus Repair," filed May 2, 2012.

Murillo et al.; U.S. Appl. No. 13/462,773 entitled "Suture Passer Devices and Methods," filed May 2, 2012.

Asik et al.; Strength of different meniscus suturing techniques; Knee Sur, Sports Traumotol, Arthroscopy; vol. 5; No. 2; pp. 80-83; (month unavailable) 1997.

Asik et al.; Failure strength of repair devices versus meniscus suturing techniques; Knee Surg, Sports Traumatol, Arthrosc; vol. 10; No. 1; pp. 25-29; Jan. 2002.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Rimmer et al.; Failure Strength of Different Meniscal Suturing Techniques; Arthroscopy: The Journal of Arthroscopic and Related Surgery; vol. 11; No. 2; pp. 146-150; Apr. 1995.

Arthrex®, Arthrex, Inc., "The Next Generation in Shoulder Repair Technology," Product Brochure from Arthrex, Inc; Naples, Florida, 2007, 22 pages.

(56) References Cited

OTHER PUBLICATIONS

ArthroCare® Sportsmedicine, Sunnyvale, CA, SmartStitch® Suture Passing System with the PerfectPasserTM, Product brochure, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Depuy Mitek, Inc; Raynham, MA, "Versalok Surgical Technique for Rotator Cuff Repair: The next generation in rotator cuff repair," Product brochure, 2007, 18 pages.

Linvatec Conmed Company, Largo, Florida, Product descriptions B17-19, B21; Tissue Repair Systems, Tissue Repair Accessories, and Master Arthroscopy Shoulder Instrument Set, 4 pages.

Ma et al; "Biomechanical Evaluation of Arthroscopic Rotator Cuff Stitches," J Bone Joint Surg Am, 2004; 86:1211-1216.

Nho et al; "Biomechanical fixation in Arthroscopic Rotator Cuff Repair," Arthroscopy: J of Arthroscop and Related Surg; vol. 23. No. 1 (Jan. 2007): pp. 94-102.

Schneeberger, et al; "Mechanical Strength of Arthroscopic Rotator Cuff Repair Techniques: An in Vitro Study," J Bone Joint Surg Am., 2002; 84:2152-2160.

Tornier, Inc.; CINCH(TM) Knotless Fixation Implant System; 510K (K080335); 6 pgs.; Feb. 6, 2008.

USS SportsMedicine ArthoSewTM Single Use Automated Suturing Device with 8.6 mm ArthroPort Cannula Set, Instructions for Use, <http:www.uss-sportsmed.com/imageServeraspx?contentID=5020&contenttype=application/pdf> accessed Apr. 25, 2007, 2 pages.

USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

Saliman, Justin; U.S. Appl. No. 13/090,089 entitled "Methods of meniscus repair," filed Apr. 19, 2011.

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

MEDSFERA; Suturing devices; accessed Dec. 4, 2012 at <http://www.medsfera.ru/shiv.html> 13 pages.

Strobel; Manual of Arthroscopic Surgery (1st Edition); Springer Verlag, Hiedelberg © 2002; pp. 127-129; Dec. 15, 2001.

Hirotsuka et al.; U.S. Appl. No. 13/758,994 entitled "Pre-Tied Surgical Knots for Use With Suture Passers," filed Feb. 4, 2013.

McCutcheon et al.; U.S. Appl. No. 13/759,000 entitled "Methods and Devices for Preventing Tissue Bridging While Suturing," filed Feb. 4, 2013.

Saliman, J.; U.S. Appl. No. 13/759,006 entitled "Suture Passers," filed Feb. 4, 2013.

Duerig, T. et al., "An overview of nitinol medical applications" Materials Science and Engineering A273-275, May 1999.

Hendricksen et al.; U.S. Appl. No. 13/844,252 entitled "Suture passers and methods of passing suture," filed Mar. 15, 2013.

Saliman et al.; U.S. Appl. No. 13/893,209 entitled "Implant and method for repair of the anterior cruciate ligament," filed May 13, 2013.

Murillo et al.; U.S. Appl. No. 13/893,154 entitled "Suture passer devices and methods," filed May 13, 2013.

\* cited by examiner

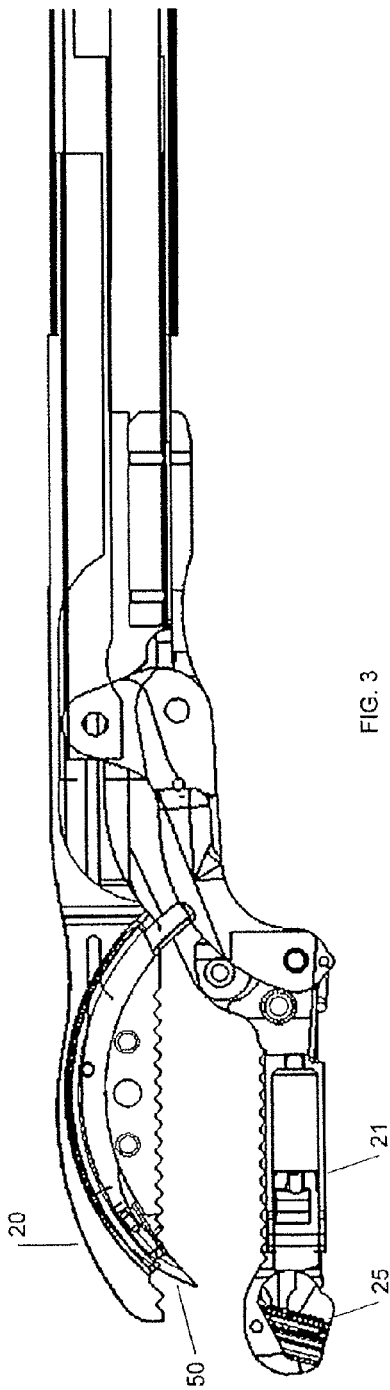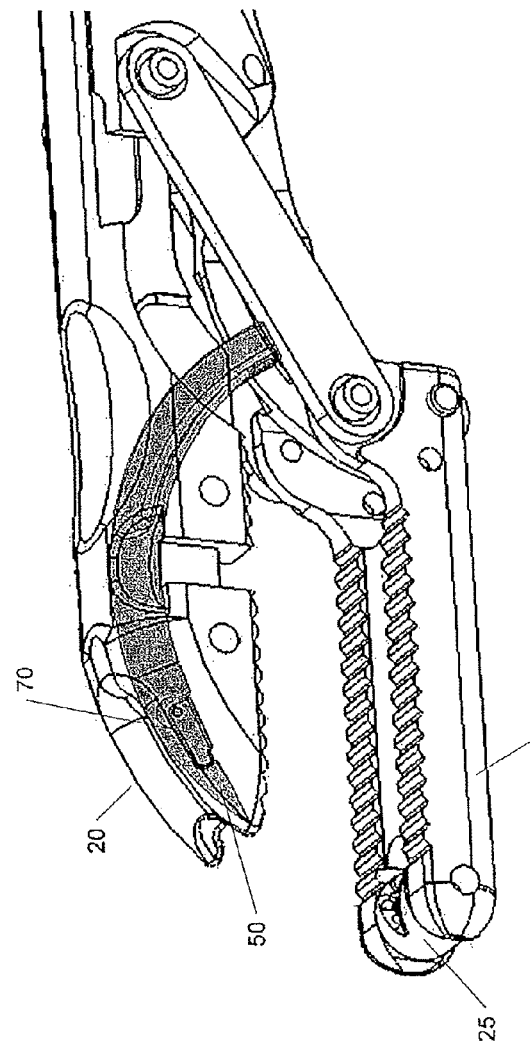

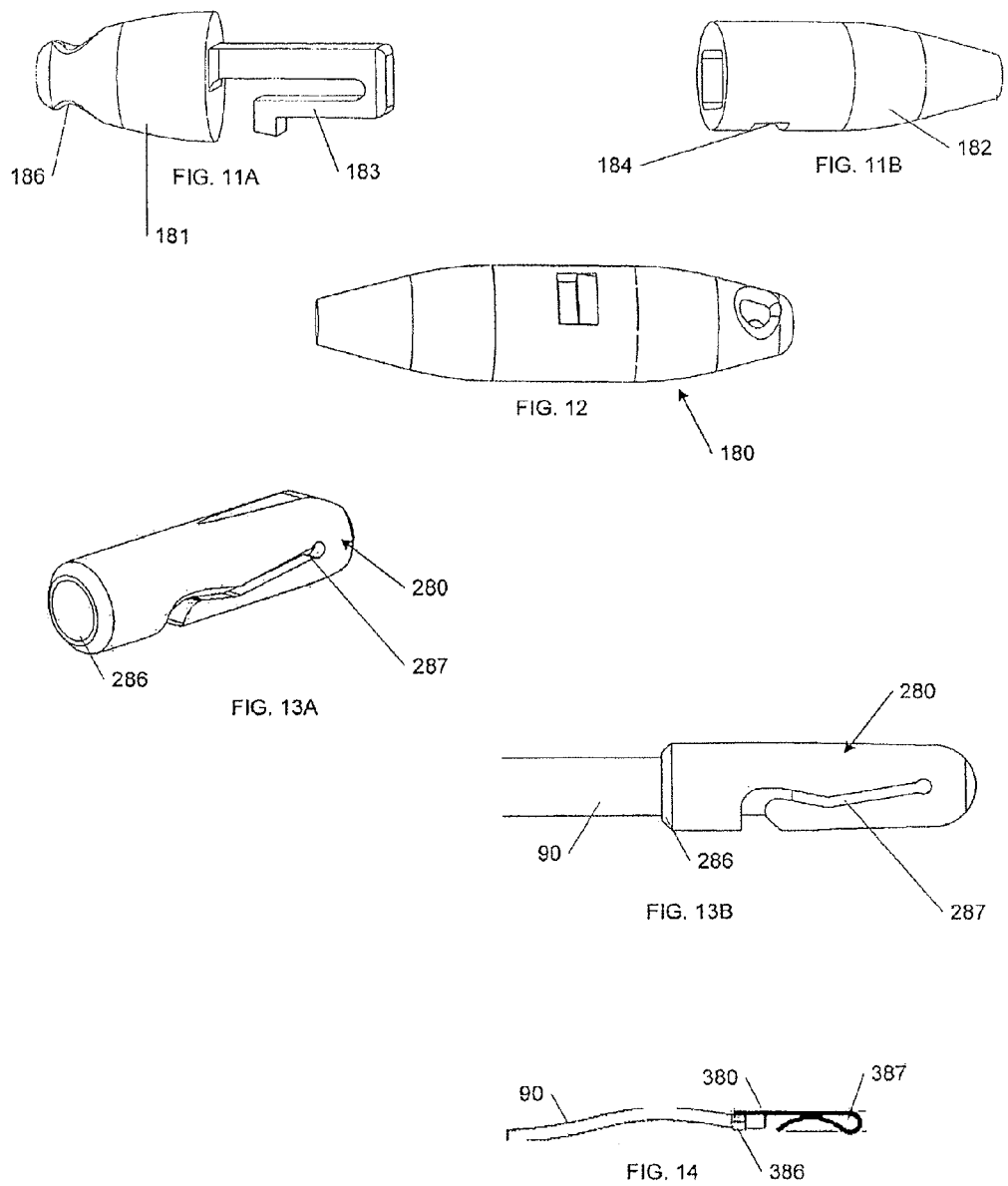

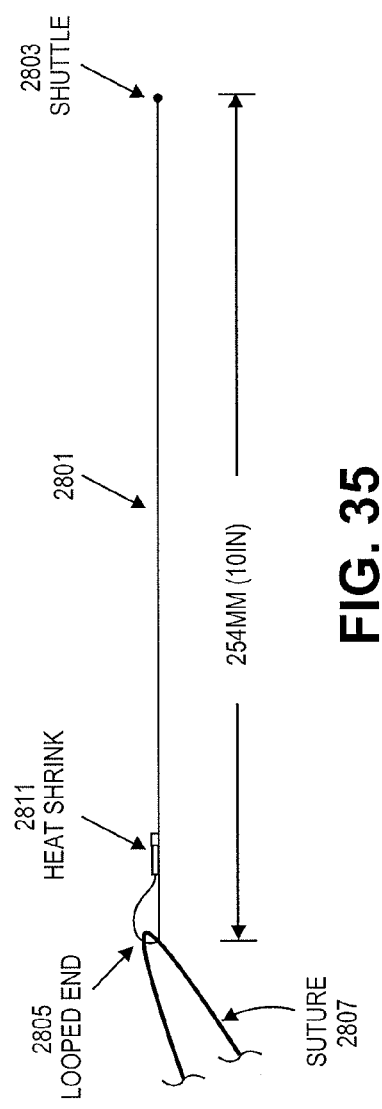
FIG. 35
FIG. 36A
FIG. 36B

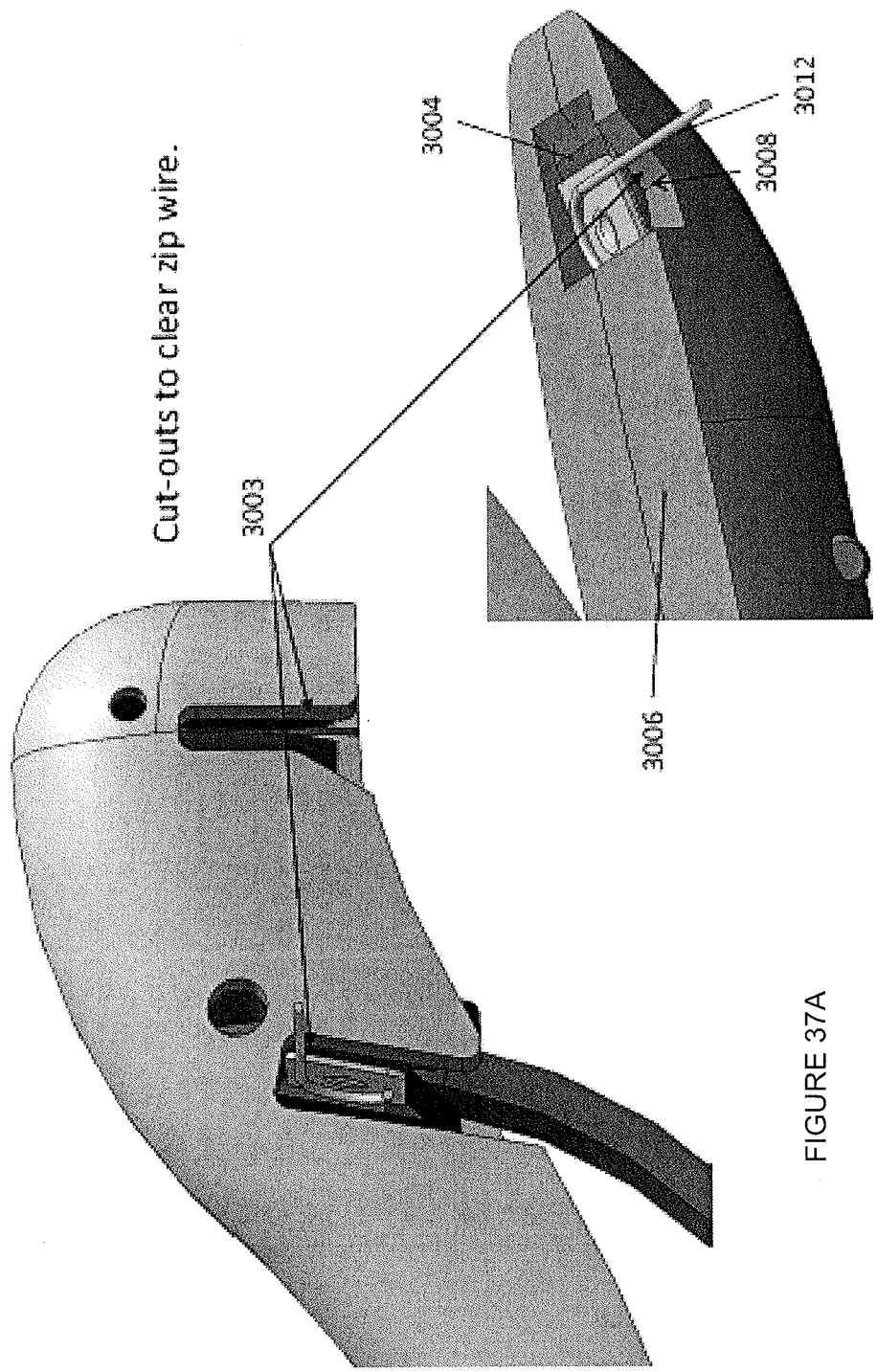

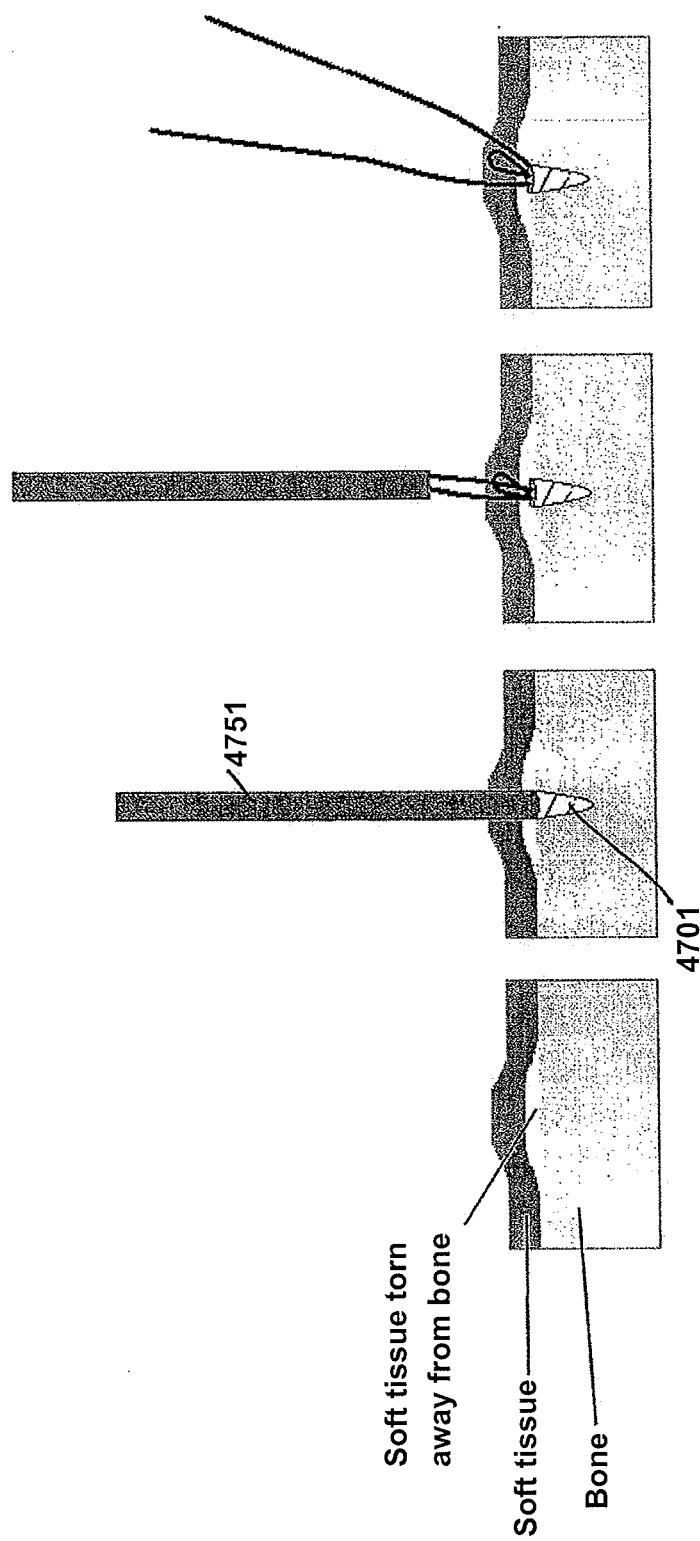

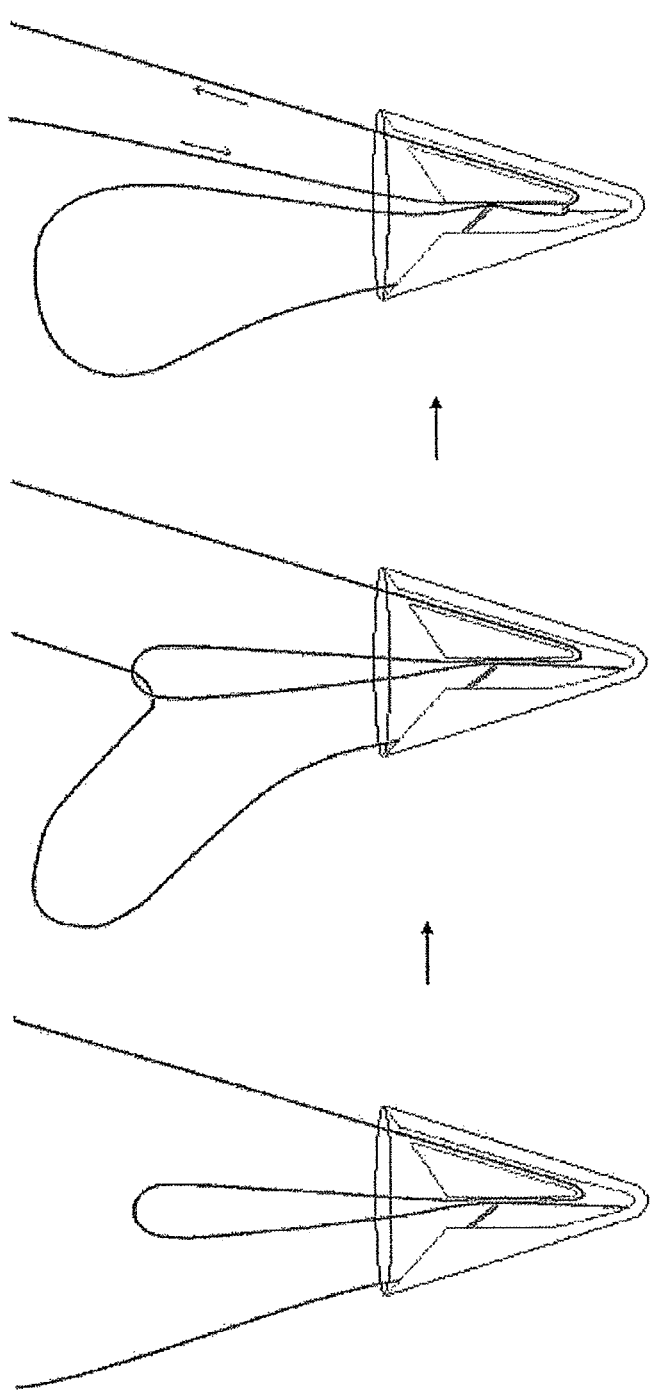

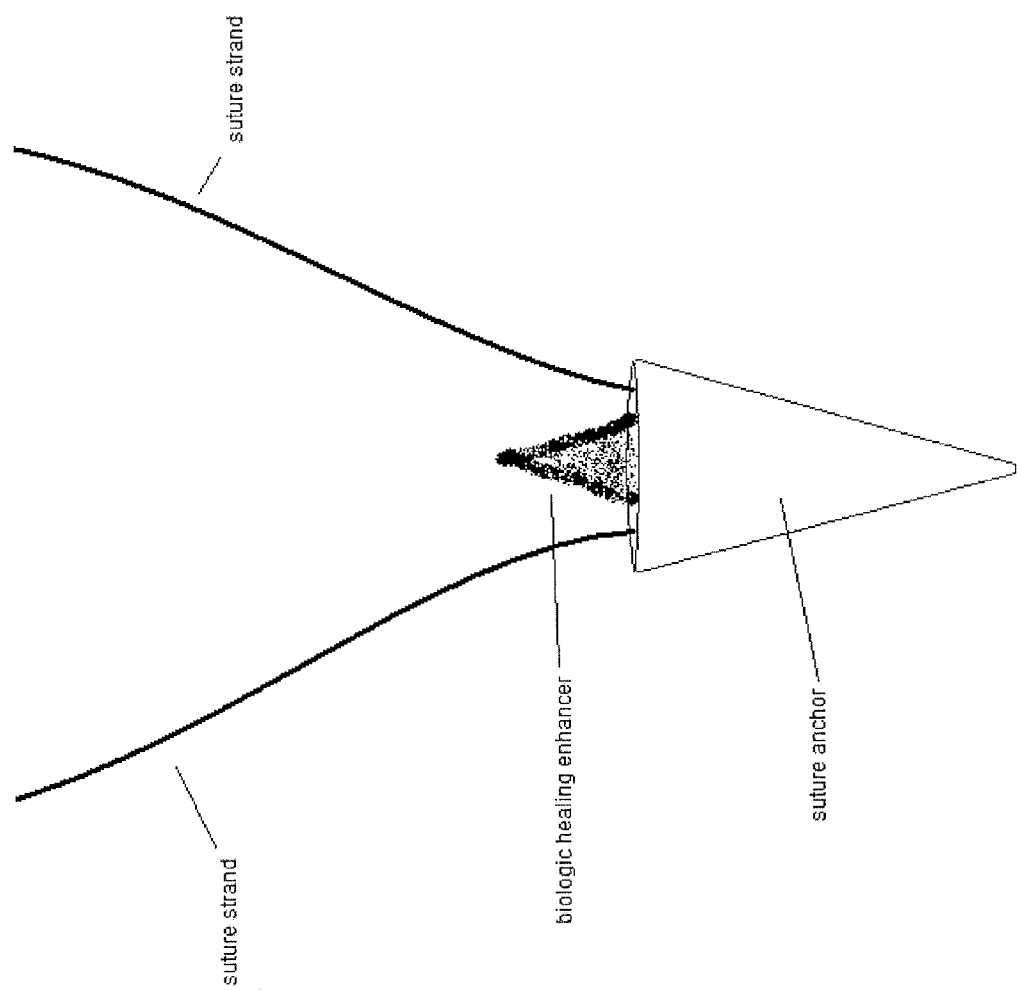

SUTURING AND REPAIRING TISSUE USING IN VIVO SUTURE LOADING

CROSS REFERENCE TO RELATED APPLICATIONS

This application claim priority to and the benefit of the filing dates of U.S. Provisional Patent Application No. 61/347,720, titled "SUTURING AND REPAIRING TISSUE USING IN VIVO SUTURE LOADING," filed on May 24, 2010; and 61/347,713, titled "KNOTLESS SUTURE ANCHORS WITH THERAPEUTIC SPIKE," filed on May 24, 2010, the disclosures of which are herein incorporated by reference in their entirety, as if fully set forth herein.

This application is also a continuation-in-part of U.S. patent application Ser. No. 11/773,388, now abandoned, titled "METHODS AND DEVICES FOR CONTINUOUS SUTURE PASSING," filed on Jul. 3, 2007, Publication No. 2009/0012538, the disclosure of which is incorporated herein by reference as if fully set forth herein.

This patent application may be related to U.S. patent application Ser. No. 12/620,029, titled "METHODS OF SUTURING AND REPAIRING TISSUE USING A CONTINUOUS SUTURE PASSER DEVICE," filed on Nov. 17, 2009, Publication No. 2010/0130990; and U.S. patent application Ser. No. 12/291,159, titled "SUTURE PASSING INSTRUMENT AND METHOD" filed on Nov. 5, 2008, Publication No. 2010/0331863. This patent may also be related to International Patent Application No. PCT/US2009/056152, titled "KNOTLESS SUTURE ANCHORS", filed on Sep. 8, 2009, Publication No. WO 2010/028324. Each of these patent applications is herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND OF THE INVENTION

Suturing instruments for assisting a medical practitioner in placing stitches during surgical procedures are useful, particularly in surgical procedures requiring the placement of secure and accurate sutures in difficult to access regions of the body, including internal body regions. Instruments and methods for suturing remotely are especially important in minimally invasive surgical procedures such as laparoscopic and endoscopic procedures. In addition to helping to access remote regions of the body requiring suturing, suturing instruments may also allow the efficient manipulation of very small needles and the formation of small and precise sutures Arthroscopic rotator cuff repair is one example of a technically challenging procedure that requires the placement of sutures in difficult to reach regions, as well requiring precise placement of sutures. The procedure may be performed with the patient under general anesthesia, and small (e.g., 5 mm) incisions may be created in the back, side, and front of the shoulder, and an arthroscope and instruments may be switched between each of these positions as necessary. The rotator cuff tear may be visualized, and the size and pattern of the tear is assessed. Thin or fragmented portions are removed and the area where the tendon will be reattached to the bone is lightly debrided to encourage new blood vessel ingrowth for healing. Sutures may be placed to close a tear. Depending on the size and location of the tear, multiple suture stitches may be required. In many situations, an arthroscopic stitch passer and grasper are used to pass a suture through the tendon. A stitch passer and grabber are typically only capable of making a single stitch, and must be withdrawn and reloaded in order to make multiple stitches. Similarly, a separate arthroscopic knot tying instrument is typically used to pass and tie knots in the suture to secure the repair. Furthermore, most currently available suturing instruments are limited in their ability to be maneuvered, particularly over thicker tissue regions, and may require additional space so that additional surgical instruments, including forceps or other graspers.

For example, the ArthroSew™ is a commercially available bi-directional suturing device with multiple-pass capability that has two jaws hinged to open V-like (from a common pivot). A suture is attached to the center of a double-ended needle and can be passed between the two jaws. At least one end of the needle protrudes from one or the other jaw at all times. The protruding needle may become caught in tissue, a problem that is exacerbated in difficult to access regions and regions offering limited maneuverability, such as the subacromial space of the shoulder. In addition, it is not possible to pass a stitch through thick (>4 or 5 mm) tissue because if the needle is too long then the device cannot be inserted through a cannula and is not easily manipulated around or off of tissue when sewing. When attempts are made to pass a stitch through such thick tissues, the needle commonly is released free within the shoulder because it is not captured within the far jaw (the needle does not make it all the way through the tissue). Additionally, the ArthroSew™ and similar devices require the user to flip a toggle switch in the handle each time the user desires to alternate the needle between the jaws while sewing. This step has been shown to be difficult for surgeons to master. Similar devices are described in U.S. Pat. Nos. 5,814,054, 5,645,552, 5,389,103, 5,645,552, and 5,571,090. Other suture passers (including continuous suture passers) include rotating suture passers, in which a curved suture needle is driven about an axis through successive revolutions to pass through an adjacent tissue, forming a spiral stitch through the tissue. U.S. Pat. No. 5,540,705 to Meade et al., describes one such embodiment.

Meniscus repair is another example of a technically challenging procedure that requires the placement of sutures in difficult to reach regions. The meniscus is a C-shaped piece of fibrocartilage which is located at the peripheral aspect of the joint (e.g., the knee) between the condyles of the femur and the tibia on the lateral and medial sides of the knee. The central $^{2}/_{3}^{rds}$ of the meniscus has a limited blood supply while the peripheral $^{1}/_{3}^{rd}$ typically has an excellent blood supply. Acute traumatic events commonly cause meniscus tears in younger patients while degenerative tears are common in older patients as the menisci become increasingly brittle with age. Typically, when the meniscus is damaged, a torn piece may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for the visualization of the structures within that joint. Then, using miniature instruments which may be as small as 1/10 of an inch, the structures are examined and the surgery is performed.

A typical meniscus has a flattened ("bottom") and a concave top, and the outer cross-sectional shape is somewhat triangular. The outer edge of the meniscus transitions into the capsule. There are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed.

Most prior art devices for suturing or repairing the meniscus are only capable of reliably repairing vertical/longitudinal tears. Such devices are not typically recommended for repair of radial tears, particularly not arthroscopically/minimally invasively. Further, the prior art devices typically place horizontal mattress suture patterns rather than vertical mattress suture patterns because vertical patterns are considerably more difficult (if not impossible) for surgeons to place when using these devices. Vertical mattress patterns would have improved pull through strength because of the aforementioned predominance of circumferential collagen fibers found within the meniscus structure. See, e.g., Boenisch, U. W., et al, "Pull-out strength and stiffness of meniscal repair using absorbable arrows or Ti-Cron vertical and horizontal loop sutures," *Am J Sports Med.* 1999 September-October; 27(5):626-31. Additionally; prior art devices are only capable of point fixation; that is they cannot compress the tears uniformly across the torn surface. Finally, such prior art devices are designed for repairing peripheral vertical meniscus tears (torn from the superior surface to the inferior surface in line with the C-shape of the meniscus) and are incapable of repairing commonly encountered radial meniscus tears.

There is a need for methods and device capable of repairing tissue particularly tissue that is difficult to access, in particular, it would be useful to provide methods and device for repair of tissue in which the suture or stitch may be formed completely from within the tissue (e.g., in a closed, minimally invasive, or percutaneous procedure), including loading and unloading of the suture passing element. The methods and system described herein may address some of these needs. Also described herein are systems and devices, including anchors and anchoring systems, which may be used to repair tissue.

SUMMARY OF THE INVENTION

The methods and devices described herein generally relate to methods of treating tissue using surgical stitching devices by which a stitch or continuous stitches may be made during surgery. In particular, described herein are method of suturing tissue using a suture passer, including coupling and/or uncoupling the suture to the suture passer without removing the suture passer from the tissue. Any appropriate suture passer may be used. In some variations, the suture passers include arms which extend or are extendable to form a distal-facing opening which may be placed over tissue. For example, in some variations, the suture passer devices used may have jaws that open and close in parallel, and that are capable of passing a suture using a suture shuttle when the jaws are open in any position. Any of these suture passers may be "continuous" suture passers which may be used to make multiple sequential stitches through the tissue without requiring the device be removed from the tissue. Although many variations of continuous suture passers described herein include a suture shuttle, the methods described herein are not limited to continuous suture passers having a suture shuttle. In general, the suturing methods described herein may allow suturing of the tissue without removing the device (e.g., the suture passer device) from the tissue in order to load the suture for passage through the tissue one or more times.

The suture passers described herein may be configured for use with a suture passing element, such as a shuttle and/or lead wire, which may be passed by the device through the tissue; the suture passing element (e.g., suturing element) may include a loop or other suture attachment region allowing a suture to be loaded while the device is operated within the tissue.

For example, described herein are suturing techniques, methods, and suture patterns that may be useful for securing tissue. These techniques may, for the first time, be used to suture tissue using a suture passer device that may allow minimally or non-invasive suturing of extremely hard-to-reach areas, which would not otherwise be accessible without requiring the suture passer device to be withdrawn and reloaded into the tissue.

For example, described herein are methods of loading (or re-loading) the suture passer device while the device remains within the tissue to pass one, two, or more stitches, including forming a complex suture pattern in tissue using a suture passer. In some variations the device is loaded and/or reloaded with a suture while the suture passer device remains on the tissue, without removing the device e.g., the jaws of the device) from on or around the target tissue to be sutured. In general, a complex suture pattern may comprise a suture pattern in which the suture is passed first in a first direction through the tissue, and then in a second position through the tissue; multiple such passes (in different directions, e.g., up then down, down, then up, etc.) through the tissue are typically made to form the suture pattern. Examples of such complex suture patterns are provided herein.

In some variations, described herein are methods of suturing tissue using a suture passer that is loaded with a suture while a loadable end of the suture passer is positioned within the tissue. The method may include: positioning the suture passer within the tissue, wherein the suture passer is configured to pull a suture shuttle through the tissue; coupling the suture to the loadable end of the suture passer, while the loadable end of the suture passer and the suture are within the tissue; and passing the suture through the tissue using the suture passer.

The loadable end of the suture passer is typically the distal end of the suture passer that is inserted into the tissue. For example, the loadable end of a suture passer including a suture shuttle is typically the region of the suture passer to which the suture shuttle couples (e.g., the "jaws" in some variations).

For example, described herein are methods of suturing tissue using a suture passer that is loaded with the suture while the suture passer is positioned within the tissue, the method comprising the steps of: positioning a suture passer within the tissue, wherein the suture passer is configured to pass a suture shuttle through the tissue.; coupling a suture to a suture shuttle while the suture shuttle and the suture are within the tissue; and passing the suture shuttle with the coupled suture through the tissue using the continuous suture passer.

In general, any appropriate suture shuttle may be used. For example, the step of coupling may include passing a suture through an eyelet of the suture shuttle. The suture shuttle may be a clip-type shuttle, a ball-type shuttle, a bullet-type shuttle, a needle-type shuttle, or the like. In some variation the shuttle includes an extension region that my comprise a clip, loop, or the like, to which the suture may be coupled or otherwise connected. The suture may be passed through the loop so that the suture can slide relative to the shuttle, or it may be secured in or to the shuttle at a fixed or adjustable position on the length of the suture.

In some variations of the method an additional tool may be used to connect the suture to a suture shuttle. For example, the step of coupling may comprise using a hooked tool to pull the suture through an opening of the suture shuttle.

The method may also include a step of anchoring the suture to the tissue before coupling the suture to the suture shuttle. Thus, the suture may already be present within the tissue at or near the point at which the suture passer is inserted into the tissue. The suture may be anchored to bone or other tissue. In some variations the suture was previously passed by a suture passer (or by a needle) and has been passed through the tissue.

The method may also comprise a step of de-coupling the suture from the suture shuttle. For example, the method allows a suture to be unconnected and re-connected to a continuous suture passer (e.g., to the suture shuttle of the suture passer) for passing it though the tissue multiple times, or for removing it from the tissue. Thus, the method may include a step of de-coupling the suture from the suture shuttle while the continuous suture passer remains within the tissue. The method may further comprise coupling the same or a different suture to the suture shuttle, as mentioned.

Any appropriate continuous suture passer may be used, particularly those adapted to pass a suture shuttle back and forth through tissue multiple times, such as those described herein. For example, in some variations the method includes the step of positing a continuous suture passer within the tissue wherein the continuous suture passer comprises a first and second jaw and a tissue penetrator configured so that the tissue penetrator is configured to extend from the first jaw, through the tissue and engage the second jaw, to alternately exchange the suture shuttle between the tissue penetrator and the second jaw.

The coupling step may include coupling the suture to the suture shuttle when the suture shuttle is releasably secured within the continuous suture passer.

Also described herein are methods of suturing tissue comprising: inserting a continuous suture passer comprising a suture shuttle within the tissue; coupling a suture to the suture shuttle while the suture and suture shuttle are within the tissue; passing the suture shuttle through the tissue and pulling the suture coupled to the suture shuttle through the tissue.

Any of the variations described above may be used (or adapted for use) with these methods as well. For example, the suture may be anchored within the tissue prior to connection to the suture shuttle and/or suture passer.

In some variations, the method includes a step of pulling the suture shuttle through the tissue a second time without removing the continuous suture passer from the tissue.

In any of these methods, the step of coupling the suture to the suture shuttle may include inserting a tool into the tissue to grasp the suture and manipulating the tool to couple the suture to the suture shuttle. Any appropriate tool may be used, including a hook, grasper, clamp, etc. These tools, including the suture passer and/or a suture grasping/manipulating tool, may be inserted into the tissue (e.g., the region of the tissue near the distal end of the continuous suture passer) percutaneously or using an open surgical procedure.

The step of coupling may include passing the suture through an eyelet on the suture shuttle, or otherwise connecting the suture to the suture shuttle.

BRIEF DESCRIPTION OF THE DRAWINGS

FIG. 3 illustrates a cross-sectional view of the distal end of one embodiment of the suture passer device.

FIG. 4 illustrates a close-up, perspective view of the distal end of one embodiment of the suture passer device, wherein the upper jaw is transparent.

FIGS. 11A-B illustrate another embodiment of the suture clip, split into two pieces.

FIG. 12 illustrates the suture clip of FIGS. 11A-B, but combined to form the complete suture clip.

FIG. 13A-13B illustrates another embodiment of the suture clip.

FIG. 14 illustrates yet a further embodiment of the suture clip.

FIG. 35 illustrates an enlarged view of one variation of a pull wire.

FIGS. 36A and 36B illustrate other variation of a suture passing element (e.g., a suture shuttle and pull wire in this example).

FIGS. 37A and 37B illustrate one variation of a suture device including arms adapted for use with a pull wire. In particular, these variations include cut-out regions allowing passage of the pull wire as it is passed between the arms during use.

FIG. 45A-45D illustrate implantation of the knotless tissue anchor in bone.

FIG. 47A shows another variation of a knotless suture anchor, as described herein.

FIGS. 47B and 47C illustrate operation of the knotless suture anchor shown in FIG. 47A.

FIG. 54 illustrates a knotless suture anchor having a therapeutic spike.

DETAILED DESCRIPTION OF THE INVENTION

Described herein are systems, devices and methods for using a continuous suture passer to load (and/or unload) a suture from the suture passer within the tissue, without requiring withdrawal of the suture passer from the tissue. As described in greater detail below, any appropriate suture passer may be used, including those having a suture shuttle element to which a suture may be coupled. Kits, systems, or devices may also include one or more elongate manipulators, hooks, graspers, loaders, or the like for coupling/uncoupling the suture from the suture passer (e.g., a suture passing element, such as a shuttle and/or pull wire) while the suture and suture passer are within the tissue.

Examples of suture passers that may be used are described and illustrated below. For example, the methods described herein may be performed with continuous suture passers having jaws that open and close. In addition, the suture passer jaws may lock (e.g., so that tissue can be secured between them), and the suture may be passed by means of a tissue penetrator that carries the suture (e.g., attached to a suture shuttle) between the two jaws. In some variations, these methods may be performed using a suture passer device that is configured to pass the suture between the jaws regardless of the position of the jaws relative to each other (e.g., the jaws are not required to be in a particular position in order to pass the suture there between).

Suture Passers

Described herein are continuous suture passers for passing a suture through tissue, as well as systems including suture passers, and methods of passing sutures through tissue. In general, the suture passers described herein can be loaded with a suture while both a portion of the suture passer and the suture are within the tissue, e.g., the loading can be performed percutaneously. In one example, the suture passers are continuous suture passers that are configured to pass a suture back and forth through a tissue without having to remove the device from the tissue in order to reload the suture into the device (or a suture shuttle of the device). These continuous suture passers may be used for continuous stitching of tissue, and may allow stitching tissue that would otherwise not be accessible. Further, because the suture passers described herein can be loaded while within the tissue, they can avoid problems with suture tangling during insertion of the suture passer. Further, the suture passers described herein can advantageously be used with a suture that is already anchored to tissue or bone, allowing for a more stable stitch.

In general, the suture passers described herein are continuous suture passers that are configured to pass a suture back and forth through a tissue without having to withdraw the device from the tissue to reload the suture into the device or to remove the suture from the device.

Figure 1A:
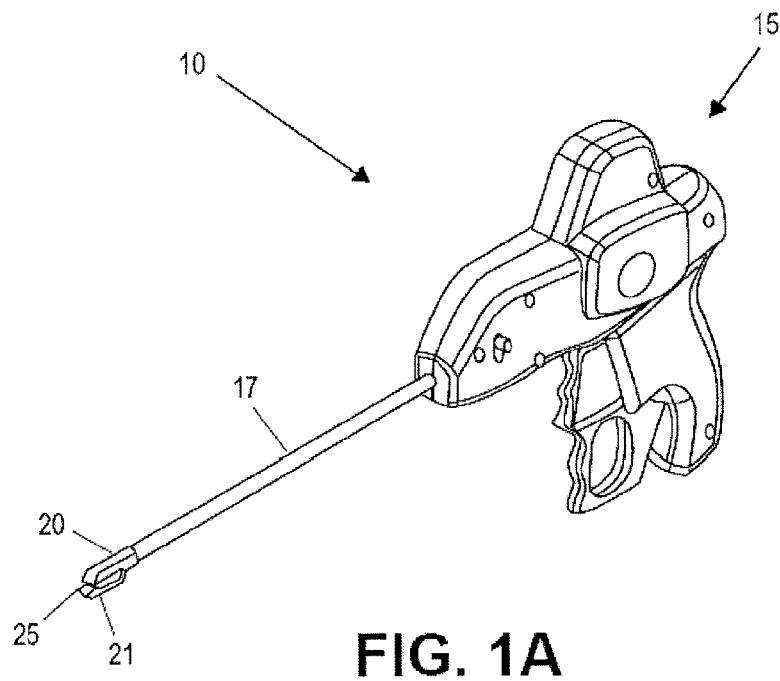
FIG. 1A is a perspective view of a first embodiment suture passer device.
Figure 1B:
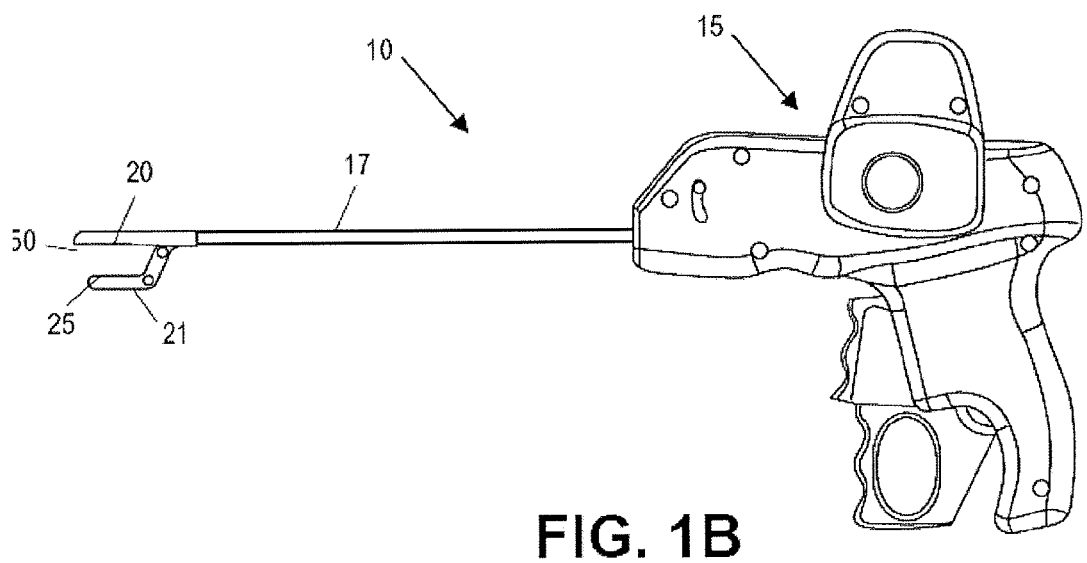
FIG. 1B illustrates a planar view of the suture passer device of FIG. 1A.

Any appropriate suture passer may be used with the methods described herein, particularly those that use a suture shuttle that is passed between two or more regions of a suture passer. FIG. 1A illustrates a first embodiment of a continuous suture passer 10, including some of the features described herein, which may include a tissue penetrator, shuttle, reciprocating parallel-opening first and second jaws 20 and 21, jaw lock, and lower-jaw shuttle retainer seat 25. FIG. 1B shows a planar view of the device 10, including the parallel-opening jaws 20 and 21, tissue penetrator 50, and lower-jaw shuttle retainer seat 25.

Figure 2:
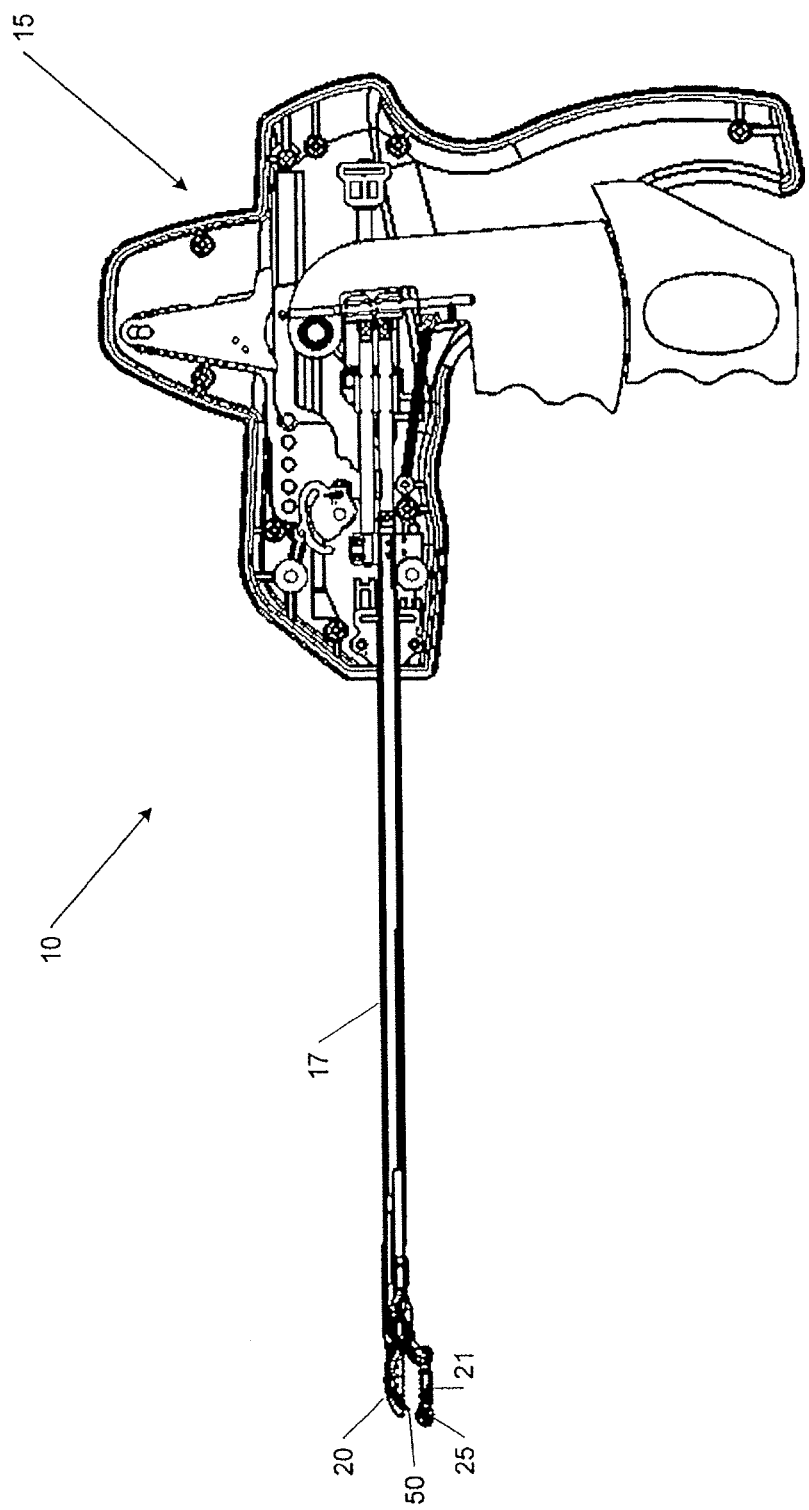
FIG. 2 illustrates a cross-sectional view of one embodiment of the suture passer device.

FIG. 2 illustrates a cross-sectional view of a first embodiment device 10. An actuator portion 15 of device 10 may include the mechanical elements which operate the entire device 10. For example, the actuator 15 includes mechanical elements for movement of at least one of the jaws 20 and 21, movement of the tissue penetrator 50, and retainer pin 30 (not shown), and associated equipment. Actuator 15 may be, in one embodiment, a handle. However, actuator 15 could also be any other type of mechanism to interface the device 10 with a user, such as, a keyboard or remote control for electronic embodiments of the device 10.

FIGS. 3 and 4 show enlarged sectional views of the distal end of device 10. In FIG. 3, one embodiment of the distal portion of device 10 is shown in cross-section. Tissue penetrator 50 is retracted within upper jaw 20, and shuttle retainer seat 25 is positioned near the distal end of lower jaw 21. Tissue penetrator 50 may move from a retracted position, as shown, to an extended position whereby tissue penetrator 50 may move out of the distal end of upper jaw 20 and towards lower jaw 21 and shuttle retainer seat 25.

FIG. 4 illustrates another embodiment of the relationship of tissue penetrator 50 with a shuttle 70. The upper jaw 20 is shown as translucent to uncover detail of tissue penetrator 50 and shuttle 70. Shuttle 70 engages the tissue penetrator such that it can extend from upper jaw 20 along with tissue penetrator 50 towards lower jaw 21 and shuttle retainer seat 25. In this variation, the tissue penetrator that passes the suture through the tissue is completely retracted into the upper jaw, as indicated. Thus, the jaws of the device may be opened and closed and used to grasp/manipulate tissue without engaging the tissue penetrator.

FIGS. 5A-7 illustrate various shuttle embodiments 70, 170 and 270. Shuttle 70, 170 and 270 may be any shape such that it may be releasably attached to tissue penetrator 50. While the shape of shuttle 70, 170 and 270 may correspond to the shape of at least a portion of the tissue penetrator 50 for attachment purposes, it may be of any suitable shape. In these illustrative examples, the shuttle is generally triangular in shape, which may correspond to a tissue penetrator 50 having a generally triangular cross-sectional shape. The illustrated examples of suture shuttles are "channel shuttles" which may engage a tissue penetrator 50. For example, a triangular or cylindrical tissue penetrator 50 may be used, as illustrated in FIGS. 8-9D, to which the suture shuttle 70, 170 and 270 is adapted to connect. Tissue penetrator 50 may be, for example, a needle or any like instrument capable of puncturing through tissue. Shuttle 70, 170 and 270 may be substantially hollow within the triangular shape, and may further have a channel 71, 171 and 271, or opening, along a portion of the triangular body. This channel 71, 171 or 271 may serve as an entry way for tissue penetrator 50 to engage the shuttle 70, 170 and 270. Thus, in these embodiments, the shuttle 70, 170 and 270 wraps around a portion of the tissue penetrator 50, which is positioned within the body of the shuttle. The shuttle may "snap" onto the tissue penetrator, or it may be more actively engaged. For example, the shuttle may be sufficiently elastically deformable so that it can snap onto the tissue penetrator, e.g., by expanding the channel region temporarily when force is applied to snap the shuttle on/off of the tissue penetrator.

Figure 5A:
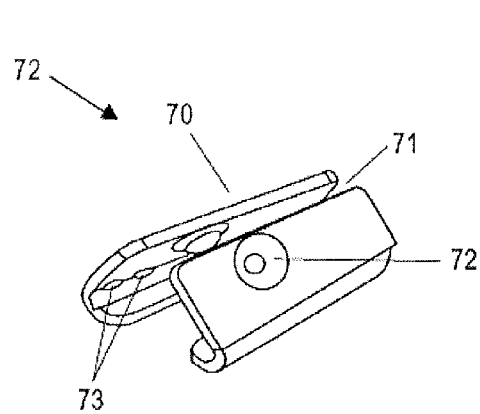
FIGS. 5A and 5B illustrate one embodiment of a suture shuttle.
Figure 5B:
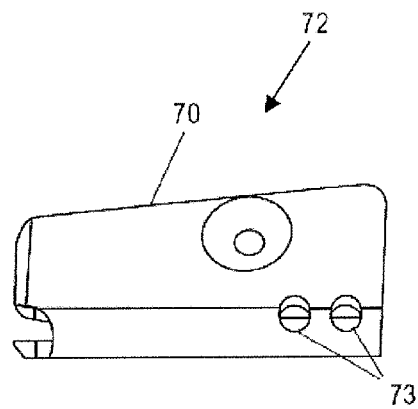
Figure 6A:
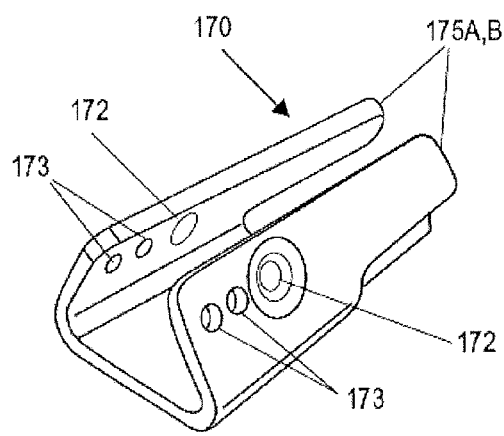
FIGS. 6A and 6B illustrate another embodiment of the suture shuttle.
Figure 6B:
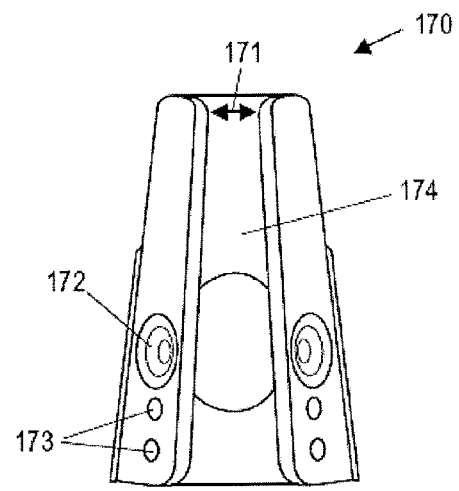

For example, in FIGS. 5A-B, the channel 71 may be positioned on any portion of the shuttle 70. In the illustrated examples, the channel is positioned along an apex of the triangular shape. However, a channel may also be placed along a side of triangular shape or in any other appropriate place.

Some embodiments of shuttle 170, 270 may also contain openings 74, 274 which may make the shuttle lighter, and may also facilitate flexing of the shuttle so that it can readily attach/detach from the tissue penetrator 50. Further, opening 74, 274 may provide an area through which a retaining mechanism, such as a retainer pin 30, may pass to secure shuttle 170, 270.

As described in detail below, any of the suture shuttle variations described herein may include a coupler or connector region for coupling to a suture (or more than one suture). The coupler may include a clip, loop, hook, eyelet, or the like, and may be an integral part of the body of the shuttle, or it may extend from the shuttle by a rigid or flexible extender, for example, on a tail, chain, wire, etc.

Some embodiments of shuttle 70, 170, 270 of the present invention may include additional features which may provide controllable, positive, robust, repeatable, and manufacturable retaining structures. Such features may include, for example, protrusions, such as dimples 72, 172 or the like, and finger springs 175a and b, both of which may help to retain shuttle 170 on the tissue penetrator 50.

The protruding dimples 72, 172 may interact with divots 52, 152 located within a cut-out 51, 151, or recessed portion, of the tissue penetrator 50. The dimples 72, 172 allow for controllable, repeatable retaining of the shuttle 70, 170 on the tissue penetrator 50, whereby the shuttle may, in one embodiment, snap on and off the tissue penetrator repeatedly, as necessary. In one embodiment, the position of shuttle 70, 170 on the tissue penetrator 50 may be the same given an additional feature such as the dimples and divots. In an alternative embodiment, dimples 72, 172 may be located on the tissue penetrator 50, while the divots 52, 152 may be located on the suture shuttle 70, 170.

In a further embodiment, the tissue penetrator 50 may include a cut-out region 51, shown in FIGS. 8-9D, that may be configured to seat the shuttle against the outer surface of the tissue penetrator, thereby allowing the tissue penetrator to present a uniform outer surface as it penetrates the tissue; in this example, the shuttle does not "stick out" from the tissue penetrator, but is flush with the outer surface of the tissue penetrator. This helps keep the shuttle on the tissue penetrator as it extends from upper jaw 20 and penetrates tissue.

Additionally, in some variations, the upper edge 54 of tissue penetrator 50 may be sharpened to provide additional cutting surface on tissue penetrator. In this variation, the shuttle 70 should not interact with the upper edge 54 such that upper edge 54 is exposed to assist in the piercing action of tissue penetrator. In some embodiments, tissue penetrator 50 may include an additional cut-out 51' along a portion of tissue penetrator 50 within cut-out 51. Cut-out 51' may allow additional room for a linkage 85 (see FIG. 15, for example). Cut-out 51' may reduce the chance of damage to linkage 85 during tissue penetrator 50 insertion into shuttle 70, since cut-out 51' may provide additional clearance for linkage 85.

In some embodiments, for example in FIGS. 6A-B and 9A-D, finger springs 175a and 175b may interact with a ramp 153 within the cut-out 151 of the tissue penetrator 150. The finger springs, and even the entire sides of the shuttle 170, may be sloped inwardly towards one end of the shuttle. Thus, in this embodiment, the finger springs are located at the narrowest portion of the shuttle. This slope of the finger springs may interact with the slope of the ramp 153 of the cut-out portion 151. The interaction of these two slopes may regulate the holding force of the shuttle 170 on the tissue penetrator 150 prior to the dimples 172 interacting with the divots 152 to firmly secure the shuttle to the tissue penetrator. Likewise, the holding force may be regulated as the shuttle is removed from the tissue penetrator in a similar manner. Thus, when a force is applied to shuttle 170 to pull shuttle 170 off tissue penetrator 150, the finger springs may be forced along the ramp, towards the tip of tissue penetrator, to engage the ramp, causing the finger springs, and thus the sides of the shuttle, to flex apart from one another, and disengage the dimples from the divots.

Figure 9A:
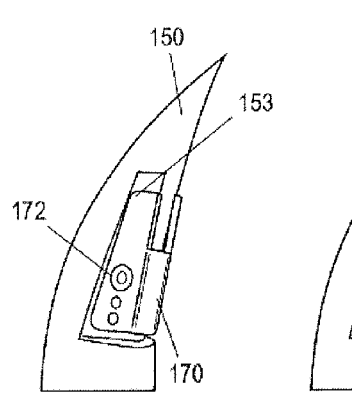
FIGS. 9A-9D illustrate one embodiment of the interaction between the suture shuttle and the tissue penetrator.
Figure 9B:
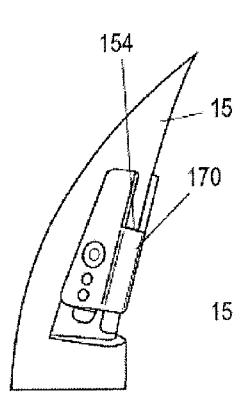
Figure 9C:
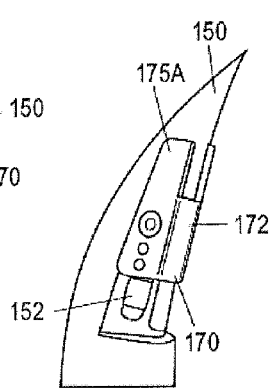
Figure 9D:
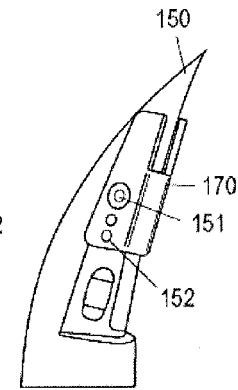

Continuing with this embodiment, in FIG. 9A, for example, the dimple 172 of the shuttle is shown engaged with the divot 152 on the tissue penetrator 150. At this point, the finger springs may only be slightly engaged to the tissue penetrator. FIG. 9B illustrates the shuttle 170 beginning to be removed from tissue penetrator. The dimple is no longer in the divot and is instead moving along the surface of the tissue penetrator. The finger springs 175a are increasingly engaged onto the tissue penetrator as they move along ramp 153 within cut-out on tissue penetrator. In FIG. 9C, the finger springs are shown as fully engaged with tissue penetrator, particularly at the point where the ramp ends (at the distal end of cut-out portion). This full engagement may, in one embodiment, cause the shuttle to flex, and as a result widen, such that the dimples are no longer in contact with the cut-out portion of the tissue penetrator. FIG. 9D illustrates the final step wherein the dimple and finger spring are no longer touching the tissue penetrator at all, and the tissue penetrator may be retracted, leaving the shuttle 170 free.

Thus, in various embodiments the tissue penetrator 50 may be adapted to mate with one or more elements on the suture shuttle, whether it is a dimple, or like protrusion, or finger springs, or the like, that can engage with a divot, depression, cut-out or ramp portion on the tissue penetrator.

Shuttle 70, 170 and 270 may be made of any material suitable for use in surgical applications. In one embodiment, the shuttle must have strength, yet also have sufficient flexibility and resiliency to be able to move on and off the tissue penetrator as described. Such movement may require the shuttle to flex during removal from and addition to the tissue penetrator. Thus, a suitable spring characteristic may be achieved with a high stiffness material, such as steel, by designing the spring such that it has a high preload characteristic when installed relative to the tolerances. For example, one shuttle design illustrated herein may include retention features that are lower spring stiffness & high preload, which may help provide more consistent performance and decrease sensitivity to tolerances. Note that the intrinsic stiffness of the material (Young's modulus) and the spring constant of the shuttle may be related, but may not be equivalent. In addition, these shuttle designs may have significantly reduced tolerance sensitivity, wherein the tolerance is a small percentage of deflection, compared to other shuttle designs. One suitable material may be stainless steel. For example, the shuttle may be composed of 0.004 in. (0.01 mm) thick 17-7 PH stainless steel, Condition CH-900. In other variations, the shuttle does not have to snap onto the tissue penetrator, but may be retained (e.g., friction fit) on the tissue penetrator. In still other variations, the shuttle may be locked on the tissue penetrator by a lock mechanism (shuttle lock on the tissue penetrator) such as a spring element. In other variations the shuttle is retained within the tissue penetrator, as previously described.

Shuttle 70'may be made of material whose hardness is matched to the tissue penetrator 50. Tissue penetrators of a material that is too hard relative to the shuttle may wear the shuttle out. In one example, the tissue penetrator is stainless steel, Rockwell 60C hardness. For example, the shuttle then may be precipitation hardened stainless steel, "17-4 PH", which is also known as stainless steel grade 630. The shape of the shuttle is matched to the shape of the tissue penetrator, and the shuttle clips onto a portion of the tissue penetrator, and can be slipped on and off repeatedly.

The shuttle 70 may be made of a material having a hardness, stiffness and elasticity sufficient so that it may partially elastically deflect to clamp onto the tissue penetrator 50, as mentioned. In particular, we have found that matching the hardness of the shuttle to the hardness of the tissue penetrator may be particularly useful for repeated use. For example, the shuttle may be made of Nitinol, beryllium copper, copper, stainless steel, and alloys of stainless steel (e.g., precipitation hardened stainless steel such as 17-7 PH stainless steel), cement (ceramic and metal), various polymers, or other biocompatible materials. The material chosen may be matched to the material of the tissue penetrator for various properties including, for example, hardness and the like. The shuttles may be formed in any appropriate manner, including punching, progressive die, CNC, photolithography, molding, etc.

In the above examples, a pull-out force, or the force required to remove the shuttle 70 from the tissue penetrator 50, may be more than about 2 pounds of force. Preferably, the force may be about 2 to about 5 pounds. The force may be from, for example, the pulling of a suture, or suture clip or connector, attached through one of the bore holes 73 located on shuttle 70. This force should be from the direction of about the tip of the tissue penetrator.

In one variation, illustrated in FIGS. 5A-B, the bore holes 73 are located away from channel 71 and towards the base of the triangle, which may be in a fold in the shuttle, as shown in FIG. 5B. In the other illustrated embodiments, FIGS. 6A-7 for example, the bore holes 173 are adjacent the channel. FIGS. 5A-B illustrate a position of bore holes 73 which may reduce, or even eliminate, the bending forces on the sides of shuttle 70, when suture, or the like, applies a force at bore holes 73. Typically, when bore holes 73 are located adjacent channel, as in FIG. 6A, the bending force on the side of the shuttle may peel the shuttle from the tissue penetrator 50 at a force lower than the desired removal force, due to the advantage of the force being applied to a corner of the shuttle 70. However, bore holes 73 located as shown in FIG. 5B limits this bending force, or torque, and thus prevents removal of shuttle 70 from tissue penetrator 50 at a premature time and at a force less than is desired for removal of shuttle 70.

In some embodiments, the shuttle 70 may be in the shape of a spiraled wire, or the like, such as a "finger torture" type device, whereby as the shuttle is pulled by the tissue penetrator 50, the shuttle may tighten around, thereby securing itself to the tissue penetrator. The stronger the force of the pull, the tighter the spiraled wire secures to the tissue penetrator. When the shuttle is to be transferred from the tissue penetrator, for example, to the shuttle retainer seat 25, the shuttle may be twisted, or the like, to "unlock" the shuttle from the tissue penetrator.

Other examples of suture shuttles 70, which may be able to clamp onto the tissue penetrator to secure itself, may include torsion springs, snap rings, a portion of wire, elastically deformable shapes, conically tapered shapes, and the like. Elastically deformable shapes may be any shape desired, such that it can be deformed to wrap around at least a portion of the tissue penetrator. Useful shapes may include, but are not limited to, cylinders, triangles, overlapping rings, and any partial portion of a shape such as a semi-circle. Once the tissue penetrator is in position, the shape of the tissue penetrator receiving area allows the elastically deformable shape to return to its original configuration while being securely attached to the tissue penetrator. Of course, the cut-out 51, or recess, or receiving area, on the tissue penetrator may in one embodiment be shaped such that it coincides with the shape of the shuttle. For example, if a conically tapered shuttle were used, the tissue penetrator may include a conically tapered cut-out on a portion of the surface. The conically tapered shuttle may be deformable, and may deform upon being moved into the cut-out region. Once completely within the cut-out region, the conically tapered shuttle may then return to its original shape and secure itself within the cut-out region. The cut-out region may include, for example, a lip, or the like, to assist in securing the shuttle, fully or partially, within the cut-out region.

In other embodiments, the shuttle may constitute the tip of the tissue penetrator 50 itself, such that the tip may be releasably coupled on the end of the tissue penetrator. Thus, the tip of the tissue penetrator may be passed between jaws of the suture passer device to pass the suture, which suture is attached to the tip, back and forth through the tissue. Suture 90 may, in one embodiment, be attached directly to shuttle 70 at bore hole 73, or other like retention location. The suture need not be secured only by a bore hole. Instead, a suture may be secured to the shuttle by adhesive, a clamp, by being ties or engaged to a portion of the shuttle, or in any other suitable manner.

As mentioned briefly above, a suture 90 may be secured to a suture shuttle 70 via an intermediary region, such as the various examples in FIGS. 10-15. One such intermediary element may be a suture clip, or suture retainer, 80, 180, 280, 380. A suture clip allows for simple and efficient releasable connection of a suture to a shuttle. A suture clip may be used for continuous suture passing, or alternatively for single passing of a suture. In some variations, this suture clip or retainer is simply a loop or eyelet through which the suture may be threaded, particularly when the suture passer with the shuttle are within the tissue (e.g., without removing them from the tissue). Thus, the loop or eyelet may be sufficiently large to allow the suture to be manipulated by a manipulating device such as an elongated hook, probe, forceps, etc. and placed through the loop or eyelet, or otherwise engaged with the suture retainer portion of the suture shuttle. This loading/coupling of the suture using an elongate manipulator may be performed while the suture is within the tissue.

In operation, suture loops (or clips, etc.) 80, 180, 280, 380, some examples of which are illustrated in FIGS. 10-15, may be used as part of a system for suturing tissue, particularly when used with a continuous suture passer 10. For example, a suture 90 may be passed from the first jaw 20 to the second jaw 21 and/or back from the second jaw to the first jaw of a suture passer. This may be accomplished using an extendable tissue penetrator 50 that is connected to the first jaw. The extendable tissue penetrator can pierce the tissue, and can also engage a suture shuttle 70, to which a suture is attached through the suture clip 80, 180, 280, 380. The suture may then be pulled through the passage that the tissue penetrator forms in the tissue. Extending the tissue penetrator forms a passage through the tissue, which may also pass the suture between the first and second jaws. For example, the tissue penetrator may include a suture shuttle engagement region which may be, for example, a cavity within the tissue penetrator, along the outside of the tissue penetrator, or the like, to which the suture shuttle can be releasably attached. The suture can be passed from the tissue penetrator in the first jaw to or from a suture shuttle retainer seat 25 connected to the second jaw. Thus, in some variations, both the tissue penetrator and the suture shuttle retainer seat are configured to releasably secure the suture, which may be attached to a suture shuttle.

In some variations, the suture clip 80, 180, 280, 380 described herein may include an attachment linkage 85 to a suture shuttle 70, for example a tether, leash, lead wire, or the like, which may be configured to connect the suture clip to the shuttle. In some examples, the suture clip includes a bias, for example, a spring, for securing a linkage 85 within a snap-fit element. Alternatively, the suture clip may include a central opening through which a linkage may be threaded. This linkage can act as a spacer. In one embodiment, the linkage may be stiffly attached to the shuttle 70 such that it both spaces the shuttle from the suture and also controls the position of the shuttle based on a force exerted on the linkage. The linkage may also control the position of the suture as the shuttle is passed from one jaw to the other. Similarly, the linkage 85 may be a stiff metallic wire, a portion of suture, a flexible polymeric strand, or the like. In the example of a stiff metallic wire, the wire may be welded to the shuttle such that it may project from the shuttle in a predictable manner.

Figure 10:
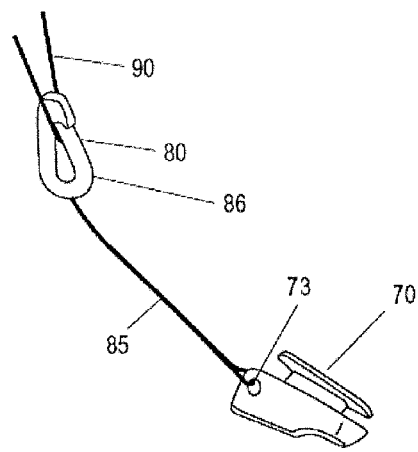
FIG. 10 illustrates a first embodiment of a suture clip.

In one embodiment, illustrated in FIG. 10, the shuttle 70 may be connected to a suture clip 80 that may be a compressed loop, in which the compressed loop has an inner, generally "teardrop" shaped opening 86 that is wider in one end than the other. The suture 90 may then be threaded through the inner loop 86 such that it becomes wedged within the narrow portion of the teardrop shape. The suture may then be secured by any method known in the art such as by tying a knot or bringing the end outside of the body. The suture may also be secured solely by being wedged within the teardrop shape, which may be sufficient to secure the suture within the suture clip.

In an alternative embodiment, the suture clip may be a ring, which may have a circular outer shape and a circular inner opening. In this example, the suture would be passed through the circular inner opening and secured by any method known in the art such that the suture is not easily separable from the suture clip. In another embodiment, the suture clip 180, illustrated in FIGS. 11-12, may be a two-piece assembly that snaps together. The first piece 181 may include a connector 186 for one of the suture 90 or linkage 85, while the second piece 182 may include a connector for the other of the suture 90 or linkage 85. For example, a suture may be formed onto the second piece 182, or knotted onto the second piece, or the like. The first and second pieces are configured to be secured together. In some variations, the first and second pieces are configured to be releasably secured together. For example, the first and second piece may be snapped together, but may include a releasable securing element 183, such as a button or the like, for separating them.

In FIGS. 11A-B, the suture clip 180 is shown with the first and second pieces 181 and 182 forming the clip 180 when connected together. The clip 180 may be configured so that it may readily pass through tissue. For example, the shape may be smooth, and may be tapered along the axis of its length. The surface may be lubricious or otherwise coated. Other shapes are possible. This "snap-fit" example of a suture clip also may include a suture retaining location on either of the pieces, or, alternatively, in between the two pieces. A lead wire, or other extension, may be secured within the eyelet 186, or alternatively on the tip of the second piece 182, or also secure in between the two pieces.

The clip 180 may be separated into the first and second pieces by releasing the securing element 183 between the two pieces. The first and second pieces of the assembly may also be referred to as "male" and "female" components. In the example shown in FIGS. 11A-B, the pieces may be separated by applying pressure through the window region 184, releasing the securing element that holds the two pieces together.

Snapping the first and second pieces together to from the assembly shown in FIG. 12 causes the securing element to engage and hold the first and second pieces together. The securing element may be disengaged by applying pressure. For purposes of simplicity, in one embodiment, the first and second pieces do not include either a suture or an attachment linkage to the shuttle. It should be understood that these components may be included.

For example, the securing element 183, and the clip 180 as a whole, may be made of a plastic polymeric material, a metal, or the like. Although the latch is shown extending from the first piece 181, it may alternatively extend from the second piece 182. More than one latch may be used. Also, alternative variations of the latch may also be used. The suture 90 and/or linkage 85 may be glued, heat-staked, or otherwise attached permanently or semi-permanently to the second piece 182. In some variations the suture may be knotted. For example, the suture or linkage may be attached to the second piece 182 by first threading the end of the suture through the hollow second piece and then knotting the suture; the larger-diameter knot will be retained by the second piece since the suture knot cannot pass through the tapered or smaller-diameter opening or passage in the second piece. In some variations the second piece may be pre-threaded with a suture.

In use, a surgeon can easily snap the two pieces together, and the assembly may pass through the tissue with minimal drag. As mentioned, the assembly can be separated back into the first and second pieces by releasing the latch, if necessary. The latch may be released manually, or by using a special tool configured to disengage the latch. For example, a disengaging tool may be used to clamp on the assembly in the proper orientation and to apply pressure to release the latch.

In a further embodiment, illustrated in FIG. 13A-B, the clip 280 may be a piece of tubing which has been laser cut to accommodate suture 90 and linkage 85 connections. In one embodiment, clip 280 may be crimped securely to suture at suture-attachment element 286. Linkage 85 may be secured within the laser cut path 287. Additionally, suture 90 may protrude into central region of clip 280 to interact with linkage 85, which may also secure linkage 85 within laser cut path 287. Epoxy, or the link, may also be used to secure linkage in clip 280. The laser cut path 287 need not be formed by a laser, but may be machined in other ways known in the art. Alternative embodiments may exist where the linkage 85 is connected to position 286 and suture is connected to position 287. Additionally, linkage 85 may include a second portion of a suture.

Figure 15:
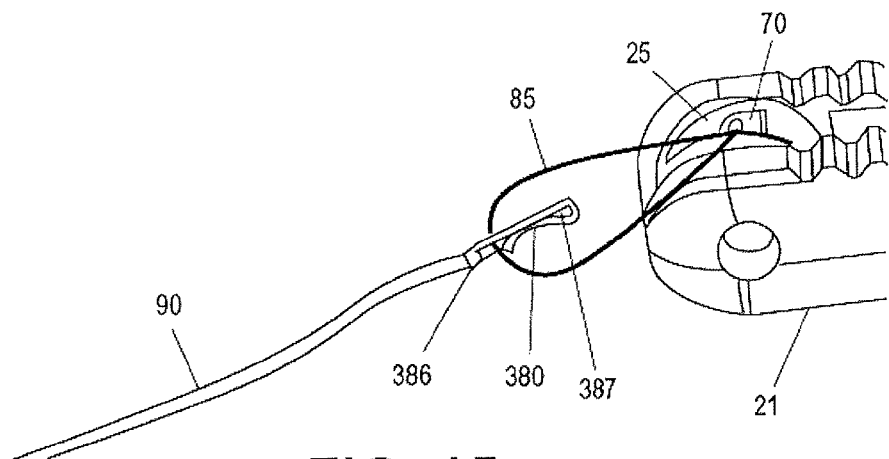
FIG. 15 illustrates the suture clip of FIG. 14 in use with a suture and suture passer device.

In yet another embodiment, the suture clip 380 may include a flexible planar structure that is looped back on itself. This type of clip may be attached to an end of the suture, as illustrated in FIGS. 14-15. One end of the clip, which may include a suture-attachment element 386, may be secured to the end of the suture 90. The suture-attachment element may be crimped to the suture and may be polymeric tubing, such as cyanoacrylate and polyester, for example. The opposite end of the clip may be folded over itself to form a latch 387 within which a suture, wire or the like may be placed. The clip is secured to the suture at the suture-attachment element, and is latched to a wire loop 85 which is attached to the shuttle. Of course, the clip may be reversed such that the clip engages the suture rather than the wire loop. Alternatively, of course, the wire may be replaced by an additional suture or the like.

Figure 16:
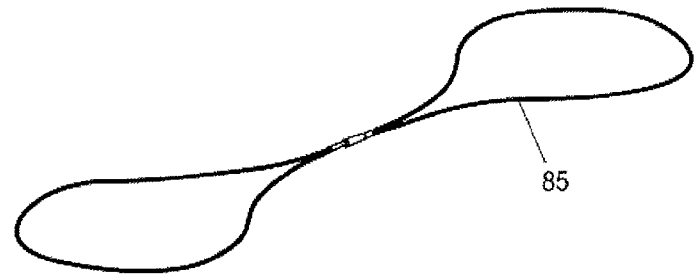
FIG. 16 illustrates another embodiment of a suture linkage wherein the linkage forms a FIG. 8.

In yet another embodiment, illustrated in FIG. 16, the linkage 85 may be a wire loop. The wire may include nitinol. For example, FIG. 16 shows a wire loop linkage 85 bonded in the middle to form a double-loop construction, having at least two loops, or in one embodiment, a "Figure-8" shape. A double-loop or a Figure-8 shape may provide additional safety in that if any portion of the wire loop linkage 85 fails, the linkage remains fixed to at least one of the suture clip 80 or the shuttle 70. Conversely, a wire loop linkage looped through both the clip 80 and shuttle 70, as a mere loop of wire, may fall into the body upon failing. In arthroscopic applications, this may create a dangerous situation for the patient.

A suture passer may also include one or more seating regions for receiving the tissue penetrating member on the opposite jaw from the one from which the tissue penetrating member extends. The seating region may releaseably (and alternatingly) hold and release the shuttle in variations including a shuttle. Thus, a suture passer device 10 may include a seating region 25 into which the tissue penetrator engages. This region may be referred to as a seat, a tissue penetrating engagement region, or a shuttle retainer or shuttle retainer seat. For example, the suture passers described in the U.S. Ser. No. 11/773,338 patent application (previously incorporated by reference) as well as provisional patent application U.S. Ser. No. 60/985,543 (herein incorporated by reference in its entirety) may include a cavity or opening into which a tissue penetrator 50 can be inserted. In these devices a suture shuttle 70 may be passed between the tissue penetrator 50 and the seat 25, although shuttleless variations (as described below) may also include a seat region for engaging the tissue penetrator and suture 90.

Figure 17A:
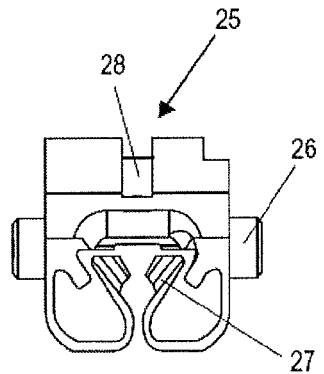
FIGS. 17A-17B illustrates a first embodiment of the shuttle retainer seat.
Figure 17B:
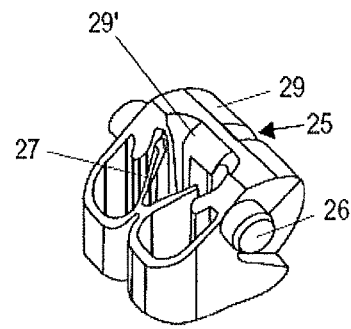
Figure 18:
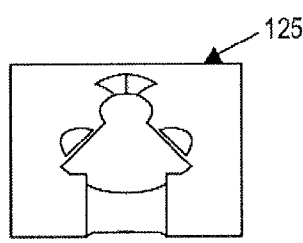
FIG. 18 illustrates a second embodiment of the shuttle retainer seat.
Figure 19:
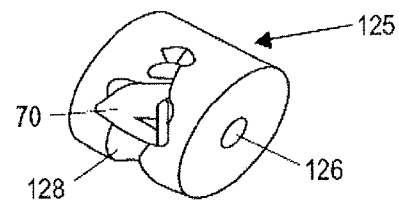
FIG. 19 illustrates one embodiment of the interaction of the suture shuttle and shuttle retainer seat.

FIGS. 17-19 illustrate various embodiments of the shuttle retainer seat 25, 125. The shuttle retainer seat may be positioned with respect to the lower jaw 21, and in one embodiment, within the lower jaw 21 as shown. Hole and pin 126, 26, respectively, may be for the attachment of a stiff member 32' which may rotate the shuttle retainer seat to substantially match the motion, or angle of approach, of the tissue penetrator 50, such that the shuttle retainer seat is moved to substantially match the angle of penetration of the tissue penetrator into the shuttle retainer seat. The amount of motion required may be dependent upon the distance the jaws 20 and 21 are spread apart. Thus, no matter the distance between jaws 20 and 21, the shuttle retainer seat may move complimentary to any direction from which the tissue penetrator 50 is extending from jaw 20 towards jaw 21 and shuttle retainer seat 25, 125. Opening 28, 128 in the suture retaining seat provides a throughway for a set screw or a retaining pin, for example, which may secure the shuttle 70 within the suture retaining seat.

FIG. 19 illustrates, in one embodiment, an example of the interaction of the shuttle 70 and the shuttle retaining seat 125. The shuttle is lodged within the central cavity of shuttle retaining seat. The tissue penetrator may then enter through the central bore of both shuttle and shuttle retainer seat to retrieve the shuttle.

In another embodiment, illustrated in FIGS. 17A-B, the shuttle retainer seat 25 may include flexible seat portions 27, which may contact two sides of shuttle 70, while providing additional clearance for shuttle and tissue penetrator during insertion and removal. The flexible seat portions 27 may provide dynamic clearance for expanding shuttle sides, during release from tissue penetrator 50, thus accommodating shuttle flexure. Further, the device 10 may be more reliable because the flexible seat portions may lessen any effects of high forces during the seating process.

When these devices are used with some tissues, particularly softer tissues, tissue may prolapse into the seat as the tissue is secured between the jaws. This prolapsed tissue may prevent complete penetration by the tissue penetrator, and may also interfere with the operation of the suture passer. In order to prevent the tissue from entering the inner portion of the seat, the shuttle retainer seat 25 may include prominent side walls against which the tissue may be pressed by the collapsing of jaws 20 and 21 around the tissue. The side walls may stretch the tissue, or assist is pulling it taught, to prevent the tissue from prolapsing into the seat where the shuttle is retained. Maintaining pressure on the tissue during puncturing with the tissue penetrator may also form a cleaner cut by the tissue penetrator. These anti-prolapse features may also be incorporated into the non-moving lower jaw component 21 or on the upper jaw 20, rather than on the shuttle retainer seat 25, with spreading features disposed on each side of the shuttle retainer seat.

Figure 20A:
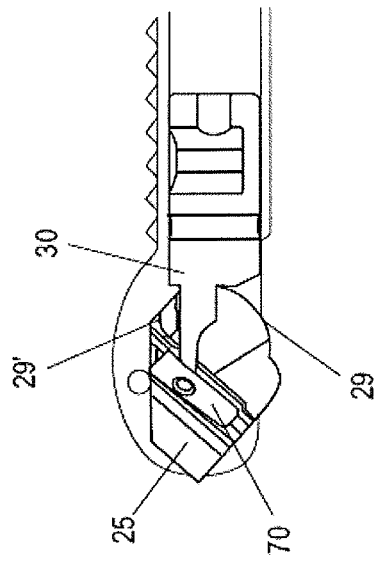
FIGS. 20A-20B illustrate, in cross-section of a lower jaw, one embodiment of the interaction of the suture shuttle, shuttle retainer seat, and a retaining pin.
Figure 20B:
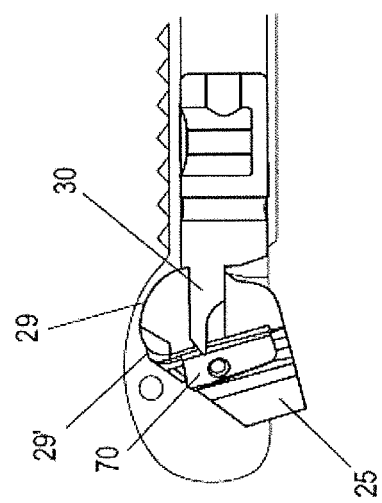

FIGS. 20A-B illustrate one embodiment of the mechanics within lower jaw 21 concerning the shuttle retainer seat 25 and retaining pin 30. As the figures suggest, in one embodiment, shuttle retainer seat 25 may pivot within lower jaw 21, and retaining pin 30 may remain in contact throughout the seat's range of motion.

Retaining pin 30 may be moveable in the forward and rearward direction along its longitudinal axis, and may further be spring loaded to provide a force in at least one of the distal or proximal directions, as required.

Shuttle retainer seat 25 may, in one embodiment, include a cam surface 29 on which retaining pin 30 may at least partially interact. The cam surface 29 may limit retainer pin 30 movement, or depth, into the central bore of seat 25, thereby eliminating interference of retaining pin with tissue penetrator 50. Additionally, cam surface 29 may provide spring loaded rotation of shuttle retainer seat to the position needed to interact with the tissue penetrator. For example, the retaining pin 30 may be adjusted dependent upon the distance the jaws 20, 21 are apart. The adjustment of retaining pin applies a force on the cam surface 29 of seat 25, thereby rotating the seat to the desirable position. In one embodiment, the cam surface 29 may maintain a precise retaining pin protrusion distance into the seat for any seat rotation angle. This may prevent the tissue penetrator from adversely interacting with the pin, aside from any proximal deflection of the retainer pin caused by the tissue penetrator contacting the pin radius 31, as the tissue penetrator enters the seat. Further, a second portion of cam surface 29 (labeled as seat radius 29') may interact with tissue penetrator 50 as tissue penetrator 50 extends into shuttle retainer seat 25. This interaction may provide further alignment of shuttle retainer seat 25 and tissue penetrator 50 for tissue penetrator 50-shuttle 70 interaction.

Additionally, once tissue penetrator 50 exits from shuttle retainer seat 25, seat may return to its original position. This may occur once tissue penetrator terminates contact with seat radius 29', allowing seat to return to its starting position. Upon withdrawal of tissue penetrator, retainer pin 30 returns to its distal position. Retainer pin may then also interact with cam surface 29 to return the seat to its original position.

Figure 21:
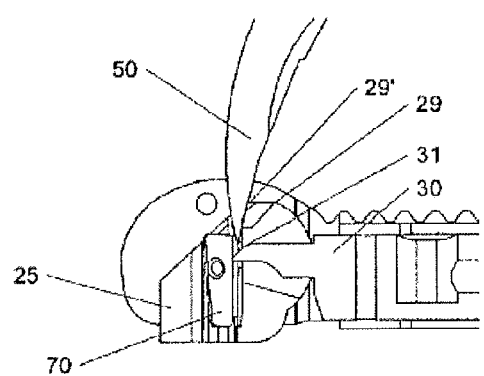
FIG. 21 illustrates, in cross-section of a lower jaw, one embodiment of the interaction of the suture shuttle, shuttle retaining seat, tissue penetrator, and retaining pin.

In a further embodiment, shown in FIG. 21, retainer pin 30 may be considered passive, wherein the spring, which pushes the pin distally, is not displaced dependent upon the other factors, such as the distance between jaws 20 and 21. As such, passive retainer pin 30 is held in a distal position in lower jaw 21, which also therefore holds shuttle retainer seat 25 in a distal position as well. In this embodiment, shuttle retainer seat 25 includes a seat radius 29', which is the radius of a portion of cam surface 29, and retainer pin includes a pin radius 31. Seat radius and pin radius may interact with tissue penetrator 50 upon extension of tissue penetrator from upper jaw 20 towards lower jaw 21. As tissue penetrator 50 comes into contact with shuttle retainer seat 25, it may contact both seat radius 29' and pin radius 31, thereby rotating seat 25 to the desired position (which is dependent upon tissue penetrator angle of entry, which is dependent upon the distance between the jaws), for tissue penetrator entry and collection of shuttle 70. Similarly, the entry of tissue penetrator, upon contact pin radius 31, pushes against pin 30 and pushes pin, against its spring force, in the proximal direction. In this embodiment, the lower jaw 21 mechanics are passive, and are adjusted to proper angles and positions by the tissue penetrator contacting the pin and seat radii to create the adjustment necessary for proper tissue penetrator—seat alignment for precise collection of shuttle 70.

Figure 22:
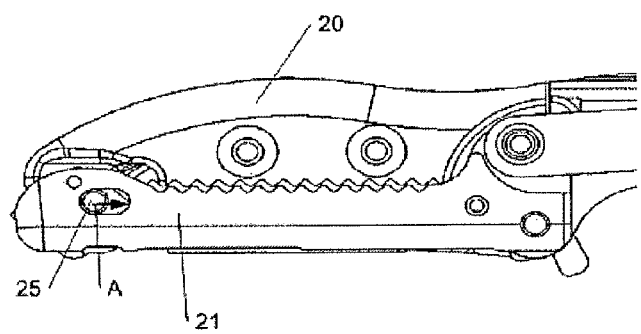
FIG. 22 illustrates a further embodiment of a shuttle retainer seat within the jaw.

In yet another embodiment, FIG. 22 illustrates a shuttle retainer seat 25 which may include a further degree-of-freedom aside from the aforementioned rotational degree-of-freedom. In one example, seat 25 may have a translational movement in the distal-proximal direction through at least a portion of the longitudinal length of lower jaw 21. Arrow A illustrates the translational motion in the proximal direction, from the initial distal position of seat 25. This added degree-of-freedom may provide further optimal alignment of seat with respect to tissue penetrator 50. Further, it may provide a more compliant landing area for tissue penetrator, accommodating any tissue penetrator targeting errors which may occur. As such, seat 25 is not constrained to its exact mounting location on lower jaw 21.

Figure 23:
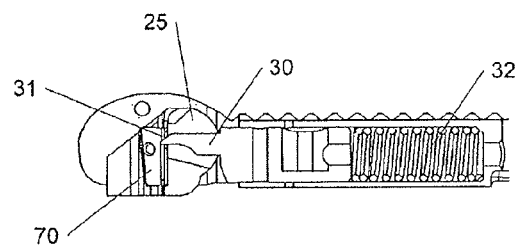
FIG. 23 illustrates, in cross-section of a lower jaw, one embodiment of a retaining pin, including a spring.

FIG. 23 illustrates a first embodiment of the initial set-up of suture passer device 10, prior to use. In this example, shuttle 70 may be initially positioned within shuttle retainer seat 25. Shuttle retainer seat may include a stop within its core to regulate the depth to which shuttle 70 may be positioned. Also, since inner core of seat 25 may be tapered, the stop would prevent jamming of the shuttle 70 within the taper. Spring 32 of retainer pin 30 may be used to preload shuttle 70. As shuttle is inserted into seat 25, retainer pin 30 moves proximally as shuttle engages pin radius 31. Once the shuttle is in place, retainer pin 30, through a force from spring 32, returns to its distal position. In this position, retainer pin 30 may pass through a U-shaped notch 76 on shuttle 70 (see FIG. 24), thereby securing shuttle within seat 25. Upon retainer pin 30 returning to its distal position, spring 32 illustrates its function in lower jaw 21. For example, in one embodiment, the spring's 32 distal force has several functions including, but not limited to: pushing retainer pin 30 distally to capture shuttle, pushing the seat distally into a receptive position for tissue penetrator insertion, providing rotational torque to rotate seat into an optimal angle for tissue penetrator insertion based on the interaction of cam surface 29 and retainer pin 30.

Figure 24:
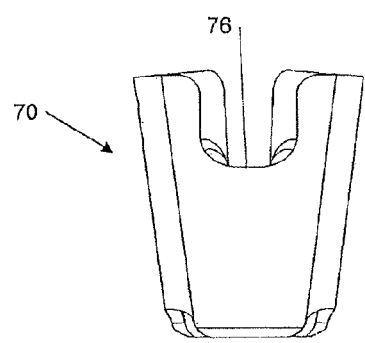
FIG. 24 illustrates another embodiment of a suture shuttle.
Figure 25:
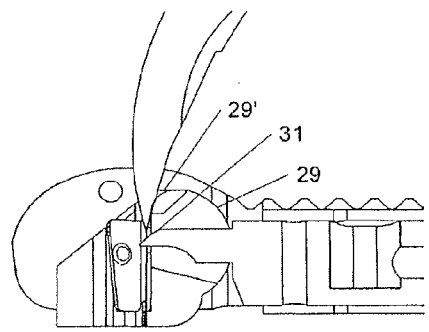
FIG. 25 is a close-up cross-section illustrating the interaction of a retaining pin, shuttle retainer seat, tissue penetrator and lower jaw.

FIGS. 24 and 25 further illustrate the interaction of shuttle 70 and retaining pin 30 in this embodiment. The U-shaped notch 76 is similar to the oval slot, or opening, 174 and 274 of other shuttle embodiments (see FIGS. 6B and 7). However, unlike the oval slot, the U-shaped notch, of one embodiment, provides easier access into the area by the tissue penetrator, as well as allowing tissue penetrator to rotate seat 25 without portions of shuttle 70 interfering with process.

Similarly, in one embodiment, when shuttle 70 is located on tissue penetrator 50, and tissue penetrator 50 extends from upper jaw 20 towards lower jaw 21 and seat 25, the tip of tissue penetrator acts on seat and retainer pin 30 in much the same way as when shuttle is located within seat 25. Therefore, as tissue penetrator 50 moves into the central bore of seat 25, the tip of tissue penetrator 50 engages the seat radius and pin radius 29' and 31 which may properly align seat 25 with tissue penetrator 50, as well as push retainer pin 30 proximally and away from seat 25. Once tissue penetrator 50 is extended fully into seat 25, shuttle 70 may be within seat as well, and may further be in the proper position within seat for securing itself therein. Thus, retainer pin 30 may move distally once the U-shaped notch 76 passes through the longitudinal path of retainer pin 30. As retainer pin 30 moves distally, it may pass at least partially through U-shaped notch, thereby securing shuttle 70 within seat 25. The tissue penetrator 50 may then be retracted, leaving shuttle 70 within seat 25. Tissue penetrator 50 may then extend once again into seat 25 to collect shuttle 70, in which the reverse occurs and tissue penetrator 50 pushes retainer pin 30 proximally and shuttle 70 may then be collected.

Figure 26:
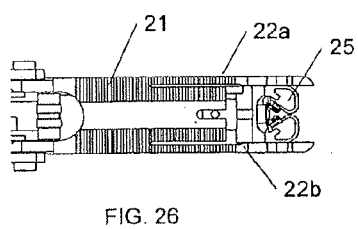
FIG. 26 is a top plan view of one embodiment of a lower jaw and shuttle retainer seat.
Figure 27:
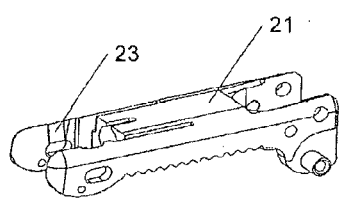
FIG. 27 is a perspective view of a further embodiment of a lower jaw.

In one embodiment, shuttle retainer seat 25 may be press-fit into lower jaw 21. In a first example, as shown in FIG. 26, lower jaw 21 may include flexible side members 22 a and b, which flex as shuttle retainer seat 25 is inserted into place. Once in place, flexible side members 22 a and b return to their original position, securing seat in between them. As such, flexible side members may include a groove on the inner surfaces, or the like, so that the inner width in between the flexible side members is wider than on the edges. In a second example, as in FIG. 27, the side members of lower jaw 21 may include a tapered lead-in element 23 such that seat may be wedged within the taper. Other similar features may also be used to secure seat within lower jaw member 21.

Figure 28:
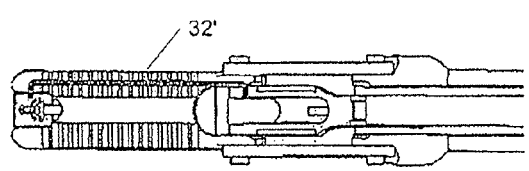
FIG. 28 illustrates a top plan view of a lower jaw wherein one embodiment of the shuttle retainer seat and stiff member is positioned.

In an alternative embodiment, in FIG. 28, shuttle retainer seat 25 may instead be controlled by a stiff member 32'. Stiff member 32' may rotate shuttle retainer seat, as the upper and lower jaws 20 and 21 move relative to one another, to maintain the proper angle with the tissue penetrator. The stiff member 32' is controlled via mechanisms in the actuator 15 of device 10 to ensure proper alignment.

Figure 29A:
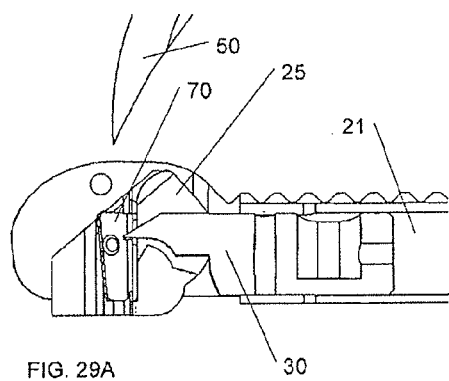
FIGS. 29A-29K illustrate an embodiment of the interaction of the shuttle, shuttle retainer seat, retainer pin and tissue penetrator as the shuttle is passed between the shuttle retainer seat, the tissue penetrator, and back again.
Figure 29B:
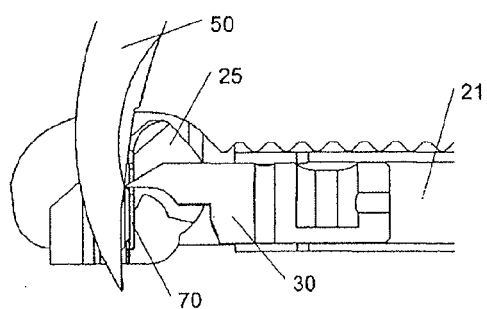

FIGS. 29A-29K illustrate cross-sectional views of one embodiment of the interaction of shuttle 70, shuttle retainer seat 25, retainer pin 30 and tissue penetrator 50 at lower jaw 21. Many of the operations discussed above would be used in this illustrated series of actions. In FIG. 29A, shuttle 70 may be secured within shuttle retainer seat 25 by retainer pin 30 in lower jaw 21. Tissue penetrator 50 is shown to be above lower jaw 21. In FIG. 29B, tissue penetrator 50 may pass through shuttle retainer seat 25, where shuttle 70 may be located, and may push retainer pin 30 proximally. As discussed earlier, the shuttle retainer seat 25 may be movable to accommodate the entry angle of tissue penetrator 50.

Figure 29C:
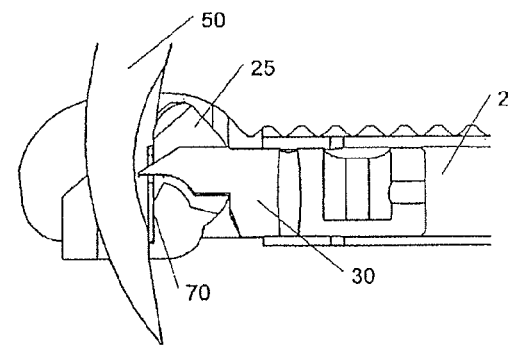
Figure 29D:
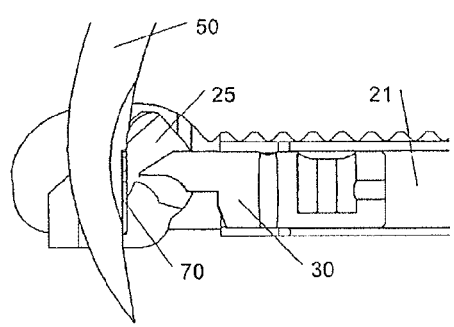
Figure 29E:
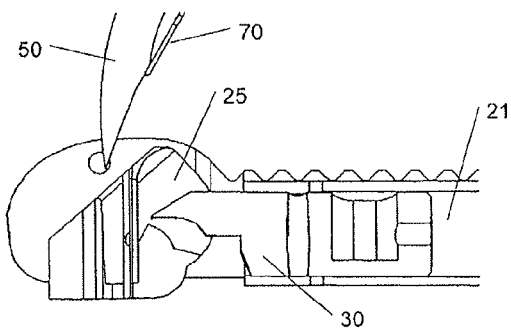

In FIG. 29C, tissue penetrator 50 may extend fully into shuttle retainer seat 25, engaging the shuttle 70. Retainer pin 30 may move distally again, back to its original position, and into groove on the back portion of the tissue penetrator (as well as through the U-shaped portion of the shuttle 70, not shown), due to the spring force pushing the retainer pin distally. FIG. 29D illustrates the retainer pin 30 being manually retracted proximally, through use of the actuator 15 (discussed below), to disengage the retainer pin from the shuttle 70. In FIG. 29E, the tissue penetrator 50, with shuttle 70 engaged, may be retracted out of the lower jaw 21 and back towards upper jaw 20. The shuttle 70 may be removed from the shuttle retainer seat 25 when the retainer pin 30 is retracted proximally, as shown. FIGS. 29A-29E illustrates one example of the tissue penetrator 50 engaging shuttle 70, located in the shuttle retainer seat 25, and retracting shuttle 70 up to upper jaw 20.

Figure 29F:
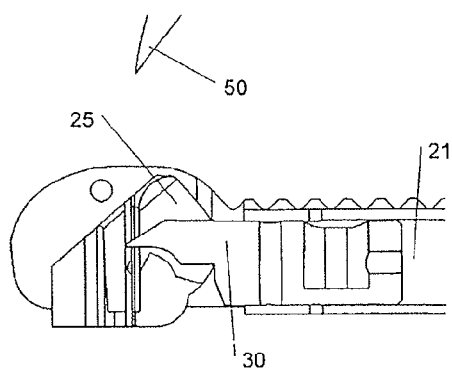

In FIG. 29F, the tissue penetrator 50, with engaged shuttle 70, may be retracted back to upper jaw 20, and actuator 15 is released such that retainer pin 30 may move back to its original, distally located, position. This may be considered to be one pass of the shuttle 70, which may have suture and/or suture clip attached.

Figure 29G:
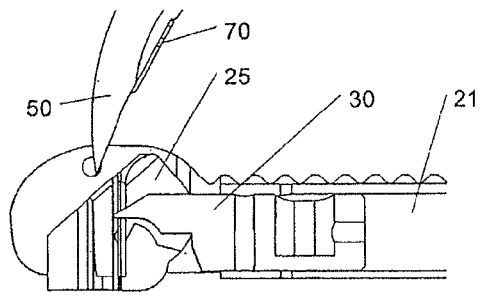

In FIGS. 29G-29K, an example of a second pass is illustrated where the shuttle is passed from the tissue penetrator 50 to the shuttle retainer seat. In FIG. 29G, the tissue penetrator is extended from upper jaw 20 towards lower jaw 21. Shuttle 70 may be engaged on tissue penetrator 50. Retainer pin 30 may be in a distal position.

Figure 29H:
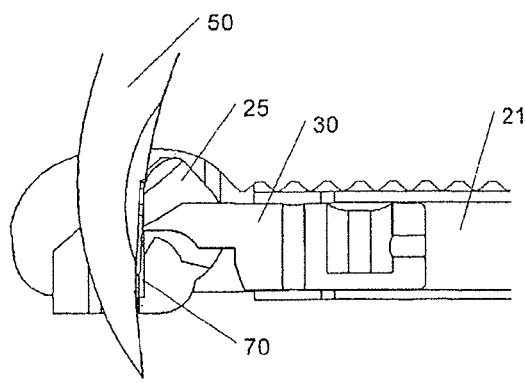
Figure 29I:
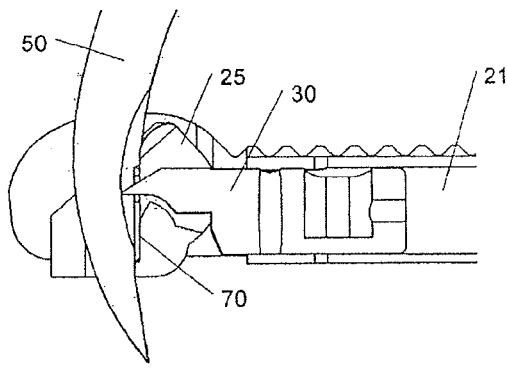

In FIG. 29H, the tissue penetrator 50 and engaged shuttle 70 enter into shuttle retainer seat 25. Retainer pin 30 may be pushed proximally by the tissue penetrator 50 and/or engaged shuttle 70. In FIG. 29H, the tissue penetrator 50 may be extended completely such that retainer pin 30 may return to a distal position, thereby passing through, for example, the U-shaped opening (not shown) on shuttle 70 and the groove within tissue penetrator 50. Shuttle 70 may now be secured within shuttle retainer seat 25, and may even still be engaged on tissue penetrator 50.

Figure 29J:
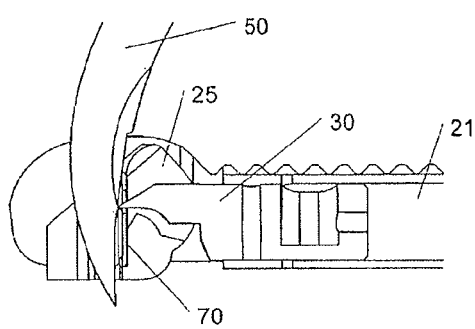
Figure 29K:
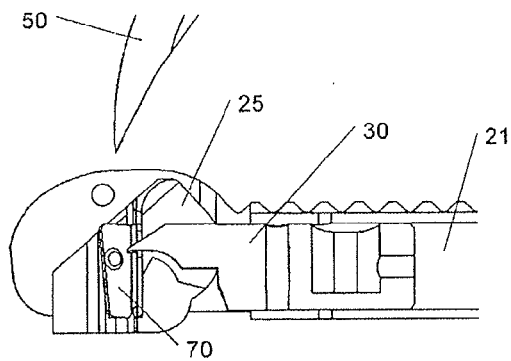

FIG. 29J illustrates tissue penetrator 50 retracting from shuttle retainer seat 25 and lower jaw 21. Retainer pin 30, though pushed proximally, once again, by the movement of tissue penetrator 50, the spring (not shown) within retainer pin 30 may still be sufficient to maintain the retainer pin 30 in a position as distal as possible such that shuttle 70 may still be retained within shuttle retainer seat 25 by retainer pin 30. The force on the shuttle 70, applied by retainer pin 30, and against the movement of tissue penetrator 50, may cause a retaining structure, such as the dimple/divot structures discussed above, to disengage such that tissue penetrator and shuttle disengage from each other. Shuttle 70 is thus retained within shuttle retainer seat 25. In FIG. 29K, the tissue penetrator 50 may retract completely away from shuttle retainer seat 25, and retainer pin 30 may then move distally to return to its original position. Shuttle 70 is therefore secured within shuttle retainer seat 25 by retaining pin 30. Tissue penetrator 50 may retract completely back to upper jaw 20.

Thus FIGS. 29A-29K illustrate one embodiment of the interaction of the tissue penetrator 50, shuttle 70, shuttle retainer seat 25 and retainer pin 30. This interaction may include the various mechanisms, structures and operations discussed throughout. The jaws 20 and 21 can be moved totally independently of the tissue penetrator 50. The jaws may be used to grasp and manipulate tissue prior to suture passage. As described below, since the tissue penetrator and jaws operate independently of one another, the jaws may be used as graspers without having to expose the tissue penetrator.

Figure 30A:
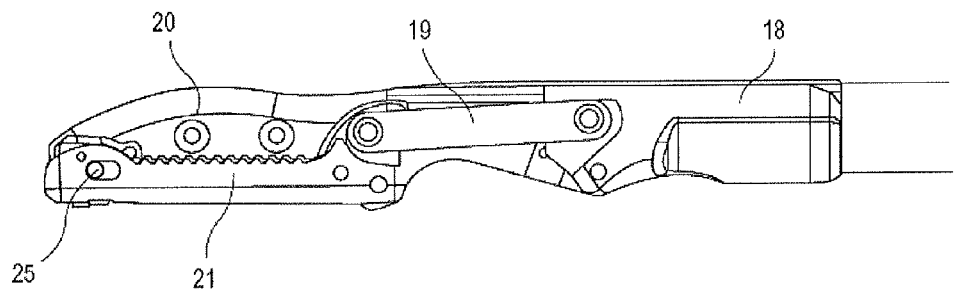
FIGS. 30A-30B illustrate one embodiment of a distal portion of a suture passer device including first and second jaws.
Figure 30B:
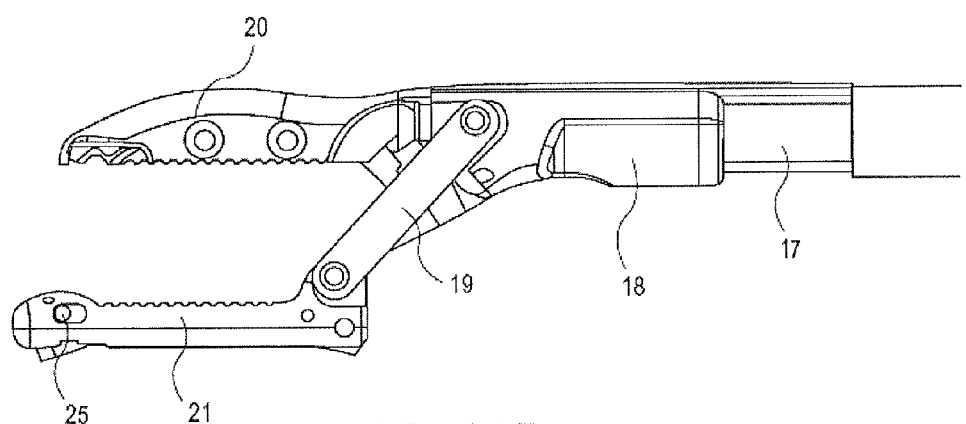

In one embodiment, the upper and lower jaws 20 and 21 may move kinematically in that they may remain substantially parallel to one another when the lower jaw is brought away from the upper jaw. For example, in FIGS. 30A-B, illustrating one embodiment, lower jaw is pivotally attached to pivot arm 19. Pivot arm 19 is then attached to sliding element 18 which may slide along the outer surface of shaft 17. In this example, when lower jaw is moved away from upper jaw, sliding element 18 moves distally along shaft 17 such that lower jaw may remain parallel to upper jaw. This sliding movement compensates for the tracking error of the pivot arm, also known as a 4-bar linkage, such that the lower jaw may track the arc traversed by the tissue penetrator 50. Additionally, this movement of the sliding element 18 allows the lower jaw 21 to remain substantially directly opposite the upper jaw 20 throughout the range of motion of the lower jaw. As a further example, if the lower jaw were not attached to the sliding element, the lower jaw, as it moves away from the upper jaw, would also move proximally, relative to the upper jaw, and thus be out of alignment with upper jaw.

Aside from the sliding pivot arm example above, other mechanisms such as, for example, gear drives, linkages, cable drives, and the like, may be used to ensure proper alignment of top and bottom jaws 20 and 21 during jaw actuation. The upper jaw 20 may be fixed in place as to shaft 17. The fixed upper jaw may provide many advantages to a moveable upper jaw, such as providing a reference point for the surgeon, allowing for independent adjustability of the jaws and tissue penetrator engagement position, and the like. The parallel relationship of the upper and lower jaws 20 and 21 of this embodiment allow for easier manipulation of tissue, while also preventing the jaws from overly impinging any portion of the tissue. For example, if the jaws opened as a typical V-shaped pattern, then the proximal tissue, deeper into the V shape, would have excess force on it than the distal portion of the tissue, within the jaws. The parallel relationship ensures that the force of the jaws is spread equally throughout the tissue in between the jaws.

Figure 31:
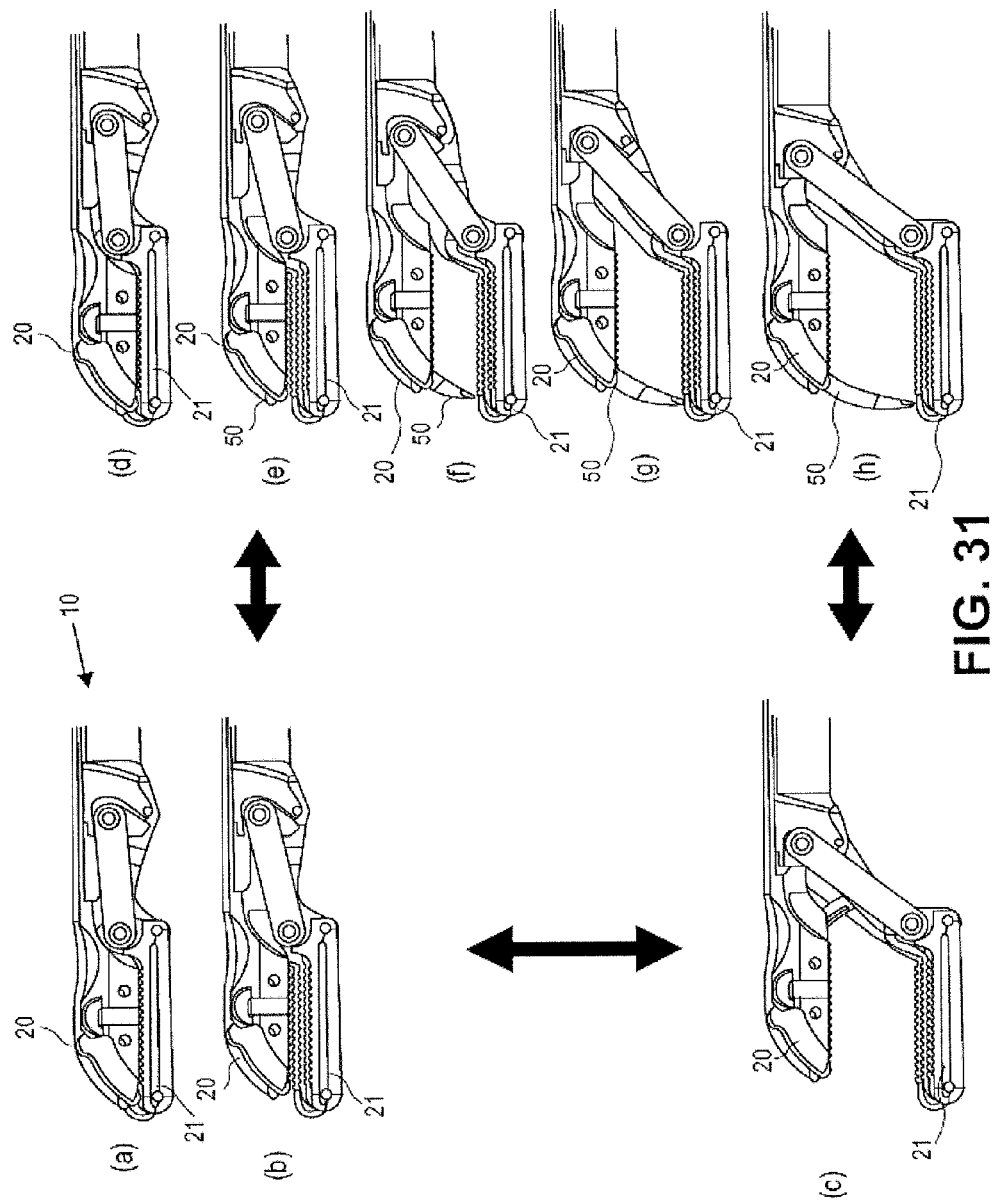
FIG. 31 illustrates another embodiment of a distal portion of a suture passer device.

In an alternative embodiment, the upper jaw 20 may slide distally and proximally, while the attachment point of pivot arm 17 remains stationary. Thus, as the lower jaw moves away from the upper jaw, the upper jaw moves proximally to maintain alignment with the lower jaw. FIGS. 31 and 32A-C illustrate this embodiment. Also illustrated in FIG. 31 are the various entry angles of the tissue penetrator when the upper and lower jaws are at various distances from one another.

Figure 32A:
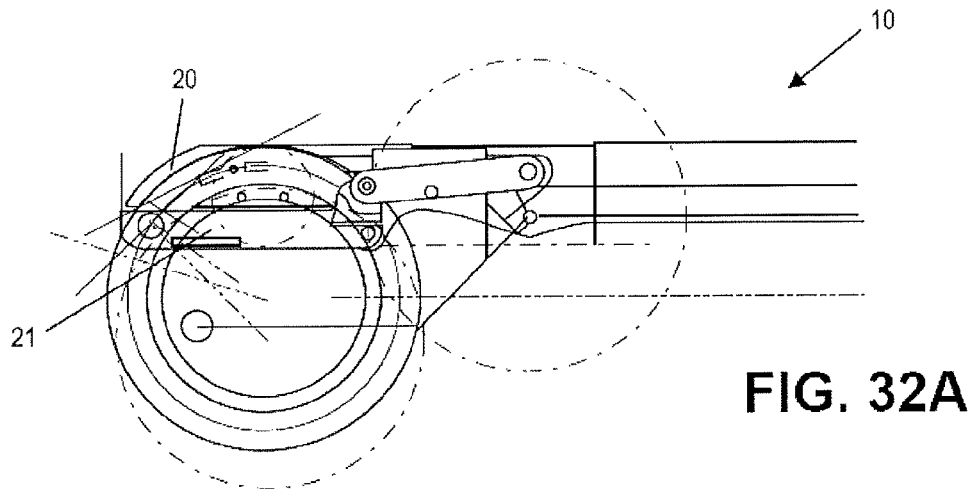
FIGS. 32A-32C show yet another embodiment of a distal portion of a suture passer device.
Figure 32B:
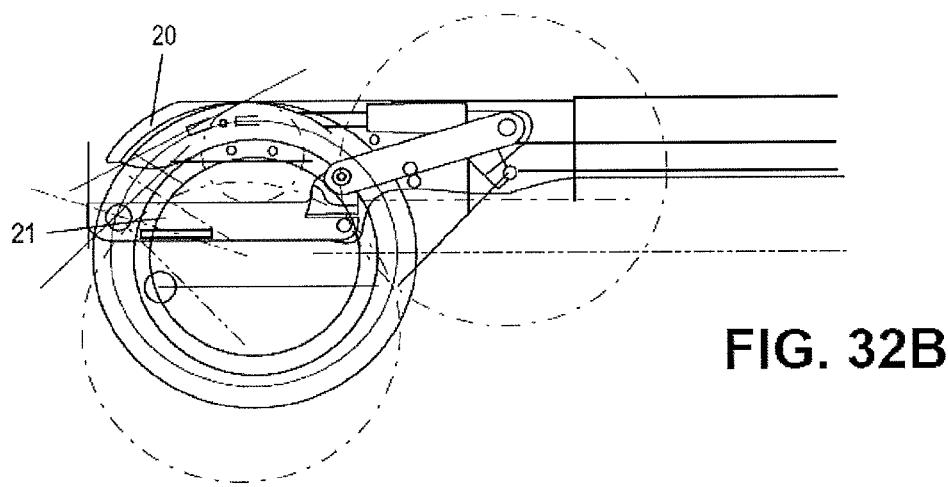
Figure 32C:
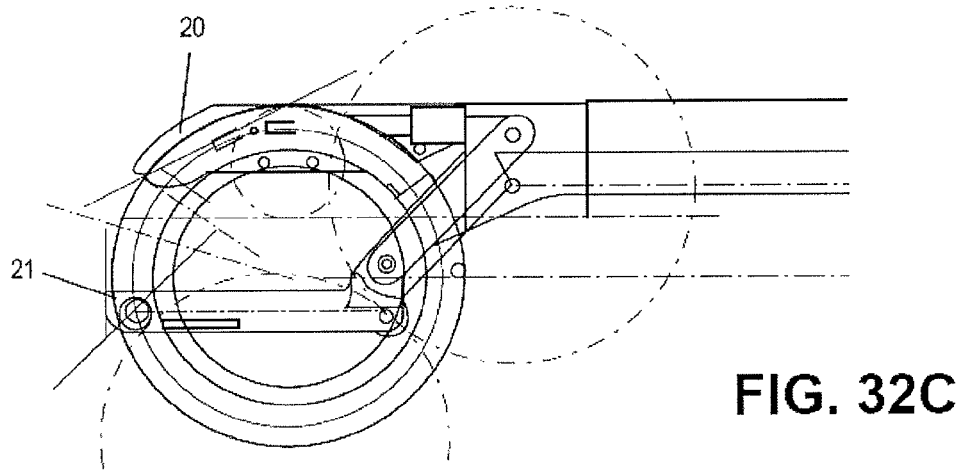

For example, the tissue penetrator will meet the shuttle retainer seat, located in the lower jaw, no matter the separation between the upper and lower jaws. Thus, the jaws may be clamped to tissue of any depth, and the tissue penetrator will pass through the tissue and hit the lower jaw directly at the shuttle retainer seat. For example, in FIG. 31, upper and lower jaws 20 and 21 may have an initial position (a). The expansion of the jaws, illustrated by positions (a)-(c), may occur by the lower jaw 21 pivoting away from upper 20, while upper jaw 20 slides proximally to maintain a functional relationship between the jaws as the lower jaw 21 pivots. FIG. 31 also illustrates the extension of tissue penetrator 50 from the upper jaw 20 to the lower 21, in positions (a) and (b) to (d) and (e). Positions (d)-(h) of FIG. 31 illustrate a further method wherein the simultaneous expansion of jaws 20 and 21 and extension of tissue penetrator 50 may occur. Additionally, FIG. 31 illustrates in positions (c) to (h), the extension of the tissue penetrator 50 when jaws 20 and 21 are expanded. As such, FIG. 31 illustrates one embodiment of the device 10 in which the lower jaw 21 may track the arcuate path of tissue penetrator 50, such that tissue penetrator 50 may engage the lower jaw 21 at the substantially same position regardless of the position of the lower jaw 21. FIGS. 32A-C further illustrate the arcuate path the lower jaw 21 may travel.

Figure 33:
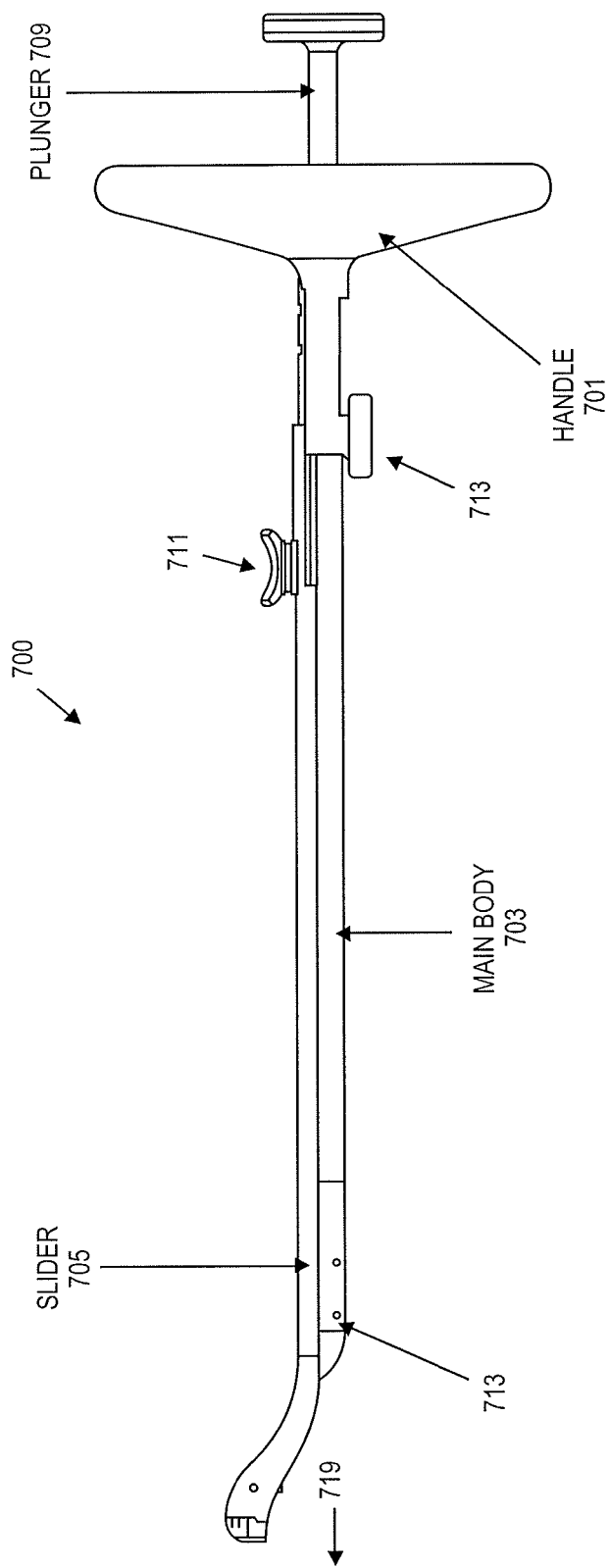
FIG. 33 illustrates another embodiment of a suture passer.

Referring to FIG. 33, in another embodiment, a suture passer 700 includes an elongate main body 703 extending the length of the device. The proximal end of the device 700 includes a handle 701. The distal end of the main body 703 of the device may be referred to as a first arm forming the distal end of the device. A slider 705 is movably coupled to the main body. The distal end of the slider 705 forms the second (e.g., "upper") arm. Sliding the slider 705 proximally relative to the first arm (and main body 703) will result in the formation of an angled opening. The opening is roughly V-shaped, in which one side is substantially flat while the other side is angled relative to the flat side.

Figure 7:
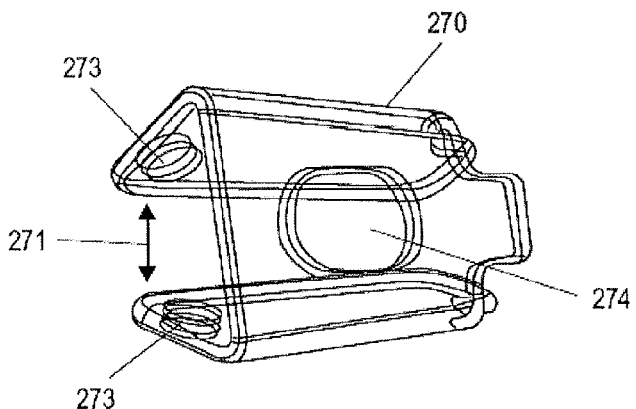
FIG. 7 illustrates yet another embodiment of the suture shuttle.
Figure 8:
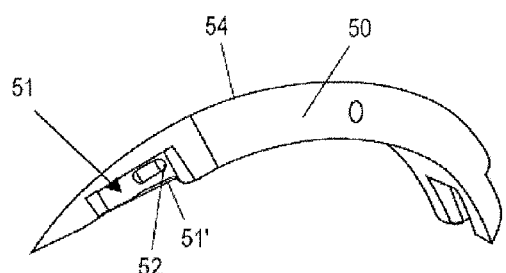
FIG. 8 illustrates one embodiment of a tissue penetrator.

In FIG. 7, the distal end of the slider is rounded or blunted to prevent damage to the meniscus when operating the device. In some variations the distal end of the slider (angled or second arm) may be enlarged relative to the more proximal region of the slider. The slider may also include a slider control (e.g., finger control 711) which may be manipulated manually or automatically to move the slider distally or proximally. A similar control on the opposite side (e.g., on the main body) may also be included to slide the first arm (the main body) relative to the slider when it is desirable to hold the slider in a fixed position relative to the patient, for example.

One or more arms of the suture passer may be bent or curved. In the example shown in FIG. 7, the second (slider) arm of the device is bent or angled "upwards" away from the first arm, or from the long axis of the device, including the first arm, so that the ends region of the second arm (the upper arm) relative to the long axis is bent at approximately the angle formed by the superior surface of a meniscus relative to the inferior surface of the meniscus. The angle may be fixed (e.g., at an acute angle of approximately 10°, 15°, 20°, 25°, 30°, 35°, 40°, 45°, 60°, etc. including any angle between 1° and 90°); for example, the angle may be between 20 degrees and 50 degrees. In some variations, the angle between the first and second arms is variable. In some variations the angle is adjustable (e.g., either or both arms may be bent or adjusted to adjust the angle there between). The angle of the bend in the upper (second) arm may be approximately the average angle between the superior and inferior faces of the meniscus; for example, the angle may be approximately 35 degrees ±2 degrees, ±5 degrees, ±7 degrees, ±10 degrees, ±15 degrees, etc. In general the bend forms an acute angle with the lower (second) arm when the second arm is extended distally. In some variations, as mentioned, the distal end region of the second arm may be bendable from a straight or pre-bent configuration into the final bend configuration.

In the variation shown in FIG. 7, a tissue penetrator is housed within the first arm 713, which in this example is integral with the main body 703. In FIG. 7, the first arm extends distally, in-line with the proximal-distal axis of the elongate main body; in some variations the first arm is separate from the main body, but extends in parallel with the distal/proximal axis of the main elongate body of the device. A second, bent arm formed by the slider 705 may include one or more shuttle docks. The second arm may also be referred to as the slider, since it is slideably coupled with the elongate body (e.g., main body) and/or the first arm of the device. As shown in FIG. 7, the distal end of the second arm extends at an angle from the main body. In this example, the angle is not constant over the entire length, as the distal tip of the second arm is rounded (having a region almost in parallel with the long axis of the elongate body and first arm). When the second arm is retracted relative to the first arm (or, relative to the second arm, when the first arm is extended) an acute-angled, distal-facing 719 opening is formed between the first arm and the second arm which may be positioned around the apical region of a meniscus, e.g., the tapered region opposite from the capsular region.

In the exemplary device shown in FIG. 7 the second, upper arm (slider) include one or more seats or docks (e.g., shuttle dock) for holding a suturing element within the second arm. The device of FIG. 7 is configured to have two docks. One of these docks may be configured as release dock which may hold the suturing element (e.g., suture, suture shuttle and/or lead wire) within the dock and release the suturing element from the dock to engage the tissue penetrator; the second dock may be identical to the first dock, or it may be configured as a holding dock that is configured to receive the suturing element from the tissue penetrator but not release it back to the tissue penetrator. The first dock and the second dock may be separated from each other along the length of the second arm. For example, in some variations a release dock is located near the distal tip of the second arm and a holding dock is located proximal to the release dock. In some variations these positions are reversed. In some variations the second arm includes more than two docks. The release dock may be pre-loaded with a suturing element.

The shuttle dock may be configured to releasably engage a suture shuttle (or other suturing element). The suture shuttle may be passed between a shuttle dock and the tissue penetrating element that may extend between the first and second arms. For example, the suture passer 700 can be used to repair a torn meniscus. A tissue penetrator may extend from within a first arm, though the meniscus tissue, and engage a suture shuttle held in a dock in the second arm; the tissue penetrator with attached shuttle may then retract back through the tissue to the first arm. If a pull wire and/or suture is attached to the shuttle, the distal end of the pull wire and/or suture will be pulled back from the second arm to the first arm. Thereafter, the first arm may be retracted proximally relative to the second arm, or the device may be otherwise repositioned on the meniscus (without requiring that the device be removed from the meniscus). The tissue penetrator may then be passed back through the tissue to engage either another shuttle dock, or the same (first) shuttle dock, and release the suture shuttle within this dock; the tissue penetrator may again be withdrawn, leaving the suture and/or lead wire stitched through the meniscus from a first (e.g., superior) surface of the meniscus to an opposite (e.g., inferior) surface of the meniscus and back to the first surface of the meniscus. Additional stitches may be made, or the device may be withdrawn from the knee and the suture pulled taut and secured in position.

Additional suture passer embodiments are described in U.S. Patent Application No. 61/483,200, previously incorporated by reference. The size of the suture passer device 10 may be any size useful in performing surgery on the body. For example, for many arthroscopic joint surgeries, the upper and lower jaws may be around 16 mm in length, though a length of up to about 25 mm is obtainable. This may be significantly scaled down for a device for use in, for example, wrist surgery. Alternatively, a larger device, with larger jaws, may be useful for hip or torso surgery.

In further examples, the suture passer device may, for example, be able to pass suture through any tissue up to about 10 mm, though a scaled up version of the device may allow for greater amounts of tissue. Moreover, in most embodiments, the device may pass through a standard 8 mm cannula.

Zip/Pull Wire

In any of the variations described herein, a pull wire may be used to suture the tissue. The pull wire may also be referred to as a zip wire, a pull loop, a leash, a lead, a tether, or the like. In general, the pull wire is typically a thin, flexible wire-like element that may be drawn through the tissue by the suture passer in a suture pattern. For example, the pull wire used may be a small diameter wire/cable. The smaller diameter wire will take much less force that a larger diameter suture to be stitched and may exert minimal forces on the shuttle.

In some variations, the pull wire is made from stainless steel cable (e.g., 19 strands wound together as 1). This configuration may allow a great deal of flexibility and may also allow the pull wire to be welded to a stainless steel shuttle. In some variations the pull wire is made from a single wire or several other cable configurations. It can also be made of any other appropriate material, such as nickel titanium (e.g., Nitinol), elgiloy, polymeric materials, etc.

In some variations, the pull wire can also be coated (i.e., with PTFE) to prevent tissue damage as it is pulled through tissue.

Figure 34:
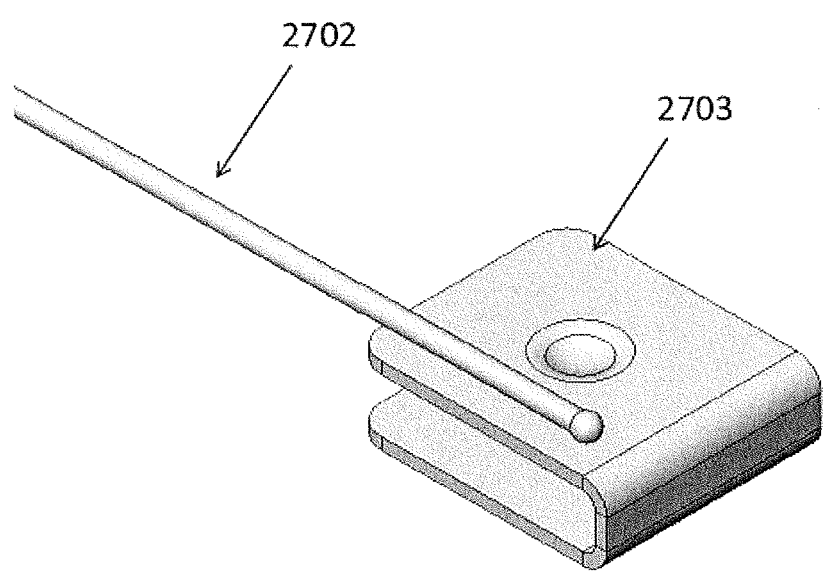
FIG. 34 is another variation of a suture shuttle including a pull wire

FIG. 34 illustrates one variation of the distal end of a pull wire 2702 that has been attached to a suture shuttle, as described above. In this example, the pull wire 2702 has been welded to a shuttle 2703. Another example of a pull wire is shown in FIG. 35, including exemplary dimensions. In FIG. 35, the pull wire 2801 is coupled to a shuttle 2803 at its distal end and extends for some length (e.g., approximately 10 inches, though shorter or longer wires may also be used). The proximal end of the pull wire forms a loop 2805 through which a suture 2807 may be threaded either before or after the shuttle and pull wire have been passed through the tissue. The proximal end of the pull wire in this example is looped onto itself and held by heat shrink tubing 2811; any appropriate method of forming a loop or suture attachment site (including non-loop attachment sites, such as clips, clamps, adhesives, splicing, etc.) may be used.

FIGS. 36A and 36B illustrate another variation of pull wires as described herein. In FIG. 36A the pull wire forms a loop; in this example, the loop may be biased to open as shown, making it easy to load a suture on the pull wire after or before it has been passed through the tissue. This may be particularly beneficial when loading the pull wire with the suture from within the tissue (e.g., within the knee), for example, arthroscopically. In FIG. 36B, the pull wire includes a smaller loop region. In both of these examples, the pull wire is shown attached to a suture shuttle.

The devices and systems described herein may be adapted for use with a pull wire. For example the device may include structures to manage or control the pull wire. For example, the seat/dock may be adapted to allow a pull wire to extend out of the seat. FIG. 37A shows another variation of an upper arm of a suture passer including a pair of docks for receiving a suturing element which may include a pull wire. In FIG. 37A, the upper arm includes a cut-out channel 3003 in the lateral side of the arm to allow a pull wire to extend from the upper arm. Similarly, the opposite arm, from which a tissue penetrator extends and retracts, may be adapted to allow the lead wire to extend from the device without interfering with the activity of the suture passer. FIG. 37B shows an enlarged view of a portion of the lower arm including a tissue penetrator 3004 retracted into the lower arm 3006. The tissue penetrator includes a suture shuttle coupled to a pull wire 3012, and the pull wire extends from a channel 3008 in the lower arm. Various configurations of suture passers are further described in Loading the Suture within the Suture Passer while in Tissue The suture passer jaws may lock so that tissue can be secured between them, and the suture can be passed by means of a tissue penetrator that carries the suture, which may be attached to suture shuttle, between the two jaws. In particular, these methods may be performed using a device that is configured to pass the suture between the jaws regardless of the position of the jaws relative to each other, and thus the jaws are not required to be in a particular position in order to pass the suture therebetween.

Many of the continuous suture passers described above are configured so that the tissue penetrating member (e.g., needle element) may be completely retracted into the device during operation, preventing damage to tissue. In general, this may mean that the distal end (the leading end) of the tissue penetrating member may be withdrawn completely into the jaw of the continuous suture passer from which it may be extended. Thus, this jaw may have a substantially flat (atraumatic) surface for contacting tissue when the tissue penetrating member is completely retracted. Many of these continuous suture passers may therefore be used as a clamp or grasper when the tissue penetrating member is completely retracted. In some variations, using the device when the tissue penetrating member is partially extended may allow the device to be operated to cut tissue (via the tissue penetrating member).

Any of the continuous suture passers described herein may be used to form one or more complex suture patterns in tissue. Because these devices may be used to pass a suture (continuously, without requiring withdrawal of the device from the tissue to reload the suture), they may be used to stitch or perform a procedure having a complex suture stitching pattern that requires passing the suture through a tissue in multiple directions (e.g., first up through the tissue, then down through the tissue).

Figure 38A:
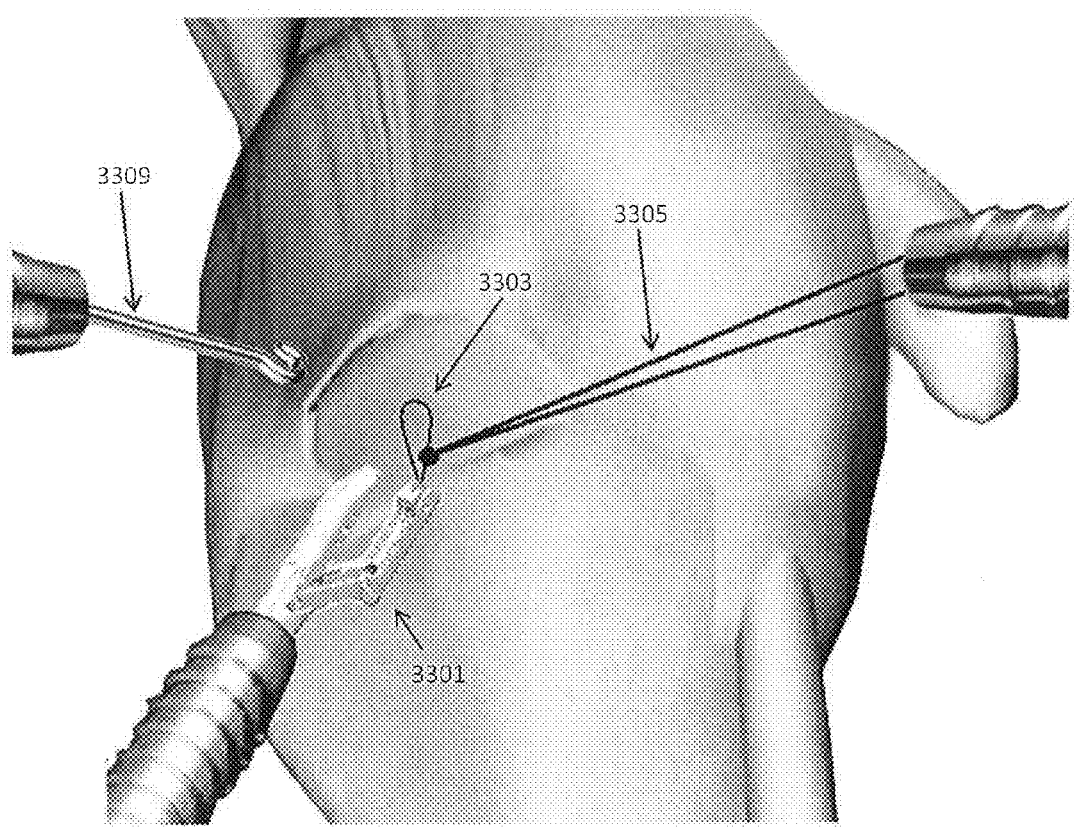
FIGS. 38A-38G illustrate one example of a method of passing a suture that allow loading/unloading of the suture within the tissue, and passage of the suture (continuously) through the tissues.

FIGS. 38A to 38G illustrate some of the steps of passing a loading a suture passer while within the tissue and operating the suture passer to suture tissue without requiring the device to be withdrawn from the tissue. Thus, the suture passer can be loaded with a suture while both a portion of the suture passer and the suture are within the tissue, e.g., the loading can be performed percutaneously For example, FIG. 38A shows a suture passer 3301 similar to those described above, having two opposing jaws, a tissue penetrator that extends from within one jaw and across the space between the jaws to engage the opposite jaw, and a suture shuttle that alternately couples to the tissue penetrator and the opposite jaw. The suture shuttle includes a loop 3303, such as a pullwire loop as discussed above, extending from the shuttle body. The suture 3305 can then placed in the tissue. In some embodiments, as shown in FIG. 38A, the suture 3305 can be anchored to the bone so that two end of the suture extend to the right in the figure, into a cannula, where they are held taut. A manipulator 3309 having a hook is shown extending from a third cannula in the upper right of the figure. The suture is not yet coupled to the shuttle (although the perspective of the figure shows the loop over the suture anchor).

FIGS. 38B-38E describe one mechanism for passing the suture 3305 through the tissue.

Figure 38B:
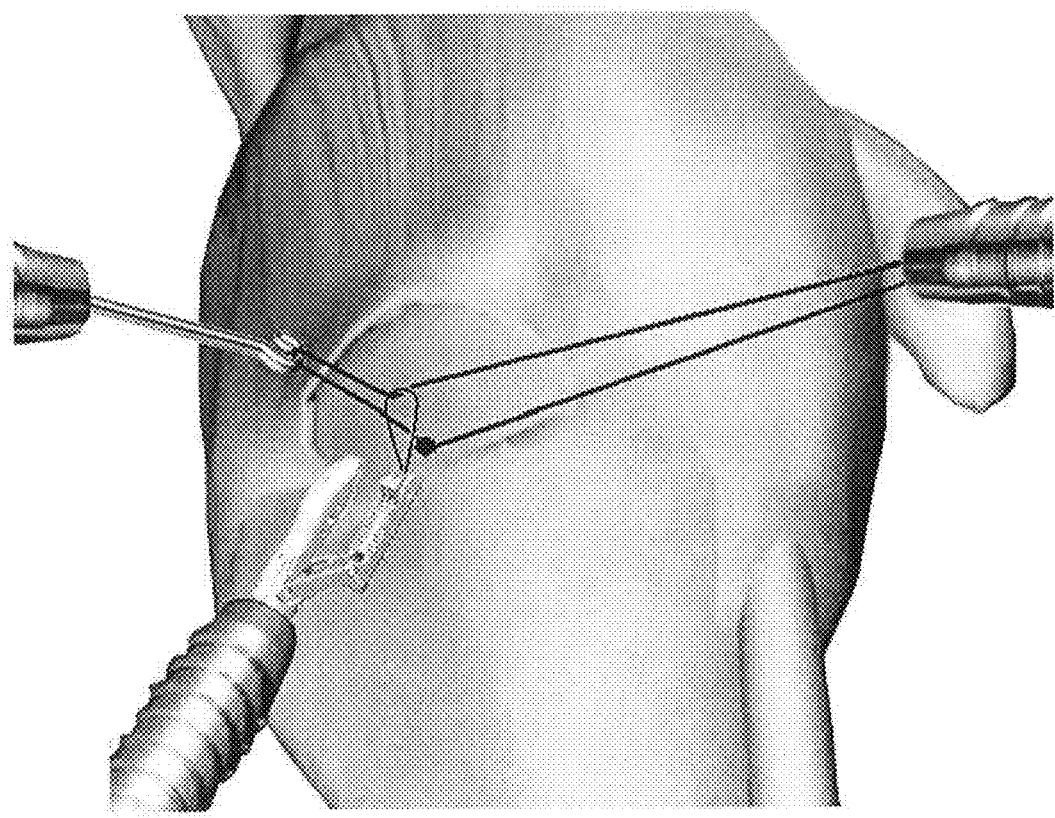

In FIG. 38B, the hook has been extended through the loop of the shuttle to pull the suture through the loop, while it remains anchored and held taut. The manipulator with the hook may be pulled to draw one end (e.g., the non-anchored end) of the suture so that the suture passes through the loop/eyelet of the suture shuttle, as shown in FIG. 38C.

Figure 38C:
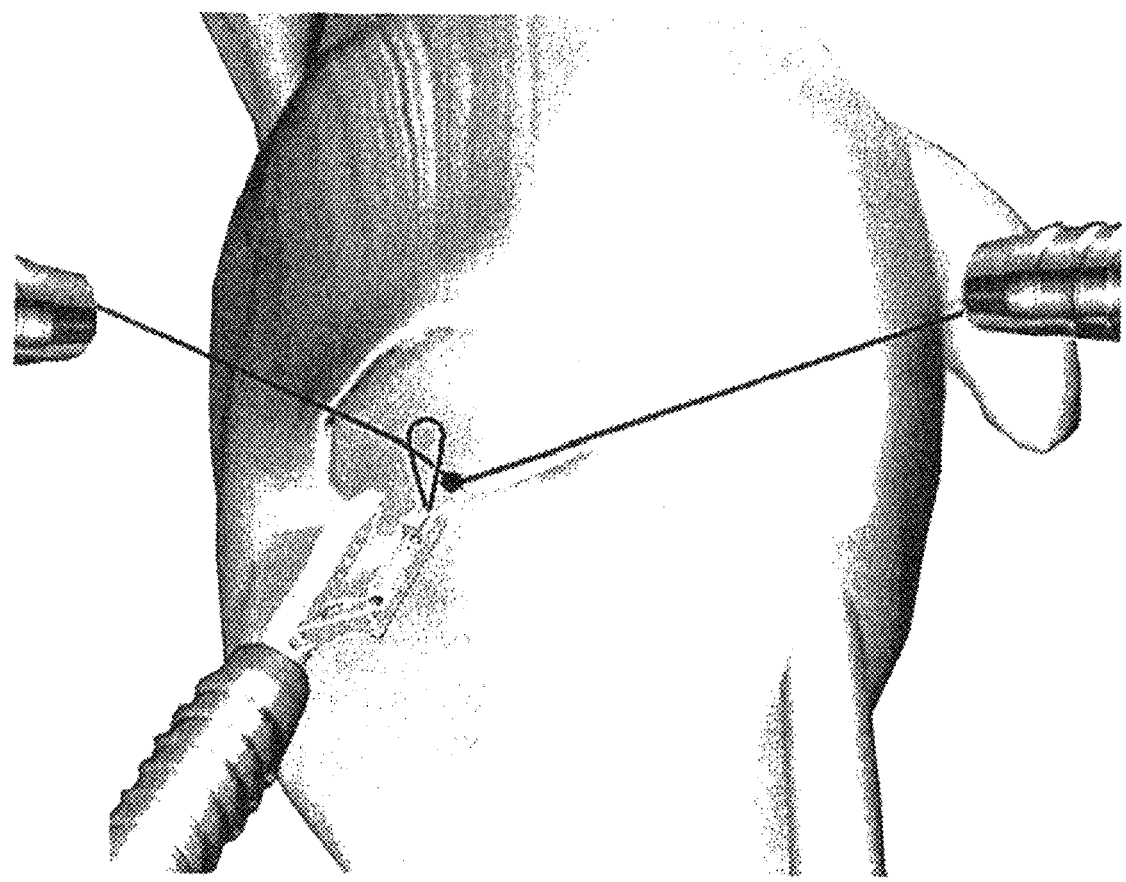
Figure 38D:
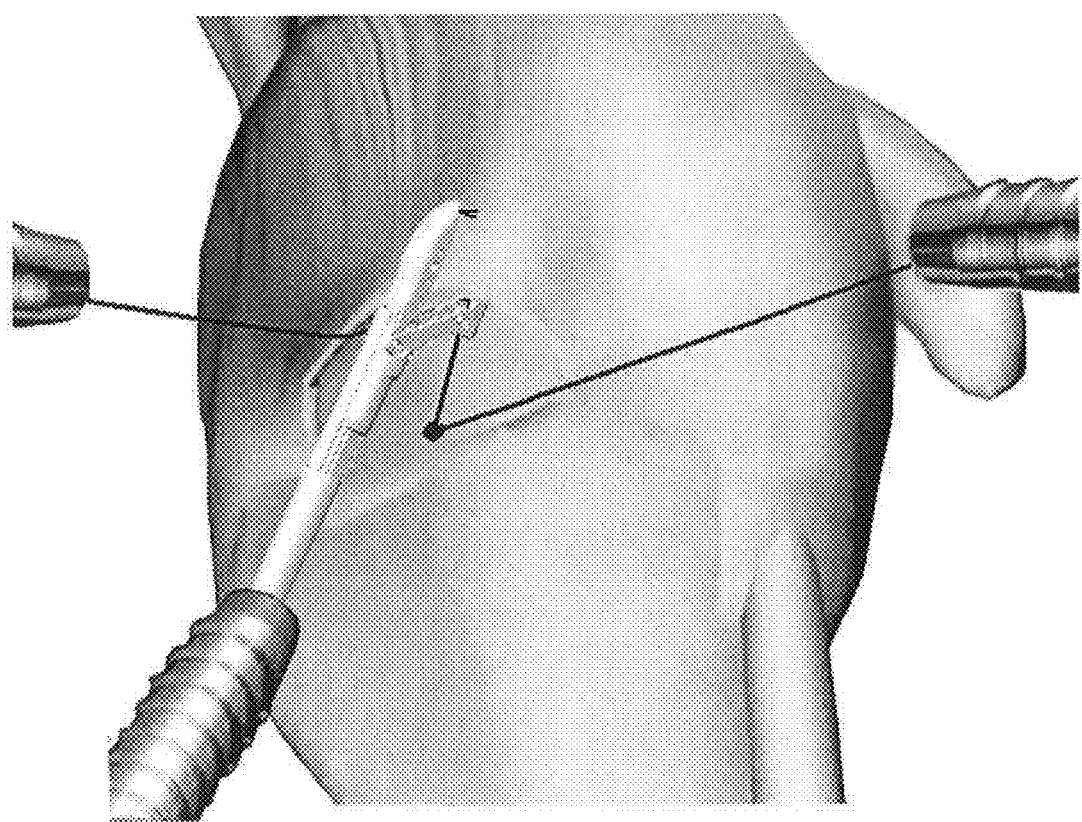

Once the suture is loaded into the suture shuttle and therefore the suture passer, as shown in FIG. 38C, the suture may be passed through the tissue, as illustrated in FIG. 38D. In this figure, the jaws of the suture passer are opened and the suture shuttle is coupled to the end region of the tissue penetrator (as shown in FIG. 38C). The suture passer may be extended (though the cannula in this example) so that the jaws extend over the tissue to be sutured. The suture passer may be activated to extend the tissue penetrator from the lower jaw (in which it is retracted), through the tissue to engage the upper jaw. Passing the tissue penetrator through the tissue also passes the suture shuttle, and pulls the suture (coupled to the loop) through the tissue. The suture shuttle engages the upper jaw and disengages from the tissue penetrator, as described above. Thus the suture has been passed a first direction though the tissue. The tissue penetrator may then be retracted into the lower jaw, leaving the suture shuttle and suture behind on the opposite side of the tissue. The jaws may then be moved or repositioned, and may then be passed through the tissue again, by extending the tissue penetrator through the tissue in a second position to engage the shuttle and suture in the upper jaw, so that they can be pulled back through the tissue on the tissue penetrator as the tissue penetrator is again retracted into the lower jaw (not shown).

Figure 38E:
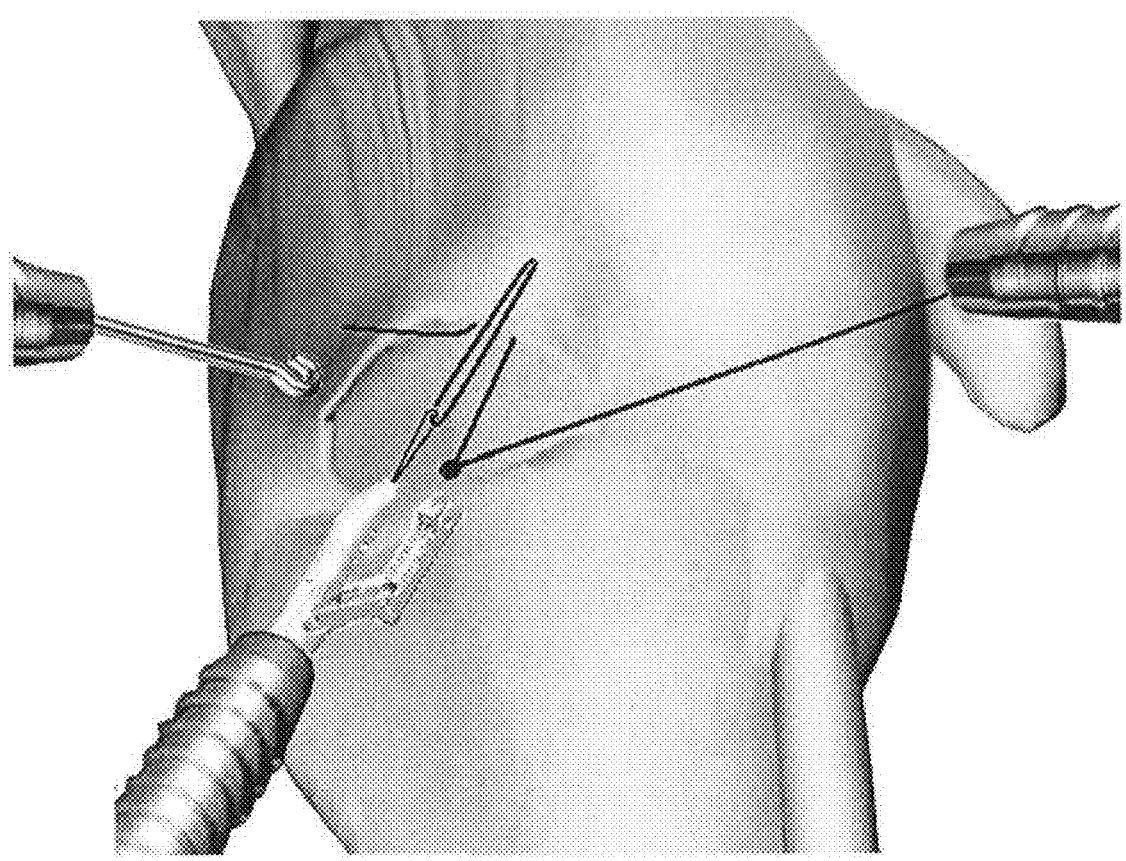

In this example, the suture is passed through the tissue in a doubled configuration, as illustrated in FIG. 38E, since the suture is coupled to the suture passer bypassing through the loop coupled to the suture shuttle. In some variations, the end of the suture may be coupled to the suture passer (e.g., by coupling to a clip or other suture retaining device. In some variations, one end of the suture may be knotted, or may include a stay, so that the suture may be drawn through along its length until it is held securely in the suture shuttle.

Figure 38F:
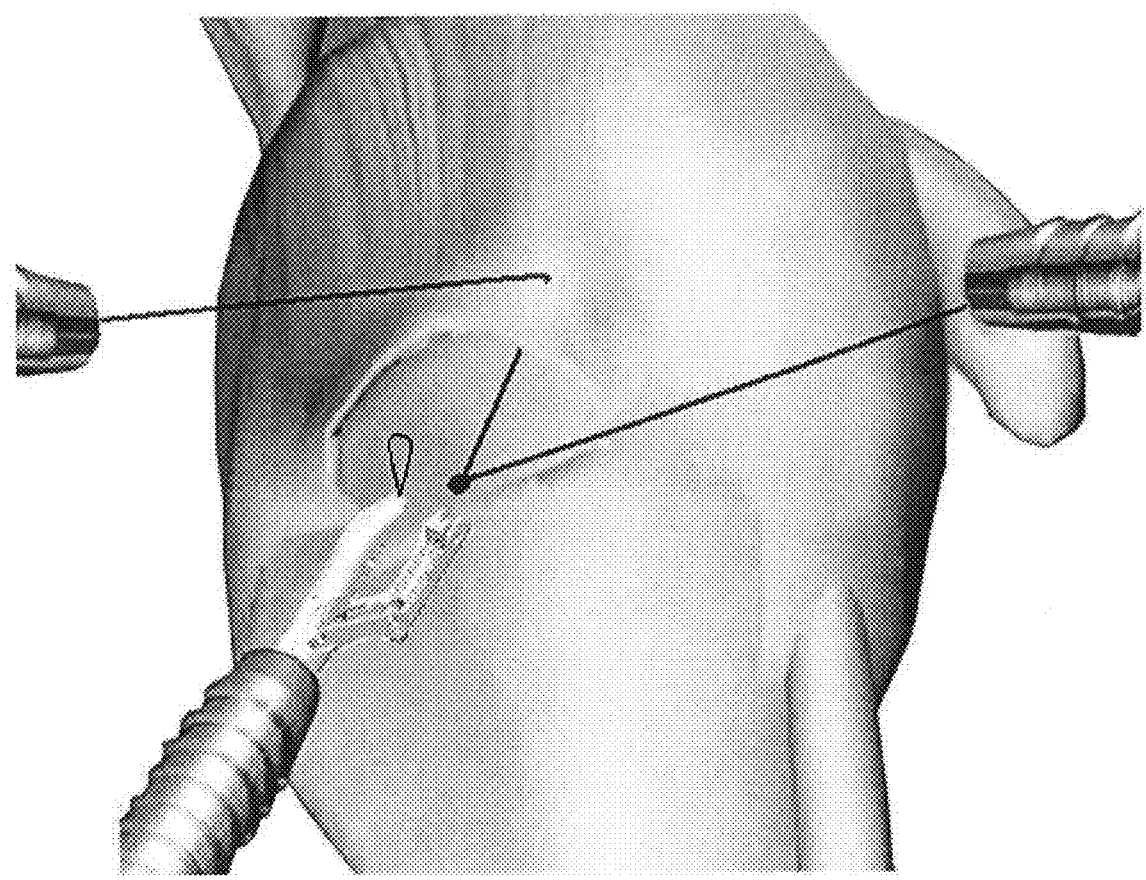
Figure 38G:
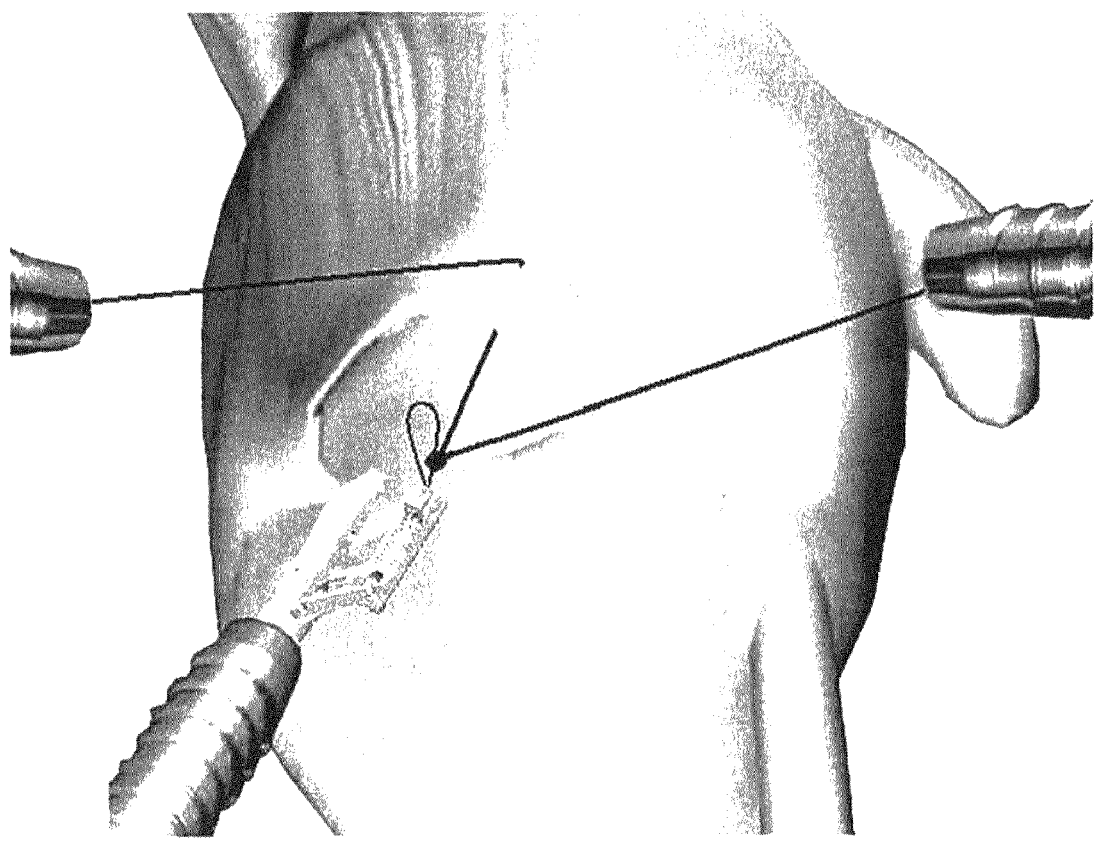

In FIG. 38E, the suture has been pulled through the tissue once, and the doubled-over length of suture extends through the single pass. As mentioned, multiple passes may be made. In this example, one end (the free, un-anchored end) of the suture may be drawn through the tissue so that it is pulled completely through, leaving a single length of suture passing through the tissue, with the free end of the suture extending. This may be performed by using the manipulator having a hooked end. The hook may be used to pull on the loop of suture passing through the tissue until the free end is completely drawn through the tissue, as shown in FIG. 38F. The suture may be pulled completely out of the suture shuttle (as shown in FIG. 38E) by pulling on the length of suture extending between the shuttle and the anchor, or the suture may be left coupled to the suture shuttle (not shown) so that another pass may be made through the tissue, by pulling on the length of the suture extending between the shuttle and the free end of the suture. After any additional passes, the suture may be left "doubled" through the tissue, or the free end of the suture may be pulled through the tissue to leave a single pass of suture through the tissue.

If the loop 3303 is a pull wire, an alternative mechanism can be used for loading the suture within the tissue. In this embodiment, the distal end of the pull wire may be pulled through the tissue before the suture is pulled through the tissue, and in some variations, even before the suture is attached to the pull wire. After the pullwire has been passed, one or more sutures may be coupled to the proximal end of the pull wire and the pull wire may be drawn through the tissue to pull the suture into place; the pull wire may be subsequently removed from the tissue. Alternatively, once the wire has been stitched through the tissue (e.g., from a first position to a second position relative to the tissue), the device can be removed and the wire pulled through the tissue; a loop on the proximal end of the wire may hold a suture. For example, a suture may be threaded through the loop at the proximal end of the pull wire. As the pull wire is drawn out of the tissue, the suture is pulled through the channel left by the pull wire. The suture can then subsequently be tied off with various knot tying methods.

Once the suture has been passed and pulled out of the suture passer, it may be again re-loaded with the suture as described above. The re-loading (and the initial loading) may all be performed within the tissue, as described.

Anchoring the Suture

Also described herein are knotless suture anchors. These knotless suture anchors may be used with any of the suture passers described herein, or as part of any of the methods described herein, or they may be used with other devices or methods. In general, a knotless suture anchor includes a bone anchoring body region (e.g., an anchor body), a loop that is open and extends from the body, and a loop-puller string extending from the body that can be pulled to constrict the loop and/or draw it into the anchor body. The anchor body includes a one-way lock that prevents the loop from opening (e.g., allowing it to be contracted by pulling the suture end, but preventing the suture end moving in the opposite direction). A suture may also extend from the anchor body, and this suture can be passed through or around tissue and anchored to the suture anchor.

Figure 39A:
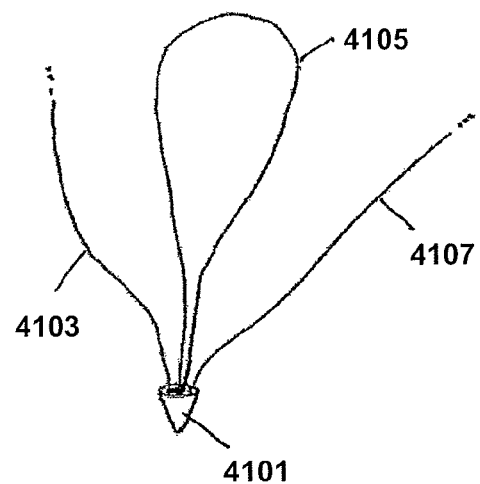
FIG. 39A-39C show one variations of a knotless suture anchor as described herein.

FIG. 39A shows one variation of a knotless suture as described. In FIG. 39A, the anchor body 4101 is conical or tapered, having a more pointed end. In practice, any anchor body shape may be used, particularly shapes that are adapted for insertion or implantation into bone. Examples of anchor body regions are described below with reference to FIGS. 40A-40C. In the variation shown in FIG. 39A, a loop 4105 extends from the anchor body, as do a suture 4103 and a loop-puller string 4107. The figures are not shown to scale. In operation, the suture end 4103 is affixed at one end (e.g., the distal end) within the anchor body, and extends from the anchor body. The loop 4105 also extends from the anchor body 4101, and may be formed from a similar suture material as the suture 4103. One end of the loop 4105 is typically connected to an end (e.g., the distal end) of the loop-puller string 4107. The loop-puller string 4107 may be continuous with the loop. The loop-puller string 4107 also extends from the anchor body 4101. As will be described in greater detail below, the loop-puller string and the suture anchor are engaged by a one-way lock (not visible in FIG. 39A) within the anchor body. This one-way lock prevents the loop-puller string 4107 from being drawn back into the anchor body 4101, but allows the loop-puller string 4107 to be pulled out of the anchor body 4101, thereby collapsing the loop 4105, and drawing the loop into the anchor body 4101. The loop-puller string may be marked (e.g., colored, etc.) or may be attached to a marker that helps differentiate it from other sutures such as the suture 4103. Operation of the tissue anchor is illustrated in FIG. 39B.

Figure 39B:
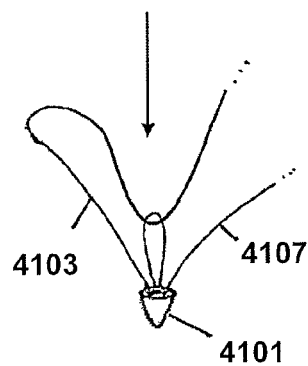
Figure 39C:

In FIG. 39B, the loop 4105 has been contracted by pulling on loop-puller string 4107 until the loop 4105 has been completely collapsed, and drawn into the anchor body 4101. As will be described in greater detail below, another suture or sutures, or a portion of an implant, may be passed through the loop 4105. FIG. 39B shows the proximal end of the suture end 4103 has been passed through the loop. In some variations, an entirely different suture may or material may be passed through the loop. The loop may be "collapsed" by pulling on the loop-puller string 4107, drawing the loop into the anchor body, and therefore anchor the suture or material passed through the loop to the anchor body, and thus the bone or other material to which the anchor body is attached. It may be beneficial to draw the loop 4105 completely into the anchor body 4101 both to secure the knotless suture anchoring of the suture or other material, and also to prevent the anchored material from being exposed to the surrounding tissue. This may also help ensure that the tissue or other material being secured is reduced and secured to the bone (or tissue or other material that it is being secured to) to prevent gap formation at the repair site. Anchoring the material within the anchor body may protect the surrounding tissue from rubbing against the suture material. Once the loop 4105 has been drawn into the anchor body, the loop-puller string extending from the anchor body may be cut, as shown in FIG. 39C and (as described below) in FIG. 46G.

Figure 40A:
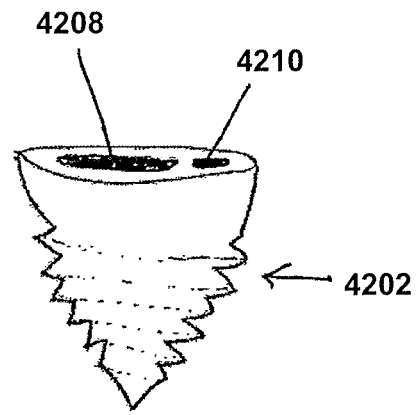
FIGS. 40A-40C show variations of the anchor bodies for knotless suture anchors.
Figure 40B:
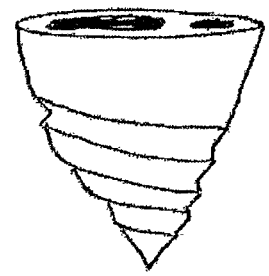
Figure 40C:
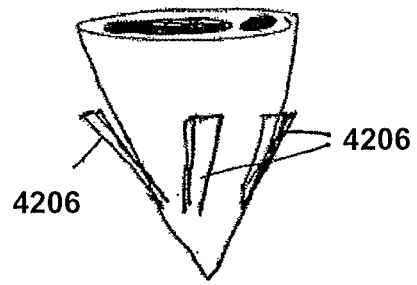

The anchor body 4101 region may therefore be configured so that it can be secured to a region of the body, and particularly bony regions, while presenting a smooth or atraumatic surface to the surrounding tissue, once anchored in the body. In addition, the anchor body may be configured so that the anchor body can be readily secured within the patient, including bone regions. FIGS. 40A-40C illustrate variations of anchor bodies that are adapted for anchoring in bone.

For example, FIG. 40A is one variation of an anchor body having ridged or notched regions 4202 along the outside of a tapered region of the body. This tapered region may be configured for insertion into bone, and the ridges/notches may help secure the anchor in place. FIG. 40B shows another variation, in which the anchor body is tapered and threaded, which may also help insertion into bone, by allowing the device to be screwed into a bone. In some variations, the anchor body is adapted to secure the device by including one or more expanding anchor regions. For example, the variation shown in FIG. 40C includes arms 4206 that can flange out from the anchor body, preventing the anchor from being readily withdrawn, once it has been implanted into a bone. The anchor body may also include one or more passages for bone cement and/or additional bone screws or pins. Thus, the anchor body may be secured firmly to bone. In some variations, the anchor body may be configured to be releasably secured to bone. For example, the anchor body may be resorbsorbable or bioabsorbable. In some variations, the anchor may promote bone in-growth, and may include openings or regions for bone in-growth. The anchor body may also include bone growth promoting materials.

The region of the anchor body that is not configured to be embedded into the bone may be adapted so that it presents an atraumatic surface. For example, this surface may be smooth, or may be compliant (e.g., coated or fashioned of a compliant material), and/or lubricious. In addition, this surface may also include one or more openings from which the loop and suture end(s) extend. In FIGS. 40A-40C the anchor body includes two openings 4208 and 4210. For example, the loop and a suture end may extend from the first opening 4208, and the loop-puller string, which may be drawn to collapse the loop, may extend from the second opening 4210. Although one of the openings 4208 shown in FIGS. 40A-40C is larger than the second opening 4210, in some variations, the openings may be the same size. In some variations only a single opening from which the loop and the suture end(s) and loop-puller string extend is used. In other variations, three or more openings are included. Although the variations illustrated include one suture extending from the anchor body, in some variations, multiple sutures may be connected and extend from the anchor body.

The anchor body region may be formed of any appropriate material(s), including metals, alloys, ceramics, plastics: rubbers, polymers, biologics or some combination thereof. Similarly, the material forming the loop and the loop-puller string and any suture ends extending from the anchor body may be formed of a suture material, or any other appropriate material. In general, the material forming the loop, loop-puller string, and suture are formed from a flexible material. This material may be absorbable or biodegradable. In some variations, the material is formed of a traditional suture material (e.g., surgical gut, chromic suture materials, polylactic acid, capraolactone, polyglycolic acid, nylon, polypropylene, polyester, silks, etc.), and may be monofilament, woven, braided, or the like. The material forming the loop and/or suture end(s) may also be formed of flexible metals, alloys, polymers, or the like. Any appropriate size (length and/or diameter) may be used.

Figure 41A:
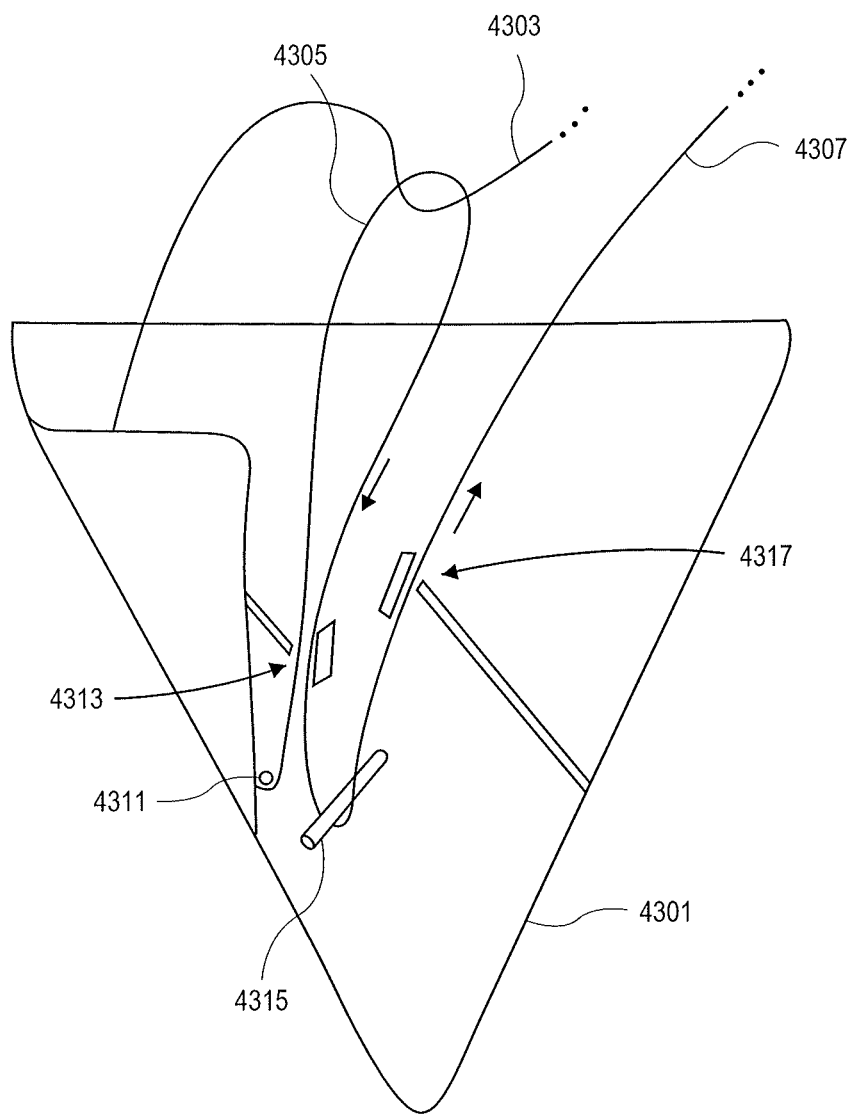
FIGS. 41A and 41B show cross-sections through one variation of a knotless suture anchor.
Figure 41B:
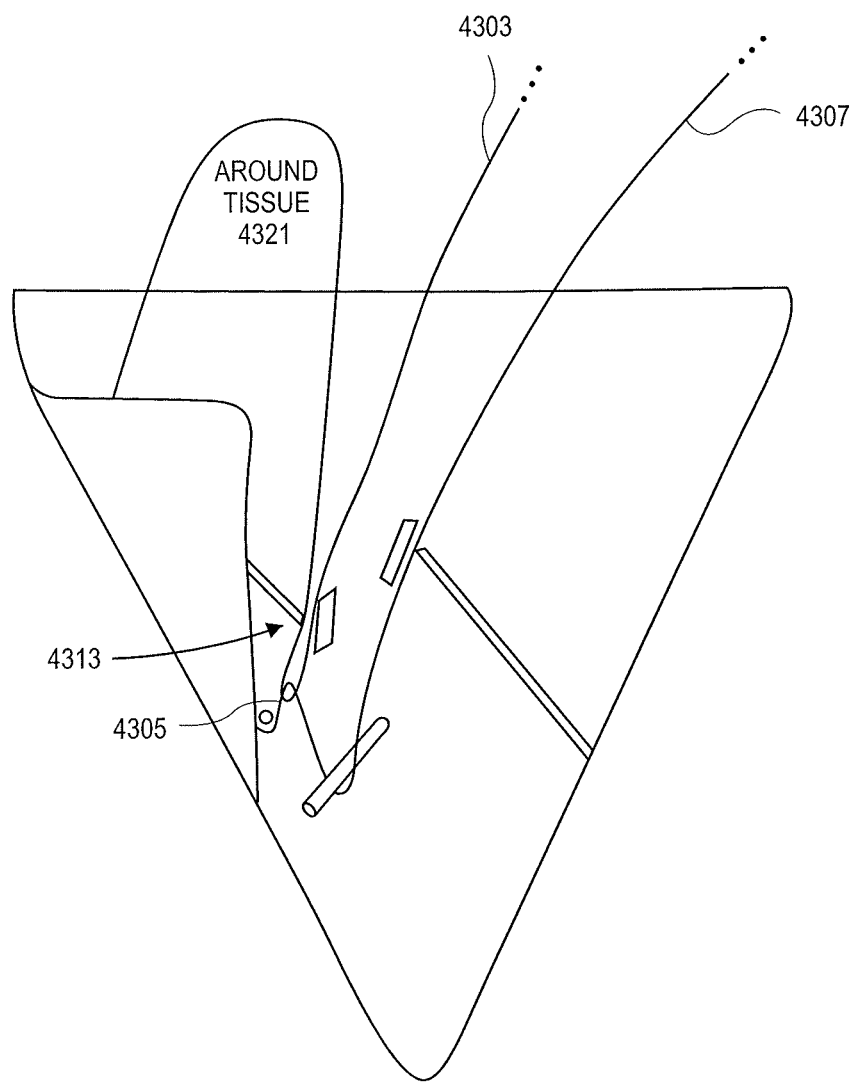

As mentioned above, the anchor body typically includes a one-way lock. FIGS. 41A-41B illustrate a partial cross-section through an anchor body schematically illustrating the operation of one variation of a knotless suture anchor. In FIG. 41A, the loop 4305 extends from the anchor body 4301. One end 311 of the loop 305 is continuous with the suture end 4303 extending from the anchor body, and the other end of the loop is continuous with the loop-puller string 4307 extending from the anchor body 4301. The material forming the loop and the suture and loop-puller string passes around a first pulley 4311, through a first one-way lock 4313, forms a loop 4305, and then passes around a second pulley 4315 and through a second one-way lock 4317. The pulley around which the material passes may be a rolling pulley, or simply a pin, bar, or the like.

In FIG. 41A, the one-way locks are configured to sandwich the string forming the loop (and suture and loop-puller string)

between two or more surfaces in such a way that the string/suture can only move freely in one direction through the one-way locks, preventing the loop from loosening. Thus, these two locks are oriented in opposite directions in this variation. For example, the first lock 4313 allows the suture 4303 to be pulled, thereby contracting the loop. The second lock 4317 likewise allows the loop-puller string 4307 to be pulled to contract the loop, but prevents the loop from loosening. As the ends of the suture and loop-puller string are pulled, the loop may pull into the anchor body 4301, as shown in FIG. 41B.

In FIG. 41B, the interface between the suture end 4303 and the loop 4305 has been withdrawn completely into the anchor body, and has passed through the first one-way lock 4313, effectively locking the suture 4303 so that it cannot loosen as well. Before the suture was passed through the loop 4305, it was first passed through a tissue or device to be anchored 4321. Once anchoring is complete, the loop-puller string end 4307 may be trimmed or cut, as may the suture end 4303. In some variations the anchor body may also include a bobbin, cam, or spring that will pull the cut end of the suture and/or loop-puller string extending from the anchor body into the anchor body once it has been cut. For example, putting tension on the loop-puller string may extend the spring or bobbin and the loop-puller string end may be cut while the tension is maintained. After cutting and release of the tension, the spring or bobbin may then relax back down, drawing the cut end into the anchor body. Typically this spring or bobbin is located in the anchor body after any one-way lock.

Figure 42:
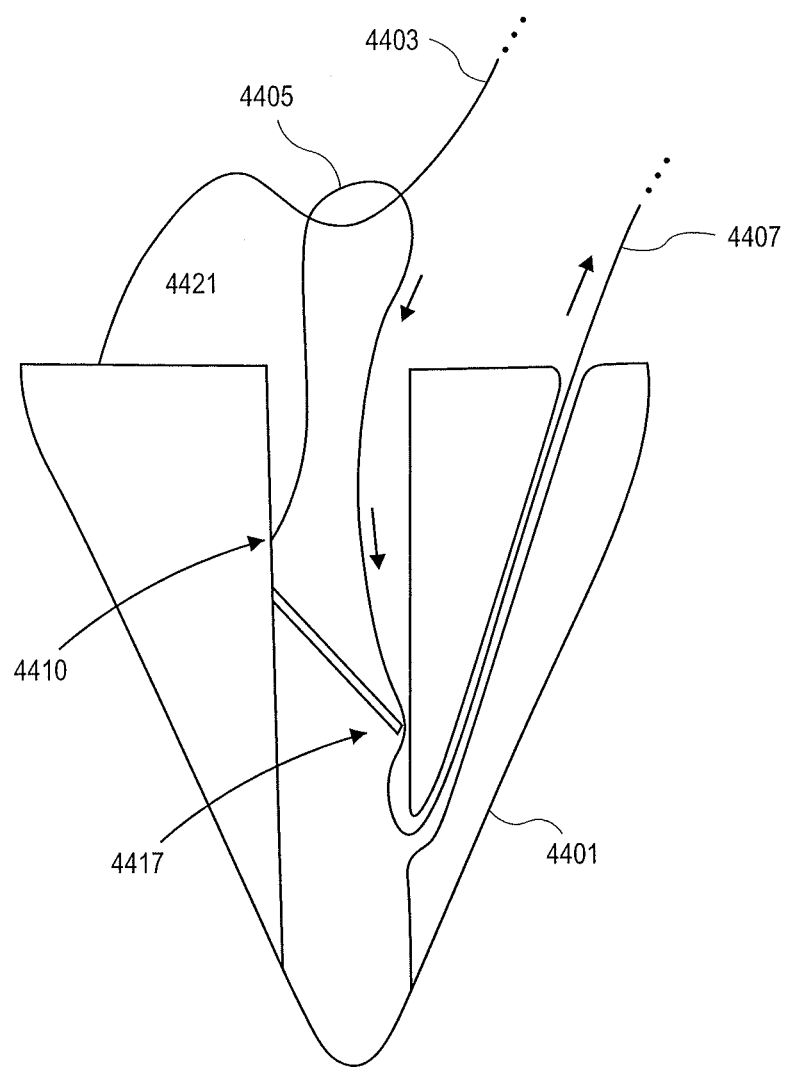
FIG. 42 is a cross-section through one variation of a knotless suture anchor

In some variations, one end of the loop is secured to the inside of the anchor body, and the distal end of the suture extending from the anchor body may also be attached to the inside of the anchor body. FIG. 42 illustrates an example of such a variation. In FIG. 42, the distal end of the first suture end extending from the anchor body is secured within the anchor body, and the distal end 4410 of the material forming the loop 405 is secured to a wall of the inside of the anchor body 4401. The other end of the material forming the loop 4405 is continuous with the material forming the loop-puller string 4407 extending from the anchor body 4401. The loop passes through a one-way lock 4417 before exiting anchor body 4401 as the loop-puller string 4407. The suture 4403 passes through or around a tissue (or implant 4421) and then through the loop 4405. Pulling on the loop-puller string extending from the anchor body 4407 will constrict the loop, eventually drawing the loop 4405 and a portion of the suture 4403 into the anchor body, where it may again be pulled below the one-way lock 4417, securing it in the anchor body 4401.

Figure 43:
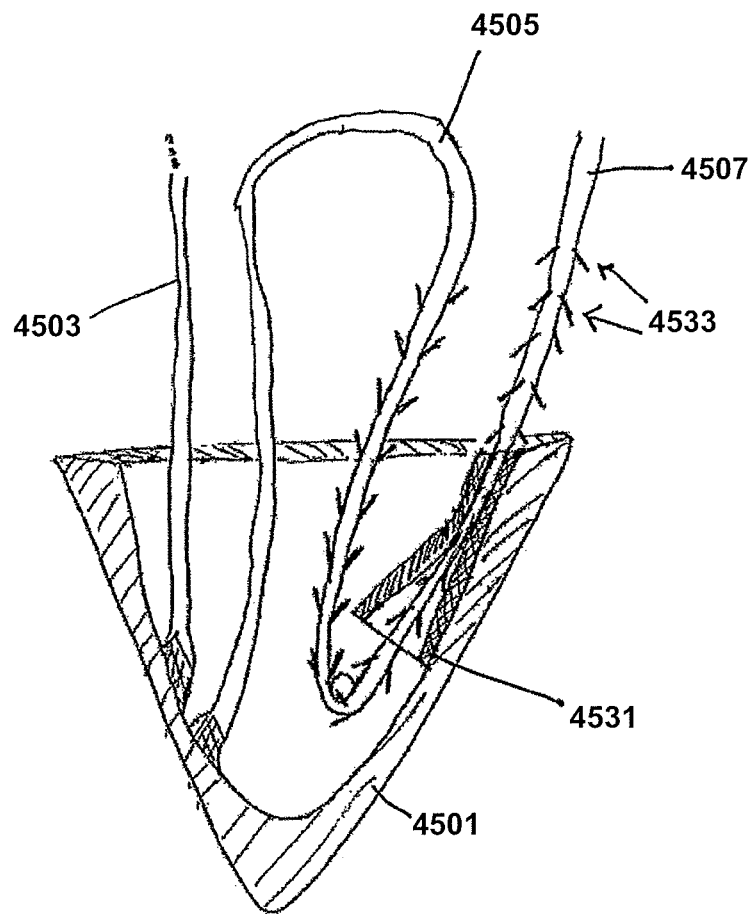
FIG. 43 is a cross-section through another variation of a knotless suture anchor.

FIG. 43 shows another variation of a knotless suture anchor, including a different variation of the one-way anchor valve that prevents the material forming the loop 4505 and the loop-puller string extending 4507 from anchor body 4501 from moving in more than one direction. In this example the one-way valve includes a funnel-like opening 4531 into which the string of the loop-puller string and/or loop passes. The string (e.g., suture) material forming a portion of the loop 4505 and the loop-puller string 4507 in this example includes a plurality of locking clips 4533. These locking clips may be arms or sheets extending from the suture that will compress when drawn through the funnel 4531 of the one-way lock towards the narrow region, then expand after exiting, preventing the string from moving back through the lock. In some variations these strings forming the loop and/or loop-puller string include beads, knots, or other structures which may be rigid or semi-rigid, and the funnel portion of the one-way lock is slightly flexible so that it can expand as the string is drawn in one direction; the configuration prevents the string from being pulled in the opposite direction.

Figure 44:
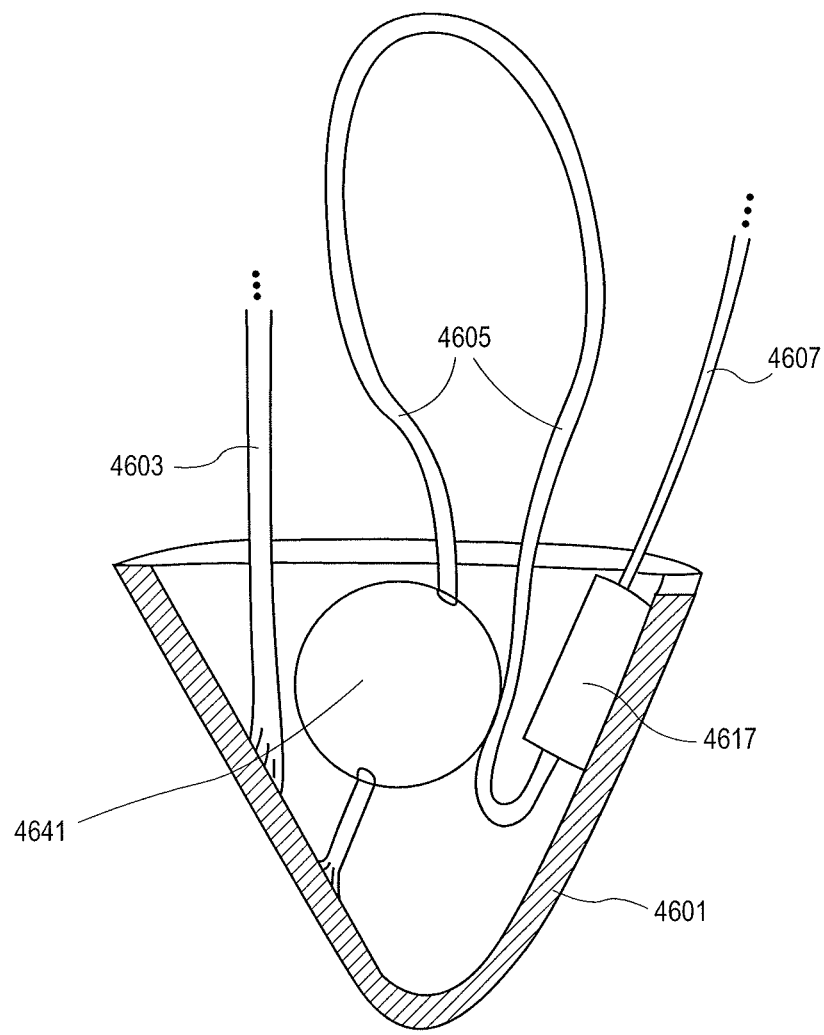
FIG. 44 is a cross-section through another variation of a knotless suture anchor.

In some variations an additional locking mechanism is included for securing a material (e.g., the suture) captured by the loop within the anchor body. For example, a locking mechanism may include a locking bead as illustrated in FIG. 44. In FIG. 44, the locking bead 4641 is threaded on the distal end of the loop 4605. After a suture (e.g., the first suture end 4603) is passed through the loop 4605, and drawn into the anchor body 4601 with the loop 4605, it may be held secured against the inner surfaces of the anchor body 4601 as the loop is secured by the one-way lock 4617. Although a spherical bead is shown in FIG. 44, other shapes may be used, including shapes with one or more edges or points.

In addition or instead of locking beads, one or more materials may also be used to help secure the suture(s) and loop within the anchor body. For example, cement may be included. In some variations the cement is activatable or releasable, so that it becomes active only after the loop and/or suture has been secured within the anchor body. In some variations a crushable or frangible packet or container of cement is released after the loop has been drawn into the anchor body. In some variations, the cement may be activated by bringing two or more materials together. For example, the distal region of the first suture end may be treated with a material that bonds to the distal end of the loop; these two regions typically only meet once the loop has been withdrawn into the anchor body. In one variation the locking bead described in FIG. 44 is frangible or includes frangible regions that release a cement material after the loop has been drawn into the anchor body. Any appropriate cement may be used, particularly biocompatible cements (e.g., polymethylmethacrolate, cyanoacrylates, etc.).

In operation, the knotless suture anchors described herein may be used by first anchoring to a bone or other body region to which the tissue and/or implant is to be secured. In some variations the knotless tissue anchor may be secured to an applicator which may assist in placing the anchor in the bone or other tissue. FIG. 45A-45C illustrates the use of an applicator for placing one variation of a knotless tissue anchor. In this variation the knotless tissue anchor 4701 is secured to the distal end of an applicator including a sheath 4751. The sheath is an elongate member having an inner lumen through which the loop, loop-puller string, and any suture attached to the device, extend. The sheath may be relatively stiff, so that it can be used to apply force to insert the device into the bone. FIG. 45A shows a bone region and a region of soft tissue that has been pulled away from the bone. The methods described herein may be used to re-attach the soft tissue to the bone. For example, in FIG. 45B, a knotless suture anchor is being secured into the bone, using an applicator. In some variations the bone may be prepared before this, for example, by drilling a hole or opening into which the body of the knotless suture anchor will be secured. In other variations, the body of the knotless suture anchor may itself be adapted for securing into the bone. In other variations, bone cement, bone screw, or other mechanism for fixing the knotless suture anchor in the bone may be used.

The knotless suture anchor may be released from the sheath of the applicator after it has been inserted, as shown in FIG. 45C. The applicator may be withdrawn, leaving the loop, loop-puller string, and suture end exposed, as shown in FIG. 45D.

Figures 46A, 46B, 46C, 46D:
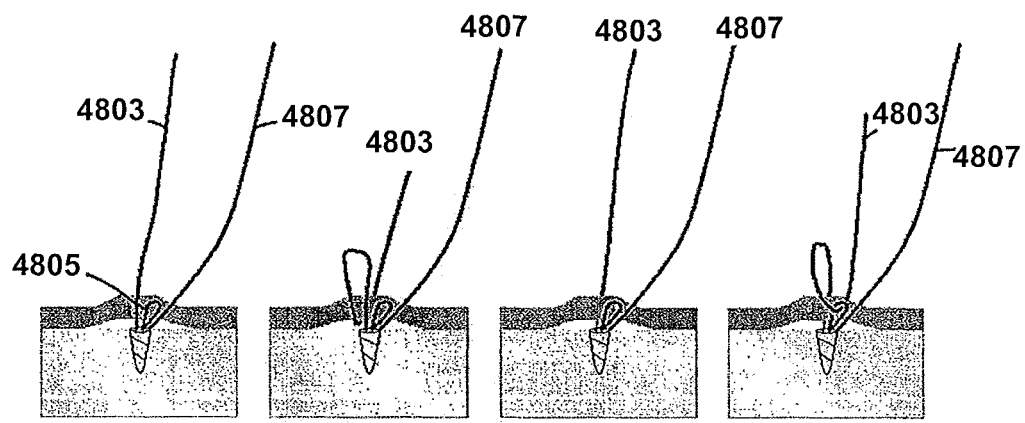
FIG. 46A-46G illustrate a method of suturing and anchoring using one variation of the knotless suture anchor described herein.

FIGS. 46A-46G illustrate the use of a knotless suture anchor such as the one shown in FIGS. 45A-45D after it has been secured to a tissue (e.g., bone). In FIG. 46A, the first suture end 4803 and the loop-puller string 4807, as well as the loop 4805 are shown extending from the implanted anchor body. In FIG. 46B, the first suture end is then passed through or around the tissue to be secured by the knotless suture anchor. Any appropriate suturing technique or method may be used to suture the tissue with the first suture end. For example, the first suture end may include a shuttle or other attachment so that it can be used with a continuous suture passer. This may be particularly beneficial for passing the suture multiple times through the tissue, or passing it through the tissue and then through the loop, as required here. Continuous suture passers may be advantageous or even necessary when the tissue being secured is in hard-to-reach or hard-to-maneuver regions, such as the glenohumeral joint for labral repairs or the subacromial space of the shoulder for rotator cuff repairs, etc. In some variations the proximal end of the first suture end is adapted for use with a continuous suture passer.

Figures 46E, 46F, 46G:
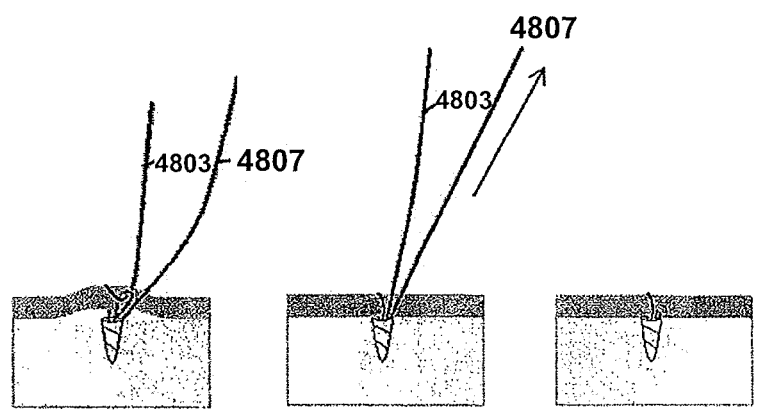

In FIG. 46D the suture end is then drawn around (or back through) the tissue so that it can pass through the loop of the knotless tissue anchor. As mentioned above, any number of stitches through the tissue may be performed with the suture before passing through the loop of the suture anchor. In FIG. 46E the suture is secured by drawing it through the loop 4805, and thereafter the loop is constricted by pulling on the loop-puller string 4807, as shown in FIG. 46F. The loop-puller string may be drawn until the loop is completely retracted within the anchor body, as shown, securing the tissue and the suture 803 within the anchor body. In FIG. 46G the loose suture end 4803 and loop-puller string 4807 have been clipped or cut.

FIG. 47A illustrates another variation of a knotless suture anchor. In this variation the knotless suture anchor includes a suture attached within the anchor body, and a loop and loop-puller string extending from the anchor body. The suture may be passed through the loop and secured within the anchor body, as illustrated in FIGS. 47B and 47C. As the suture is drawn into the anchor body, it may loop around tissue (not shown, though see FIG. 51), anchoring the tissue in place as the suture is anchored. While drawing on the loop-puller string to lock the suture in place, the suture may be drawn to contract around the tissue (not shown). The suture may be anchored in the anchor body by pulling the loop until it is secured within the anchor body (e.g., so that the loop-puller string cannot be pulled any further).

Figure 48A:
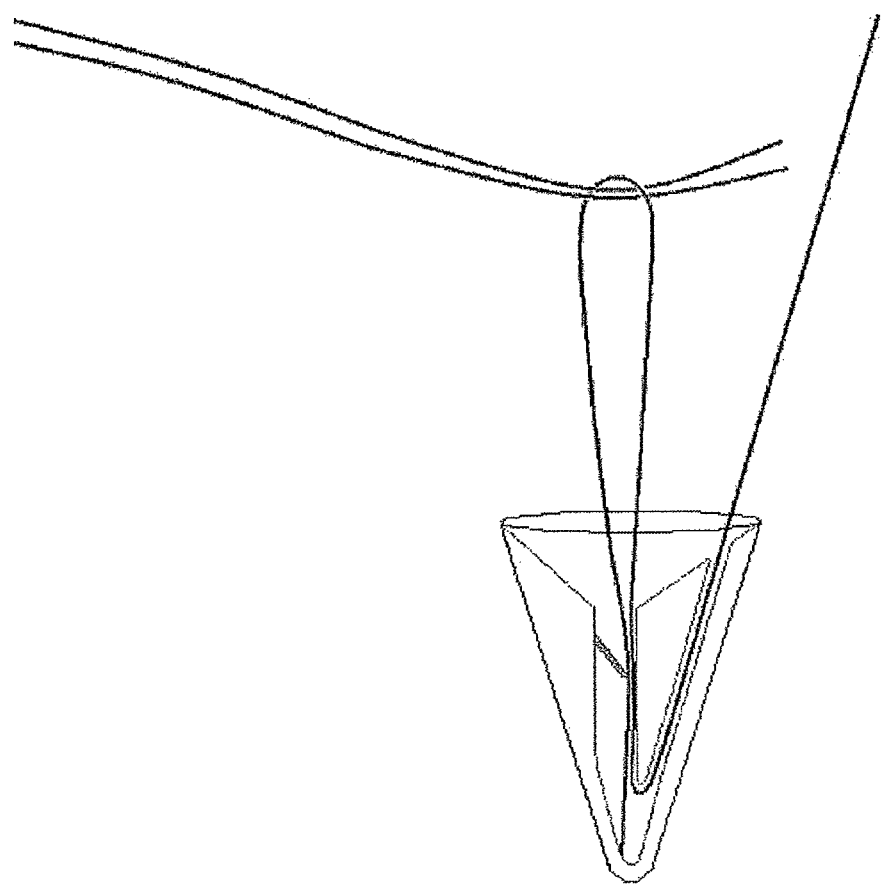
FIGS. 48A-48C illustrate operation of a knotless tissue anchor to anchor two sutures.
Figure 48B:
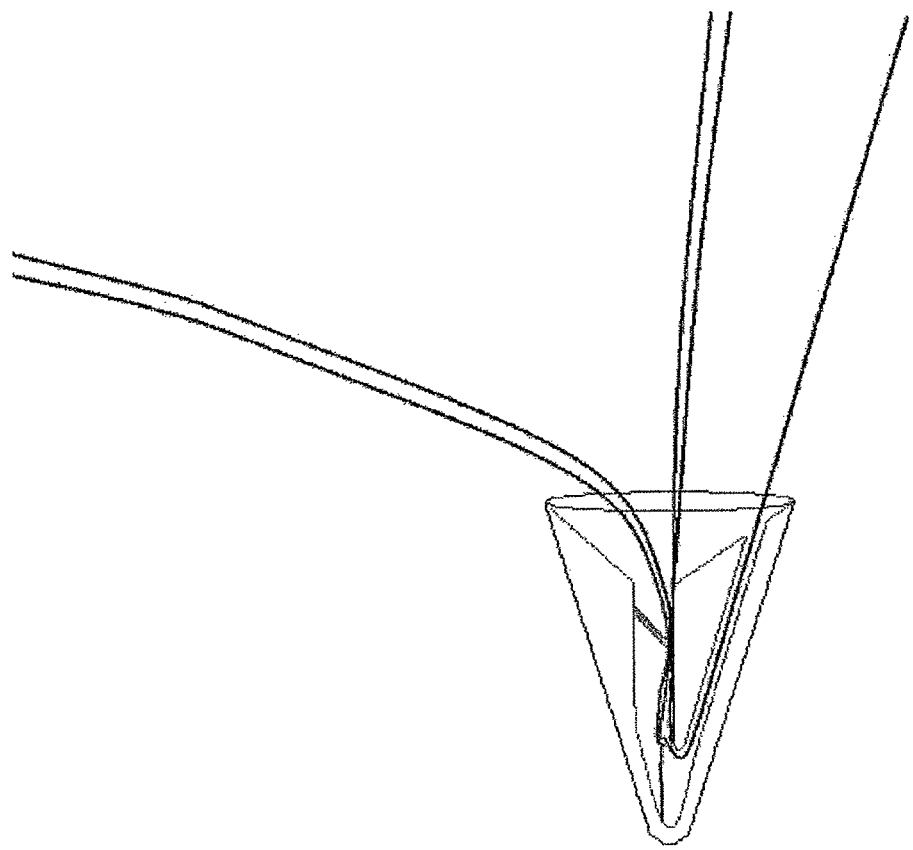
Figure 48C:
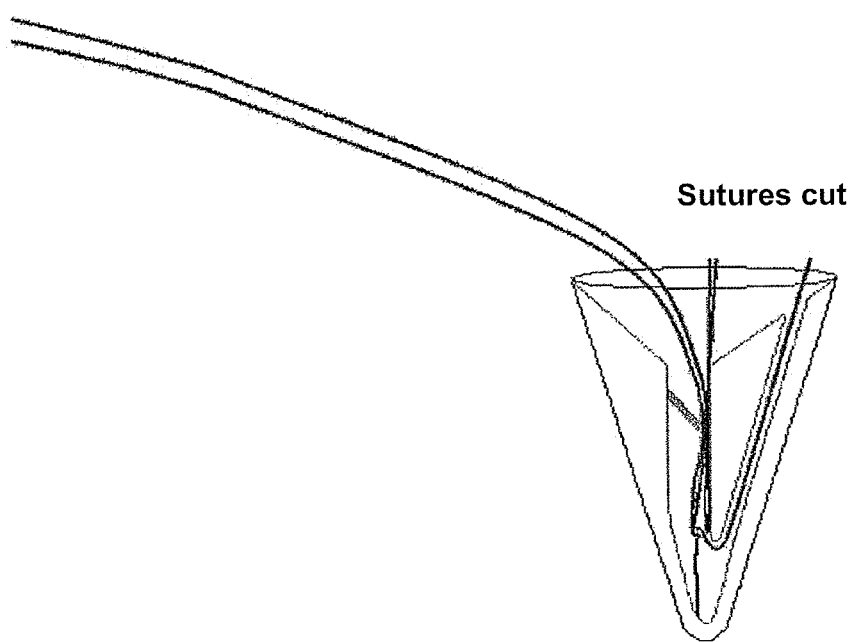

FIGS. 48A-48C illustrate another variation of a knotless suture anchor similar to those described above, but used to secure more than one suture. In the knotless suture anchor shown in FIG. 48A, a suture is not initially attached to the anchor body (e.g., compare to FIG. 47A). In this example, two sutures (drawn as parallel in this figure, although they may be oriented differently) are pushed or otherwise passed through the open loop extending from the suture body, and the loop is then drawn into the suture body to lock the plurality of sutures in position. FIGS. 48B and 48C illustrate this process. In FIG. 48C, one end of the sutures are cut.

Examples such as this may be beneficial when attempting to knotlessly anchor suture ends that have been passed through free tissue or passed from a different anchor through tissue (and then to an anchor). For example, this technique may be part of a "double row" of suturing used for rotator cuff repair.

In general, the sutures described herein may be pushed, pulled, shuttled, relayed or otherwise passed through the loop. Examples of suture passers that may push or shuttle the suture through the loop of the knotless suture anchor were previously incorporated by reference. Because the method using these devices may be performed deep within tissue, including as part of an arthroscopic or minimally invasive procedure, tissue passers such as those referred to may be particularly useful.

In all of these examples, the loop is external to the anchor body when the suture is passed through it. The loop may be relatively small, and difficult to pass a suture through. In operation, a suture may not need to be passed completely through the loop in order to be anchored. For example, a suture may be anchored by passing even a loop or section of an elongate suture through the loop, then contracting the loop into the anchor body with the portion of suture within the loop (e.g., a doubled-over region of suture), to anchor the suture in place. In many of the methods of operation of the knotless suture anchor described herein, the suture, whether initially anchored to the knotless anchor or from another location or anchor, is typically fed through the loop while the loop is external to the anchor body.

As mentioned, the loop and loop-puller string may be formed of any appropriate material(s), and may be part of the same string. For example, the string forming the loop and/or loop-puller string may be formed of suture, wire, cord, Nitinol, etc. For example, the string forming the loop-puller string and/or loop may be a coated cable.

Figures 49A, 49B:
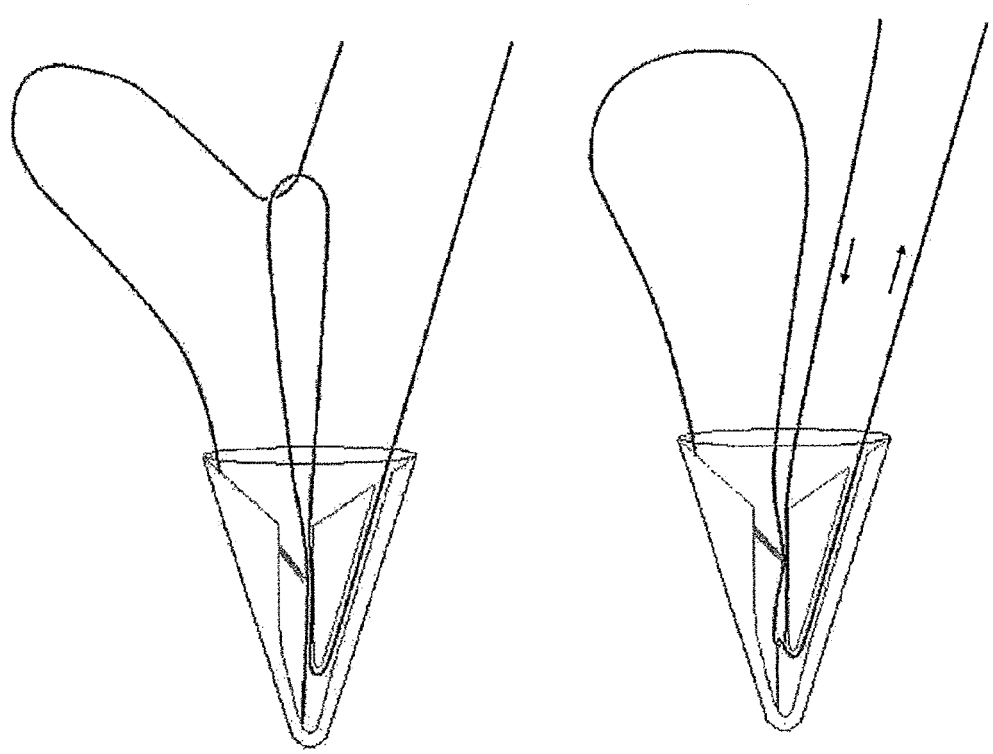
FIGS. 49A and 49B illustrate operation of another variation of a suture anchor.
Figure 50C:
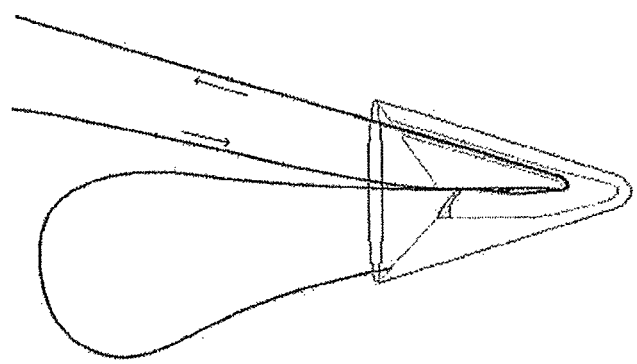
FIG. 50A shows another variation of a knotless suture anchor having a fixed loop which may be drawn into the anchor body to anchor a suture, as illustrated in FIG. 50B-50C.
Figure 50B:
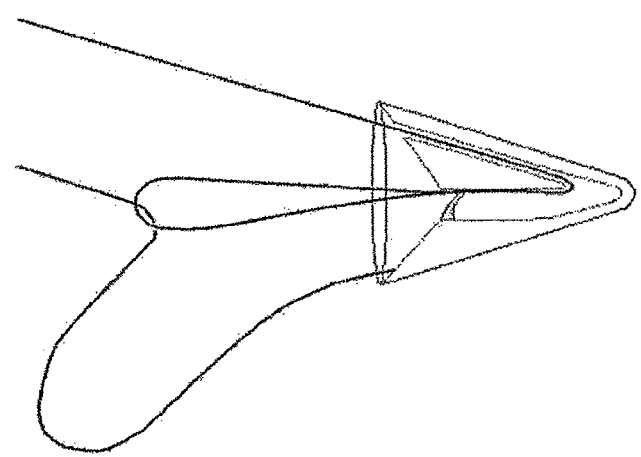
Figure 50A:
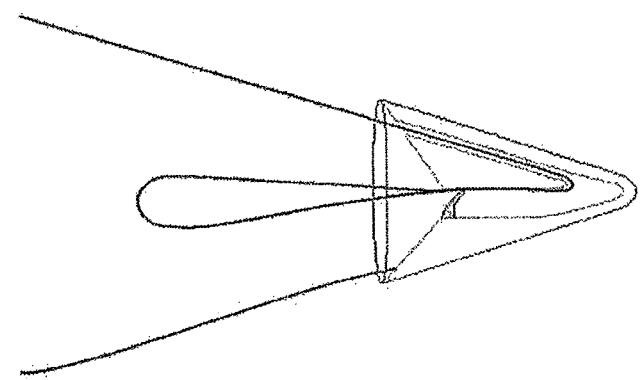

In some variations, the loop and/or loop-puller string are not directly attached to the anchor (e.g., anchor body). Instead, the loop is connected to the loop-puller string only, so that no end of the loop is attached to the anchor body. In this variation the loop may be a lasso-type configuration, in which one end of the string forming the loop attaches to the loop-puller string to form the loop from the loop-puller string. This is illustrated in FIGS. 49A-49B. In some variations the loop may be of a fixed size, since the loop is formed by tying, or affixing a free end a string to a doubled back region of the string. In other variations, the loop formed in the string may be expanded or contracted, lasso-like. In variations in which the loop has a fixed size, the loop rather than just the loop-puller string, may be drawn into the one-way lock, and held in position. For example, in FIG. 49B, drawing on the loop-puller string pulls the loop into the anchor body, and into the one-way lock in the anchor body. FIGS. 50A-50C illustrate another variation in which the loop extending from the anchor body is a fixed size, and the loop is drawn into the anchor body by pulling on the loop-puller string.

Figure 51:
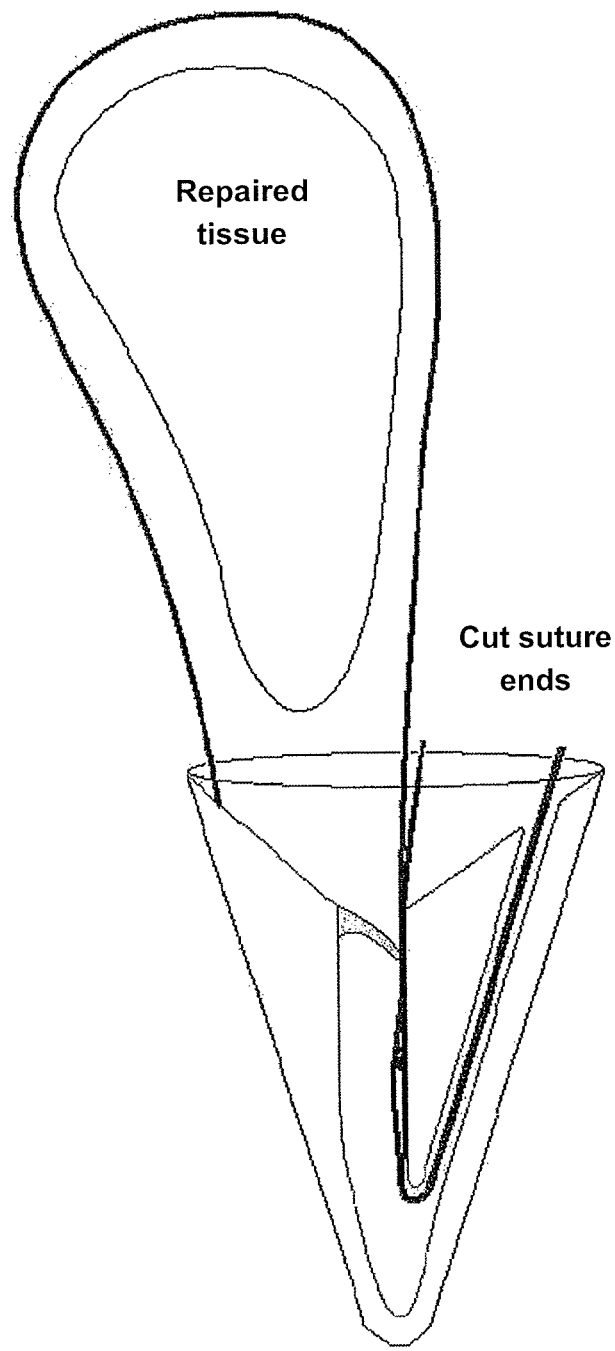
FIG. 51 illustrates a knotless suture anchor, such as the one shown in FIG. 51A, securing a region of tissue.

FIG. 51 illustrates a variation similar to that shown in FIG. 50A after anchoring a region of repaired tissue. In this example the suture (shown as being attached to the interior of the anchor body, has been passed around or through a region of tissue to be repaired, and passed through the loop, as illustrated in FIG. 50B, for example. The loop-puller string has been pulled to draw the loop into the anchor body. As the loop-puller string is drawn in, first the loop-puller string, and then the loop, is drawn into the one-way lock so that the loop cannot be extended from the anchor body again. Drawing the loop, with the suture captured in it, into the anchor body effectively locks the suture in the anchor, and secures the tissue in position, as shown.

Figure 52A:
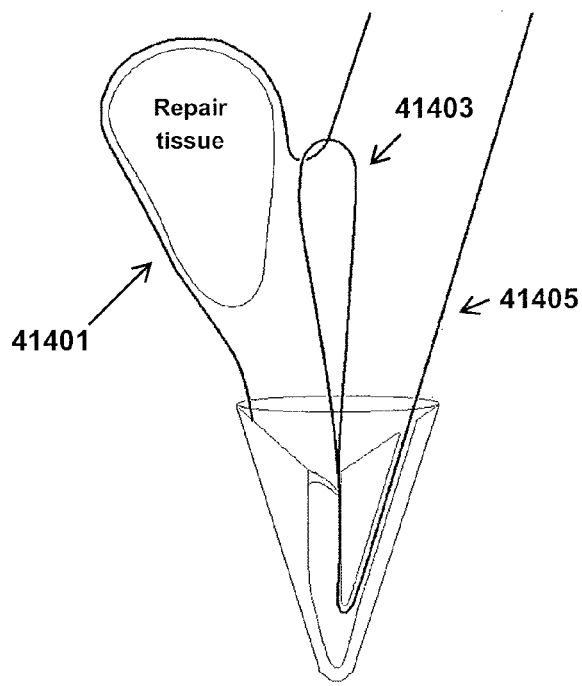
FIG. 52A-52E illustrates use of a knotless suture anchor.
Figure 52B:
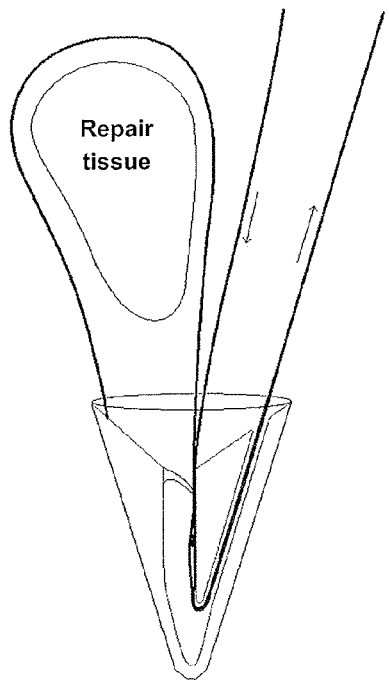
Figure 52C:
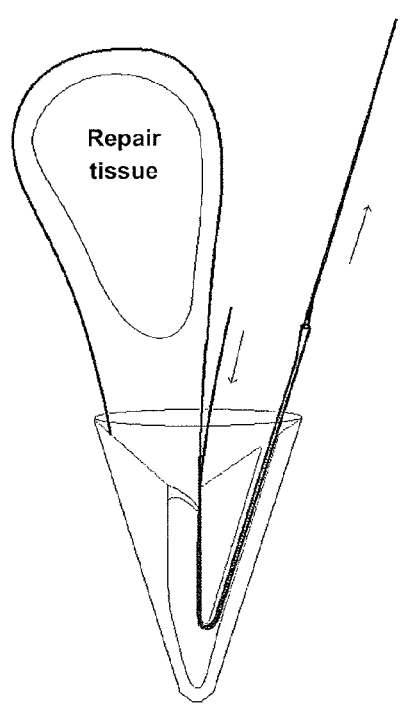
Figure 52D:
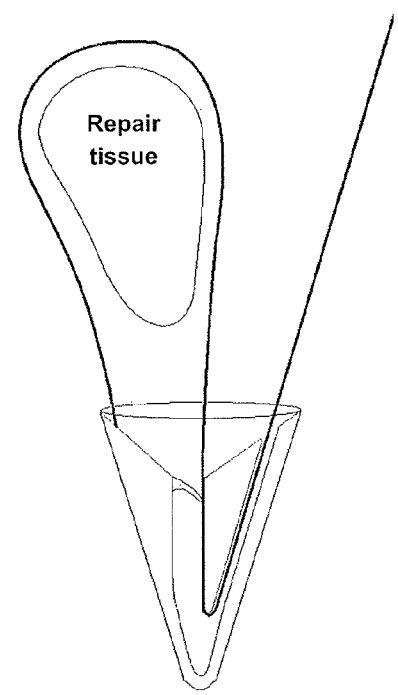
Figure 52E:
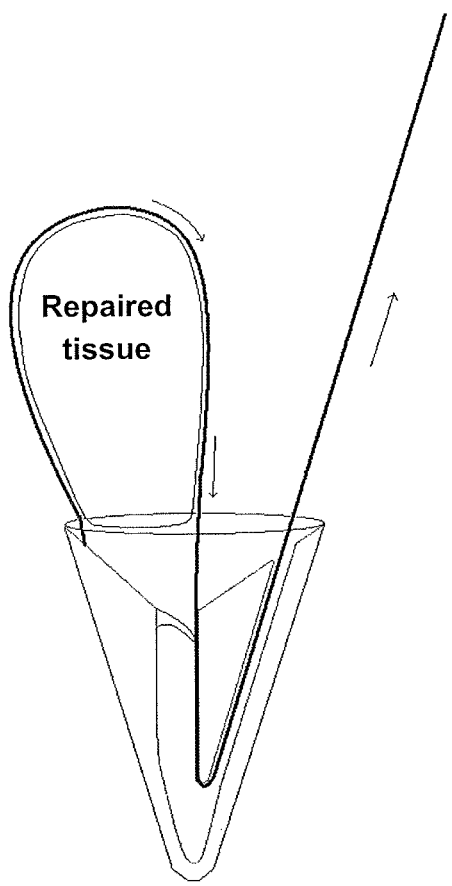
Figure 53C:
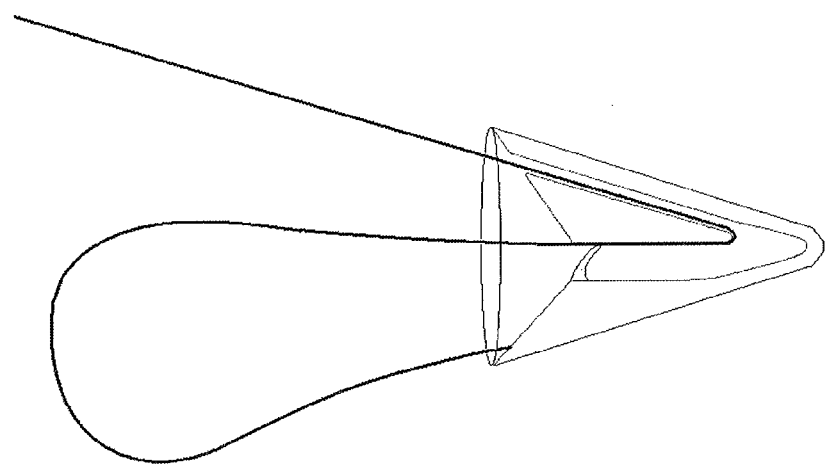
FIG. 53A-53C is another example illustrating the use of a knotless suture anchor.
Figure 53B:
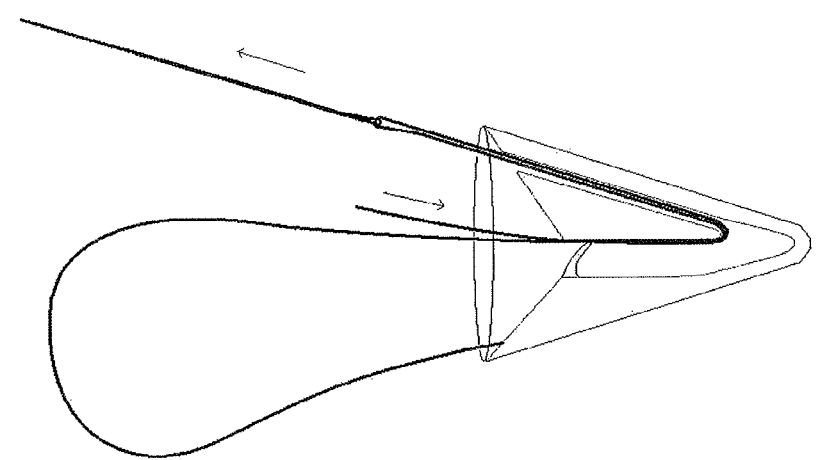
Figure 53A:
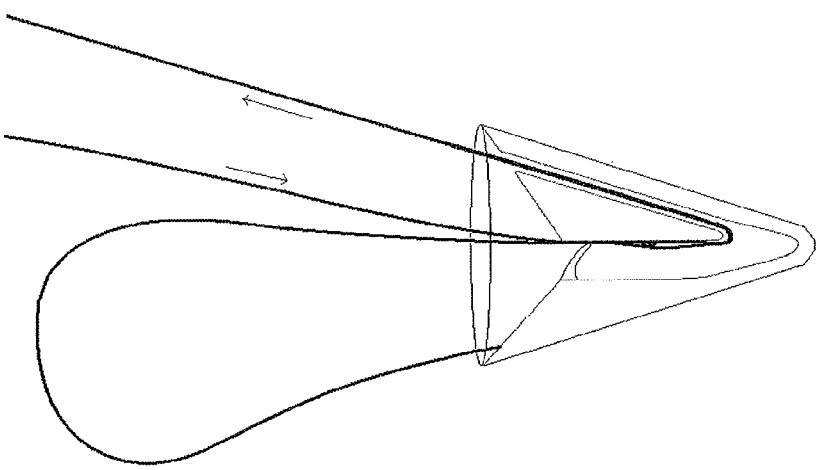
Figure 55:
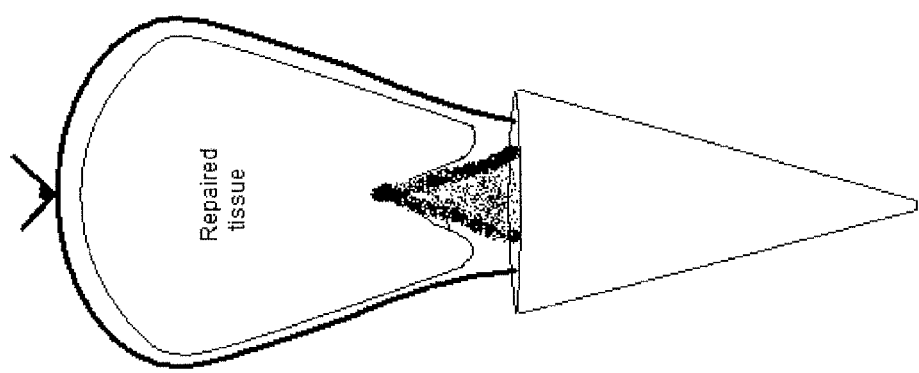
FIG. 55 illustrates the use of a knotless suture anchor with a therapeutic spike in body tissue.
Figure 56:
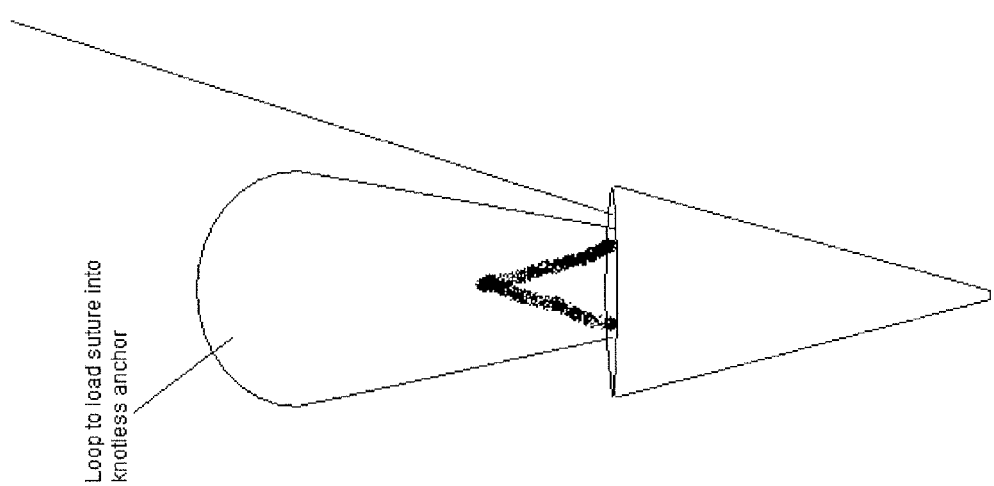
FIG. 56 illustrates a knotless suture anchor with a therapeutic spike having a loop of suture connected thereto.
Figure 57:
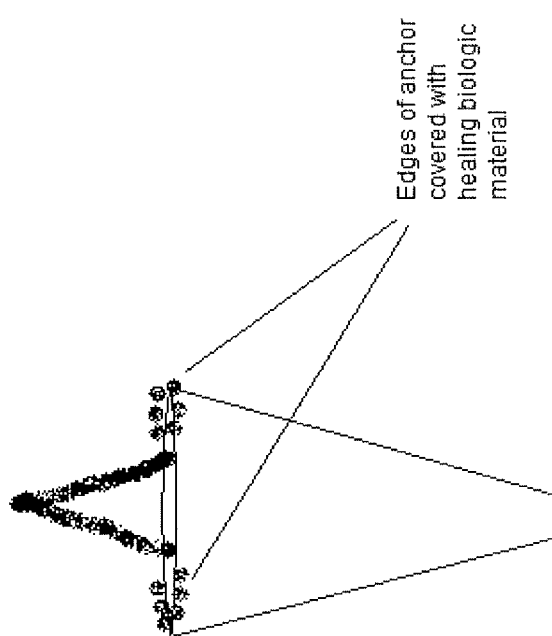
FIG. 57 illustrates a knotless suture anchor with a therapeutic spike and the edges of the anchor covered with a biologic material.

FIGS. 52A-52E illustrate the operation of another variation of a knotless suture anchor as described herein. In this example, the suture being anchored is pulled fully through the anchor so that the loop string is completely removed from the anchor and the patient. The suture can then be tightened/cinched down to pull the tissue down to the bone by simply pulling on the suture end. The suture engages the one-way lock within the anchor body, and is therefore held in place. Afterwards, the suture may be removed from the patient. FIG. 53A-53C shows a similar example. In FIG. 52A, the suture anchor includes an anchor body, from which a loop string

41403 and a loop-puller string 41405 extend. An optional suture 41401 is also shown extending from the body of the anchor. In operation, the suture anchor is first inserted and anchored into the body; the suture that will be used to pass through or around tissue 41401 is not passed through the loop 41403 until after the suture anchor has been placed and secured into the body (prior to the step shown in FIG. 52A). After passing a suture (such as the attached suture 41401, although a suture that has not been previously attached to the suture anchor may also be used) through or around the target tissue, the suture may be passed through the loop. For example, as described above, a suture passer may be used to pass the suture end through the loop. As illustrated in FIG. 52B, thereafter, the loop-puller string 41405 may be pulled to draw the loop (and therefore the portion of the suture passing through the loop) into the body of the knotless suture anchor. In the variation shown in FIG. 52A-52E, the loop is drawn completely out of the suture anchor, while continuing to pull the suture 41401 through the suture anchor, as shown in FIG. 52C. In this case, the suture is sufficiently long so that it can be pulled completely through the suture anchor and out of the patient by the loop. The suture is engaged by the one-way lock within the suture anchor, so that once it is pulled by the loop (e.g., in the direction shown by the arrows), it cannot be drawn in the opposite direction. In FIG. 52D, the suture 41401 has been completely passed through the suture anchor, and the distal end of the suture 41401 is grasped by a surgeon (not shown) either within or outside of the patient, so that the distal end can be further drawn into the suture anchor. Pulling the suture further into the suture anchor at this point may draw the anchored material ("repair tissue") towards the anchor body, or at least tension the suture and thereby secure the tissue. This is further illustrated in FIG. 52E. Thereafter, the portion of the suture extending from the suture anchor which is not passing through or around the repair tissue may be trimmed or cut, as mentioned above. FIGS. 53A-53C illustrates a similar variation, without showing the tissue being repaired.

In any of the variations described herein, the suture to be anchored is not passed through the loop of the suture anchor until after the anchor is placed and/or anchored into the body. As mentioned above, the suture is passed into the loop once the anchor has been positioned. Thus, the suture is pulled, pushed, or otherwise passed through the loop after the anchor has been fully implanted within the body (e.g., bone).

Referring to FIGS. 54-57, a suture anchor and/or a knotless suture anchor can be modified to have a tissue healing enhancing substance or material incorporated to the region of the anchor to which the repaired tissue will be into contact after the sutures have been tied down (as is the case with typical suture anchors) or cinched down (as is typical of knotless suture anchors). The biologic healing enhancing material, may be, but is not limited to, growth factors, platelet rich plasma, osteoconductive substances, osteoinductive substances, osteogenic substances, substances that enhance ligament and/or tendon healing, adhesive substances (e.g., glue, etc.), or the like. The material may have a three dimensional prominence or spike that penetrates or interdigitates into the repaired tissue as the tissue is pulled, tied or cinched down to the implanted anchor.

Any of the knotless anchors described herein can be loaded and/or unloaded wile entirely located within the tissue (e.g., within the shoulder). In FIGS. 10A, 11A and 14A, the illustrated procedures could all be performed entirely within the tissue (from entirely within the tissue, the suture can be passed through the loop that extends from the anchor, or in other words the anchor could be 'loaded'). Thus, the anchor could be positioned within the tissue prior to loading a suture through the tissue. The suture may be passed through the loop of the anchor while both the suture and the loop (e.g., the entire anchor) is positioned and/or affixed in the tissue. In some variations a separate manipulator (e.g., a hook, forceps, etc.) could be used to position the suture through the loop/anchor.

Although the example illustrated above shows the suture being passed through the tissue from after the suture has been anchored (e.g., to a bone), unanchored suture may be used. For example, a length of suture may be pulled into the tissue for loading into the suture passer as described herein using a manipulator (e.g., having a hook, graspers, etc.).

In some variations, the suture is initially loaded to the suture passer outside of the body, and passed at least once through the tissue; thereafter the method described above may be used to unload/reload the suture to the suture passer while the device is within the tissue, without requiring removal of the device. For example, a length of suture may be passed through a loop and the suture passer inserted into the tissue. The suture passer may be inserted in a minimally invasive way (e.g., using a cannula or access port) or in an open or partially open procedure. The suture may then be passed through the tissue as described above, so that it is doubled. One end of the suture may be held or otherwise secured, so that the unsecured end may be drawn through the loop, leaving the suture in place, so that it can be passed through the tissue as a single length (rather than a double).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of suturing tissue using a suture passer that is loaded with a suturing element while positioned within a patient, the method comprising:
   positioning the suture passer within the patient;
   coupling a suture to a loadable end of the suture passer while the loadable end of the suture passer and the suture are within the tissue;
   passing the suture through a target tissue within the patient using the suture passer;
   de-coupling the suture from the suture passer while the loadable end of the suture passer is within the tissue; and
   coupling the same or a different suture to the suture passer after de-coupling the suture.

2. The method of claim 1, wherein positioning the suture passer within the patient comprises positioning two jaws of the suture passer around the target tissue.

3. The method of claim 1, further comprising extending a tissue penetrator through the target tissue positioned between two jaws of the suture passer.

4. The method of claim 1, wherein the step of coupling the suture to the loadable end comprises coupling the suture to a suture shuttle that is coupled to the loadable end of the suture passer.

5. The method of claim 1, wherein the step of coupling the suture to the loadable end comprises passing a suture through an eyelet of a suture shuttle that is coupled to the loadable end of the suture passer.

6. The method of claim 1, wherein the step of coupling the suture to the loadable end comprises using a hooked tool to pull the suture through an opening of a suture shuttle that is coupled to the loadable end of the suture passer.

7. The method of claim 1, further comprising anchoring the suture to the tissue before coupling the suture to the loadable end of the suture passer.

8. The method of claim 1, wherein the step of positioning comprises positioning a continuous suture passer within the tissue.

9. The method of claim 1, wherein the suture passer comprises a continuous suture passer having a first and second jaw and a tissue penetrator configured so that the tissue penetrator is configured to extend from the first jaw, through the tissue and engage the second jaw, to alternately exchange a suture shuttle between the tissue penetrator and the second jaw.

10. The method of claim 1, wherein the step of coupling the suture to the loadable end comprises coupling the suture to a suture shuttle when the suture shuttle is releasably secured within the suture passer.

11. The method of claim 1, wherein the step of positioning the suture passer comprises percutaneously positioning the continuous suture passer.

12. The method of claim 1, wherein the step of coupling the suture to the loadable end comprises coupling the suture to a pull wire that is coupled to the loadable end of the suture passer.

13. The method of claim 12, wherein the pull wire is attached to a suture shuttle.

14. The method of claim 1, wherein positioning the suture passer within the patient comprises positioning the suture passer within the patient's knee.

15. A method of suturing tissue using a suture passer that is loaded with a suturing element while positioned within a patient's knee, the method comprising:

positioning the suture passer within the patient's knee;

coupling a suture to a loadable end of the suture passer while the loadable end of the suture passer and the suture are within the patient's knee;

passing the suture through a meniscus tissue within the patient using the suture passer;

de-coupling the suture from the suture passer while the loadable end of the suture passer is within the patient's knee; and coupling the same or a different suture to the suture passer after de-coupling the suture.

* * * * *